US008114021B2

(12) United States Patent
Robertson et al.

(10) Patent No.: US 8,114,021 B2
(45) Date of Patent: Feb. 14, 2012

(54) BODY-ASSOCIATED RECEIVER AND METHOD

(75) Inventors: Timothy Robertson, Belmont, CA (US); Fataneh Omidvar, Danville, CA (US); Yashar Behzadi, San Francisco, CA (US); Lawrence Arne, Redwood City, CA (US); Kenneth Rowberry, San Jose, CA (US); James Hutchison, Palo Alto, CA (US); Robert Leichner, Menlo Park, CA (US); George Savage, Portola Valley, CA (US); Andrew Thompson, Portola Valley, CA (US); Mark Zdeblick, Portola Valley, CA (US); Marc Kreidler, Sunnyvale, CA (US); Hooman Hafezi, Redwood City, CA (US); Robert Duck, San Francisco, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 155 days.

(21) Appl. No.: 12/673,326

(22) PCT Filed: Dec. 15, 2009

(86) PCT No.: PCT/US2009/068128
§ 371 (c)(1),
(2), (4) Date: Feb. 12, 2010

(87) PCT Pub. No.: WO2010/075115
PCT Pub. Date: Jul. 1, 2010

(65) Prior Publication Data
US 2010/0312188 A1  Dec. 9, 2010

Related U.S. Application Data

(63) Continuation-in-part of application No. 11/912,475, filed on Apr. 28, 2006, and a continuation-in-part of application No. 12/324,798, filed on Nov. 26, 2008.

(60) Provisional application No. 61/240,571, filed on Sep. 8, 2009, provisional application No. 61/160,289, filed on Mar. 13, 2009, provisional application No. 61/122,723, filed on Dec. 15, 2008.

(51) Int. Cl.
*A61M 5/20* (2006.01)
*A61B 5/00* (2006.01)
(52) U.S. Cl. ........ 600/300; 600/301; 375/133; 375/130; 604/67; 604/156
(58) Field of Classification Search .......... 600/300–301, 600/363–365, 372–374, 377–379, 382–384, 600/386–394, 481, 485, 500–503, 508, 515–519, 600/529–531, 544–547, 549, 587–595; 128/920–925; 705/2–3
See application file for complete search history.

(56) References Cited

U.S. PATENT DOCUMENTS
3,607,788 A  9/1971 Adolph
(Continued)

FOREIGN PATENT DOCUMENTS
EP  1246356  10/2002
(Continued)

OTHER PUBLICATIONS

Arshak et al., A Review and Adaptation of Methods of Object Tracking to Telemetry Capsules IC-Med (2007) vol. 1, No. 1, Issue 1, pp. 35 of 46.

(Continued)

*Primary Examiner* — Sam Yao
*Assistant Examiner* — Marie Archer
(74) *Attorney, Agent, or Firm* — Bozicevic, Field & Francis LLP; Bret E. Field

(57) ABSTRACT

Receivers, which may be external or implantable, are provided. Aspects of receivers of the invention include the presence of one or more of: a high power-low power module; an intermediary module; a power supply module configured to activate and deactivate one or more power supplies to a high power processing block; a serial peripheral interface bus connecting master and slave blocks; and a multi-purpose connector. Receivers of the invention may be configured to receive a conductively transmitted signal. Also provided are systems that include the receivers, as well as methods of using the same. Additionally systems and methods are disclosed for using a receiver for coordinating with dosage delivery systems.

14 Claims, 37 Drawing Sheets

U.S. PATENT DOCUMENTS

| | | | |
|---|---|---|---|
| 3,642,008 A | 2/1972 | Bolduc | |
| 3,679,480 A | 7/1972 | Brown et al. | |
| 3,682,160 A | 8/1972 | Murata | |
| 3,719,183 A | 3/1973 | Schwartz | |
| 3,828,766 A | 8/1974 | Krasnow | |
| 3,837,339 A | 9/1974 | Aisenberg et al. | |
| 3,989,050 A | 11/1976 | Buchalter | |
| 4,077,397 A | 3/1978 | Ellis | |
| 4,077,398 A | 3/1978 | Ellis | |
| 4,082,087 A | 4/1978 | Howson | |
| 4,090,752 A | 5/1978 | Long | |
| 4,106,348 A | 8/1978 | Auphan | |
| 4,129,125 A | 12/1978 | Lester | |
| 4,166,453 A | 9/1979 | McClelland | |
| 4,239,046 A | 12/1980 | Ong | |
| 4,269,189 A | 5/1981 | Abraham | |
| 4,331,654 A | 5/1982 | Morris | |
| 4,345,588 A | 8/1982 | Widder et al. | |
| 4,418,697 A | 12/1983 | Tama | |
| 4,425,117 A | 1/1984 | Hugemann | |
| 4,494,950 A | 1/1985 | Fischell | |
| 4,559,950 A | 12/1985 | Vaughan | |
| 4,635,641 A | 1/1987 | Hoffman | |
| 4,654,165 A | 3/1987 | Eisenber | |
| 4,669,479 A | 6/1987 | Dunseath | |
| 4,725,997 A | 2/1988 | Urquhart et al. | |
| 4,763,659 A | 8/1988 | Dunseath | |
| 4,784,162 A | 11/1988 | Ricks | |
| 4,793,825 A | 12/1988 | Benjamin et al. | |
| 4,844,076 A | 7/1989 | Lesho | |
| 4,896,261 A | 1/1990 | Nolan | |
| 4,975,230 A | 12/1990 | Pinkhasov | |
| 4,987,897 A | 1/1991 | Funke | |
| 5,016,634 A | 5/1991 | Vock et al. | |
| 5,079,006 A | 1/1992 | Urguhart | |
| 5,167,626 A | 12/1992 | Casper | |
| 5,176,626 A | 1/1993 | Soehendra | |
| 5,261,402 A | 11/1993 | DiSabito | |
| 5,263,481 A | 11/1993 | Axelgaard et al. | |
| 5,281,287 A | 1/1994 | Lloyd | |
| 5,283,136 A | 2/1994 | Peled et al. | |
| 5,318,557 A | 6/1994 | Gross | |
| 5,394,882 A | 3/1995 | Mawhinney | |
| 5,458,141 A | 10/1995 | Neil et al. | |
| 5,485,841 A | 1/1996 | Watkin et al. | |
| 5,596,302 A | 1/1997 | Mastrocola et al. | |
| 5,634,468 A | 6/1997 | Platt | |
| 5,645,063 A | 7/1997 | Straka et al. | |
| 5,740,811 A | 4/1998 | Hedberg | |
| 5,792,048 A | 8/1998 | Schaefer | |
| 5,802,467 A | 9/1998 | Salazar | |
| 5,833,716 A | 11/1998 | Bar-Or | |
| 5,845,265 A | 12/1998 | Woolston | |
| 5,862,803 A | 1/1999 | Besson | |
| 5,868,136 A | 2/1999 | Fox | |
| 5,925,030 A | 7/1999 | Gross et al. | |
| 5,957,854 A | 9/1999 | Besson | |
| 5,974,124 A | 10/1999 | Schlueter, Jr. et al. | |
| 5,999,846 A | 12/1999 | Pardey et al. | |
| 6,018,680 A * | 1/2000 | Flower | 604/20 |
| 6,038,464 A | 3/2000 | Axelgaard et al. | |
| 6,042,710 A | 3/2000 | Dubrow | |
| 6,047,203 A | 4/2000 | Sackner | |
| 6,081,734 A | 6/2000 | Batz | |
| 6,095,985 A | 8/2000 | Raymond et al. | |
| 6,122,351 A | 9/2000 | Schlueter, Jr. et al. | |
| 6,141,592 A | 10/2000 | Pauly | |
| 6,200,265 B1 | 3/2001 | Walsh et al. | |
| 6,206,702 B1 | 3/2001 | Hayden et al. | |
| 6,217,744 B1 | 4/2001 | Crosby | |
| 6,231,593 B1 | 5/2001 | Meserol | |
| 6,245,057 B1 | 6/2001 | Sieben et al. | |
| 6,285,897 B1 | 9/2001 | Kilcoyne et al. | |
| 6,287,252 B1 | 9/2001 | Lugo | |
| 6,289,238 B1 | 9/2001 | Besson | |
| 6,315,719 B1 | 11/2001 | Rode et al. | |
| 6,358,202 B1 | 3/2002 | Arent | |
| 6,364,834 B1 | 4/2002 | Reuss | |
| 6,366,206 B1 | 4/2002 | Ishikawa et al. | |
| 6,371,927 B1 | 4/2002 | Brune | |
| 6,374,670 B1 | 4/2002 | Spelman | |
| 6,380,858 B1 | 4/2002 | Yarin et al. | |
| 6,394,997 B1 | 5/2002 | Lemelson | |
| 6,426,863 B1 | 7/2002 | Munshi | |
| 6,432,292 B1 | 8/2002 | Pinto et al. | |
| 6,440,069 B1 | 8/2002 | Raymond et al. | |
| 6,441,747 B1 | 8/2002 | Khair | |
| 6,445,951 B1 * | 9/2002 | Mouchawar | 607/28 |
| 6,477,424 B1 | 11/2002 | Thompson et al. | |
| 6,496,705 B1 | 12/2002 | Ng et al. | |
| 6,526,315 B1 | 2/2003 | Inagawa | |
| 6,544,174 B2 | 4/2003 | West | |
| 6,564,079 B1 | 5/2003 | Cory | |
| 6,577,893 B1 | 6/2003 | Besson | |
| 6,579,231 B1 | 6/2003 | Phipps | |
| 6,609,018 B2 | 8/2003 | Cory | |
| 6,612,984 B1 | 9/2003 | Kerr | |
| 6,632,175 B1 | 10/2003 | Marshall | |
| 6,632,216 B2 | 10/2003 | Houzego et al. | |
| 6,643,541 B2 | 11/2003 | Mok et al. | |
| 6,654,638 B1 | 11/2003 | Sweeney | |
| 6,663,846 B1 | 12/2003 | McCombs | |
| 6,673,474 B2 | 1/2004 | Yamamoto | |
| 6,680,923 B1 | 1/2004 | Leon | |
| 6,689,117 B2 | 2/2004 | Sweeney et al. | |
| 6,694,161 B2 | 2/2004 | Mehrotra | |
| 6,704,602 B2 | 3/2004 | Berg et al. | |
| 6,720,923 B1 | 4/2004 | Hayward et al. | |
| 6,738,671 B2 | 5/2004 | Christphersom et al. | |
| 6,740,033 B1 | 5/2004 | Olejniczak et al. | |
| 6,745,082 B2 | 6/2004 | Axelgaard et al. | |
| 6,755,783 B2 | 6/2004 | Cosentino | |
| 6,757,523 B2 | 6/2004 | Fry | |
| 6,800,060 B2 | 10/2004 | Marshall | |
| 6,801,137 B2 | 10/2004 | Eggers et al. | |
| 6,822,554 B2 | 11/2004 | Vrijens et al. | |
| 6,836,862 B1 | 12/2004 | Erekson et al. | |
| 6,839,659 B2 | 1/2005 | Tarassenko et al. | |
| 6,840,904 B2 | 1/2005 | Goldberg | |
| 6,842,636 B2 | 1/2005 | Perrault | |
| 6,845,272 B1 | 1/2005 | Thomsen | |
| 6,864,780 B2 | 3/2005 | Doi | |
| 6,879,810 B2 | 4/2005 | Bouet | |
| 6,909,878 B2 | 6/2005 | Haller | |
| 6,922,592 B2 | 7/2005 | Thompson et al. | |
| 6,928,370 B2 | 8/2005 | Anuzis et al. | |
| 6,929,636 B1 | 8/2005 | Von Alten | |
| 6,937,150 B2 | 8/2005 | Medema | |
| 6,942,616 B2 | 9/2005 | Kerr | |
| 6,951,536 B2 | 10/2005 | Yokoi | |
| 6,957,107 B2 | 10/2005 | Rogers et al. | |
| 6,968,153 B1 | 11/2005 | Heinonen | |
| 6,987,965 B2 | 1/2006 | Ng et al. | |
| 6,990,082 B1 | 1/2006 | Zehavi et al. | |
| 7,002,476 B2 | 2/2006 | Rapchak | |
| 7,004,395 B2 | 2/2006 | Koenck | |
| 7,009,634 B2 | 3/2006 | Iddan et al. | |
| 7,009,946 B1 | 3/2006 | Kardach | |
| 7,013,162 B2 | 3/2006 | Gorsuch | |
| 7,016,648 B2 | 3/2006 | Haller | |
| 7,020,508 B2 | 3/2006 | Stivoric | |
| 7,024,248 B2 | 4/2006 | Penner et al. | |
| 7,031,745 B2 | 4/2006 | Shen | |
| 7,031,857 B2 | 4/2006 | Tarassenko et al. | |
| 7,039,453 B2 | 5/2006 | Mullick | |
| 7,046,649 B2 | 5/2006 | Awater et al. | |
| 7,118,531 B2 | 10/2006 | Krill | |
| 7,127,300 B2 | 10/2006 | Mazar et al. | |
| 7,146,228 B2 | 12/2006 | Nielsen | |
| 7,146,449 B2 | 12/2006 | Do et al. | |
| 7,149,581 B2 | 12/2006 | Goedeke et al. | |
| 7,154,071 B2 | 12/2006 | Sattler et al. | |
| 7,155,232 B2 | 12/2006 | Godfrey et al. | |
| 7,160,258 B2 | 1/2007 | Imran | |
| 7,164,942 B2 | 1/2007 | Avrahami | |
| 7,171,166 B2 | 1/2007 | Ng et al. | |
| 7,171,177 B2 | 1/2007 | Park et al. | |

| Patent/Pub No. | Date | Name |
|---|---|---|
| 7,171,259 B2 | 1/2007 | Rytky |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,505,795 B1 * | 3/2009 | Lim et al. ............ 455/574 |
| 7,510,121 B2 | 3/2009 | Koenck |
| 7,512,448 B2 | 3/2009 | Malick |
| 7,515,043 B2 | 4/2009 | Welch |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,616,111 B2 | 11/2009 | Covannon |
| 7,617,001 B2 | 11/2009 | Penner et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,809,399 B2 | 10/2010 | Lu |
| 7,844,341 B2 | 11/2010 | Von Arx et al. |
| 2001/0027331 A1 | 10/2001 | Thompson |
| 2001/0044588 A1 | 11/2001 | Mault |
| 2001/0051766 A1 | 12/2001 | Gazdinski |
| 2002/0002326 A1 | 1/2002 | Causey, III |
| 2002/0026111 A1 | 2/2002 | Ackerman |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0033032 A1 * | 2/2003 | Lind et al. ............ 700/52 |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0106963 A1 * | 6/2004 | Tsukamoto et al. ............ 607/33 |
| 2004/0115517 A1 | 6/2004 | Fukada et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/1215084 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0048960 A1 * | 3/2005 | Yamauchi et al. ............ 455/418 |
| 2005/0062644 A1 | 3/2005 | Leci |

| | | |
|---|---|---|
| 2005/0065407 A1 | 3/2005 | Nakamura et al. |
| 2005/0070778 A1 | 3/2005 | Lackey |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0177111 A1* | 8/2005 | Ozeri et al. ............... 604/154 |
| 2005/0182389 A1* | 8/2005 | LaPorte et al. ............ 604/890.1 |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0046038 A1 | 2/2008 | Hill |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |

| | | | | | | |
|---|---|---|---|---|---|---|
| 2008/0312522 | A1 | 12/2008 | Rowlandson | 2009/0216101 A1 | 8/2009 | Say et al. |
| 2008/0316020 | A1 | 12/2008 | Robertson | 2009/0216102 A1 | 8/2009 | Say et al. |
| 2009/0009332 | A1 | 1/2009 | Nunez et al. | 2009/0227204 A1 | 9/2009 | Robertson et al. |
| 2009/0024045 | A1 | 1/2009 | Prakash | 2009/0227876 A1 | 9/2009 | Tran |
| 2009/0030297 | A1 | 1/2009 | Miller | 2009/0227940 A1 | 9/2009 | Say et al. |
| 2009/0034209 | A1 | 2/2009 | Joo | 2009/0227941 A1 | 9/2009 | Say et al. |
| 2009/0043171 | A1 | 2/2009 | Rule | 2009/0228214 A1 | 9/2009 | Say et al. |
| 2009/0048498 | A1 | 2/2009 | Riskey | 2009/0231125 A1 | 9/2009 | Baldus |
| 2009/0062634 | A1 | 3/2009 | Say et al. | 2009/0234200 A1 | 9/2009 | Husheer |
| 2009/0062670 | A1 | 3/2009 | Sterling | 2009/0243833 A1 | 10/2009 | Huang |
| 2009/0069642 | A1 | 3/2009 | Gao | 2009/0253960 A1 | 10/2009 | Takenaka et al. |
| 2009/0069655 | A1 | 3/2009 | Say et al. | 2009/0256702 A1 | 10/2009 | Robertson |
| 2009/0069656 | A1 | 3/2009 | Say et al. | 2009/0264714 A1 | 10/2009 | Chou |
| 2009/0069657 | A1 | 3/2009 | Say et al. | 2009/0264964 A1 | 10/2009 | Abrahamson |
| 2009/0069658 | A1 | 3/2009 | Say et al. | 2009/0265186 A1 | 10/2009 | Tarassenko et al. |
| 2009/0076343 | A1 | 3/2009 | James | 2009/0273467 A1 | 11/2009 | Elixmann |
| 2009/0082645 | A1 | 3/2009 | Hafezi et al. | 2009/0281539 A1 | 11/2009 | Selig |
| 2009/0088618 | A1 | 4/2009 | Ameson | 2009/0295548 A1 | 12/2009 | Ronkka |
| 2009/0099435 | A1 | 4/2009 | Say et al. | 2009/0296677 A1 | 12/2009 | Mahany |
| 2009/0110148 | A1 | 4/2009 | Zhang | 2009/0303920 A1 | 12/2009 | Mahany |
| 2009/0112626 | A1 | 4/2009 | Talbot | 2009/0312619 A1 | 12/2009 | Say et al. |
| 2009/0124871 | A1 | 5/2009 | Arshak | 2009/0318761 A1 | 12/2009 | Rabinovitz |
| 2009/0131774 | A1 | 5/2009 | Sweitzer | 2009/0318779 A1 | 12/2009 | Tran |
| 2009/0135886 | A1 | 5/2009 | Robertson et al. | 2009/0318783 A1 | 12/2009 | Rohde |
| 2009/0157113 | A1 | 6/2009 | Marcotte | 2009/0318793 A1 | 12/2009 | Datta |
| 2009/0157358 | A1 | 6/2009 | Kim | 2010/0010330 A1 | 1/2010 | Rankers |
| 2009/0161602 | A1 | 6/2009 | Matsumoto | 2010/0049006 A1 | 2/2010 | Magar |
| 2009/0163789 | A1 | 6/2009 | Say et al. | 2010/0049012 A1 | 2/2010 | Dijksman et al. |
| 2009/0171180 | A1 | 7/2009 | Pering | 2010/0049069 A1 | 2/2010 | Tarassenko et al. |
| 2009/0173628 | A1 | 7/2009 | Say et al. | 2010/0056878 A1 | 3/2010 | Partin |
| 2009/0177055 | A1 | 7/2009 | Say et al. | 2010/0056891 A1 | 3/2010 | Say et al. |
| 2009/0177056 | A1 | 7/2009 | Say et al. | 2010/0056939 A1 | 3/2010 | Tarassenko et al. |
| 2009/0177057 | A1 | 7/2009 | Say et al. | 2010/0057041 A1 | 3/2010 | Hayter |
| 2009/0177058 | A1 | 7/2009 | Say et al. | 2010/0062709 A1 | 3/2010 | Kato |
| 2009/0177059 | A1 | 7/2009 | Say et al. | 2010/0063438 A1 | 3/2010 | Bengtsson |
| 2009/0177060 | A1 | 7/2009 | Say et al. | 2010/0063841 A1 | 3/2010 | D'Ambrosia |
| 2009/0177061 | A1 | 7/2009 | Say et al. | 2010/0069002 A1 | 3/2010 | Rong |
| 2009/0177062 | A1 | 7/2009 | Say et al. | 2010/0099967 A1 | 4/2010 | Say et al. |
| 2009/0177063 | A1 | 7/2009 | Say et al. | 2010/0099968 A1 | 4/2010 | Say et al. |
| 2009/0177064 | A1 | 7/2009 | Say et al. | 2010/0099969 A1 | 4/2010 | Say et al. |
| 2009/0177065 | A1 | 7/2009 | Say et al. | 2010/0100077 A1 | 4/2010 | Rush |
| 2009/0177066 | A1 | 7/2009 | Say et al. | 2010/0100078 A1 | 4/2010 | Say et al. |
| 2009/0182206 | A1 | 7/2009 | Najafi | 2010/0106001 A1 | 4/2010 | Say et al. |
| 2009/0182212 | A1 | 7/2009 | Say et al. | 2010/0118853 A1 | 5/2010 | Godfrey |
| 2009/0182213 | A1 | 7/2009 | Say et al. | 2010/0139672 A1 | 6/2010 | Kroll et al. |
| 2009/0182214 | A1 | 7/2009 | Say et al. | 2010/0168659 A1 | 7/2010 | Say et al. |
| 2009/0182215 | A1 | 7/2009 | Say et al. | 2010/0179398 A1 | 7/2010 | Say et al. |
| 2009/0182388 | A1 | 7/2009 | Von Arx | 2010/0185055 A1 | 7/2010 | Robertson |
| 2009/0187088 | A1 | 7/2009 | Say et al. | 2010/0191073 A1 | 7/2010 | Tarassenko et al. |
| 2009/0187089 | A1 | 7/2009 | Say et al. | 2010/0210299 A1 | 8/2010 | Gorbachov |
| 2009/0187090 | A1 | 7/2009 | Say et al. | 2010/0222652 A1 | 9/2010 | Cho |
| 2009/0187091 | A1 | 7/2009 | Say et al. | 2010/0228113 A1 | 9/2010 | Solosko |
| 2009/0187092 | A1 | 7/2009 | Say et al. | 2010/0234706 A1 | 9/2010 | Gilland |
| 2009/0187093 | A1 | 7/2009 | Say et al. | 2010/0234715 A1 | 9/2010 | Shin |
| 2009/0187094 | A1 | 7/2009 | Say et al. | 2010/0234914 A1 | 9/2010 | Shen |
| 2009/0187095 | A1 | 7/2009 | Say et al. | 2010/0245091 A1 | 9/2010 | Singh |
| 2009/0187381 | A1 | 7/2009 | King et al. | 2010/0249881 A1 | 9/2010 | Corndorf |
| 2009/0192351 | A1 | 7/2009 | Nishino | 2010/0256461 A1 | 10/2010 | Mohamedali |
| 2009/0192368 | A1 | 7/2009 | Say et al. | 2010/0259543 A1 | 10/2010 | Tarassenko et al. |
| 2009/0192369 | A1 | 7/2009 | Say et al. | 2010/0268048 A1 | 10/2010 | Say et al. |
| 2009/0192370 | A1 | 7/2009 | Say et al. | 2010/0268049 A1 | 10/2010 | Say et al. |
| 2009/0192371 | A1 | 7/2009 | Say et al. | 2010/0268050 A1 | 10/2010 | Say et al. |
| 2009/0192372 | A1 | 7/2009 | Say et al. | 2010/0274111 A1 | 10/2010 | Say et al. |
| 2009/0192373 | A1 | 7/2009 | Say et al. | 2010/0280345 A1 | 11/2010 | Say et al. |
| 2009/0192374 | A1 | 7/2009 | Say et al. | 2010/0280346 A1 | 11/2010 | Say et al. |
| 2009/0192375 | A1 | 7/2009 | Say et al. | 2010/0298730 A1 | 11/2010 | Tarassenko et al. |
| 2009/0192376 | A1 | 7/2009 | Say et al. | 2010/0312580 A1 | 12/2010 | Tarassenko et al. |
| 2009/0192377 | A1 | 7/2009 | Say et al. | | | |
| 2009/0192378 | A1 | 7/2009 | Say et al. | | | |
| 2009/0192379 | A1 | 7/2009 | Say et al. | | | |

FOREIGN PATENT DOCUMENTS

| | | |
|---|---|---|
| EP | 1789128 | 5/2007 |
| EP | 2143369 | 1/2010 |
| JP | 61072712 | 4/1986 |
| JP | 2005-304880 | 4/2005 |
| WO | 8802237 | 4/1988 |
| WO | WO8802237 | 4/1988 |
| WO | WO9308734 | 5/1993 |
| WO | WO9319667 | 10/1993 |
| WO | WO9843537 | 10/1998 |
| WO | WO9959465 | 11/1999 |

Additional entries (left column continued):

| | | | |
|---|---|---|---|
| 2009/0198115 A1 | 8/2009 | Say et al. | |
| 2009/0198116 A1 | 8/2009 | Say et al. | |
| 2009/0198175 A1 | 8/2009 | Say et al. | |
| 2009/0203964 A1 | 8/2009 | Shimizu et al. | |
| 2009/0203971 A1 | 8/2009 | Sciarappa | |
| 2009/0203972 A1 | 8/2009 | Heneghan | |
| 2009/0203978 A1 | 8/2009 | Say et al. | |
| 2009/0204265 A1 | 8/2009 | Hackett | |
| 2009/0210164 A1 | 8/2009 | Say et al. | |

| | | |
|---|---|---|
| WO | WO0033246 | 6/2000 |
| WO | WO0100085 | 1/2001 |
| WO | WO 0147466 | 7/2001 |
| WO | WO0174011 | 10/2001 |
| WO | WO0180731 | 11/2001 |
| WO | WO 0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO 2004014225 | 2/2004 |
| WO | WO2004039256 | 5/2004 |
| WO | WO2004066834 | 8/2004 |
| WO | WO2004068881 | 8/2004 |
| WO | WO2004109316 | 12/2004 |
| WO | WO2005011237 | 2/2005 |
| WO | WO 2005020023 | 3/2005 |
| WO | WO2005024687 | 3/2005 |
| WO | WO2005047837 | 5/2005 |
| WO | WO2005051166 | 6/2005 |
| WO | WO2005110238 | 11/2005 |
| WO | WO2006027586 | 3/2006 |
| WO | WO 2006055892 | 5/2006 |
| WO | WO 2006055956 | 5/2006 |
| WO | WO2006075016 | 7/2006 |
| WO | WO2006100620 | 9/2006 |
| WO | WO 2006104843 | 10/2006 |
| WO | WO 2006116718 | 11/2006 |
| WO | WO 2006127355 | 11/2006 |
| WO | WO 2007001724 | 1/2007 |
| WO | WO 2007001742 | 1/2007 |
| WO | WO 2007013952 | 2/2007 |
| WO | WO 2007014084 | 2/2007 |
| WO | WO2007014527 | 2/2007 |
| WO | WO 2007021496 | 2/2007 |
| WO | WO 2007027660 | 3/2007 |
| WO | WO 2007028035 | 3/2007 |
| WO | WO2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | WO 2007127316 | 11/2007 |
| WO | WO2007127879 | 11/2007 |
| WO | WO2007128165 | 11/2007 |
| WO | WO 2007130491 | 11/2007 |
| WO | WO2007143535 | 12/2007 |
| WO | WO 2007149546 | 12/2007 |
| WO | WO 2008008281 | 1/2008 |
| WO | WO 2008030482 | 3/2008 |
| WO | WO 2008052136 | 5/2008 |
| WO | WO 2008063626 | 5/2008 |
| WO | WO 2008066617 | 6/2008 |
| WO | WO 2008076464 | 6/2008 |
| WO | WO 2008089232 | 7/2008 |
| WO | WO2008091683 | 7/2008 |
| WO | WO 2008095183 | 8/2008 |
| WO | WO2008097652 | 8/2008 |
| WO | WO 2008101107 | 8/2008 |
| WO | WO 2008112577 | 9/2008 |
| WO | WO 2008112578 | 9/2008 |
| WO | 2008120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO 2009006615 | 1/2009 |
| WO | WO 2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO 2009146082 | 12/2009 |
| WO | WO2010000085 | 1/2010 |
| WO | WO2010009100 | 1/2010 |
| WO | WO 2010011833 | 1/2010 |
| WO | 2010019778 | 2/2010 |
| WO | 2010057049 | 5/2010 |
| WO | WO2010107563 | 9/2010 |
| WO | WO2010135516 | 11/2010 |

OTHER PUBLICATIONS

"ASGE Technology Status Evaluation Report: wireless capsule endoscopy" American Soc. For Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Barrie, Heidelberg pH capsule gastric analysis. Texbook of Natural Medicine, (1992), Pizzorno, Murray & Barrie.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1):53.

Delvaux et al., "Capsule endoscopy: Technique and indications" Clinical Gastroenterology (2008) vol. 22, Issue 5, pp. 813-837.

Fawaz et al., "Enhanced Telemetry System using CP-QPSK Band-Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.

Given Imaging, "Agile Patency Brochure" http://www.inclino.no/documents/AgilePatencyBrochure_Global_GMB-0118-01.pdf;(N.D.) 4pp.

Gonzalez-Guillaumin et al., "Ingestible capsule for impedance and pH monitoring in the esophagus" IEEE Trans Biomed Eng. (2007) 54(12: 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Heydari et al., "Analysis of the PLL jitter due to power/ground and substrate noise"; IEEE Transactions on Circuits and Systems (2004) 51(12): 2404-16.

Intromedic, MicroCam Innovative Capsule Endoscope Pamphlet. 8 pp (http://www.intromedic.com/en/product/productinfo.asp).

Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

Mackay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

Melanson, "Walkers swallow RFID pills for science" Engadget (2008); http://www.engadget.com/2008/07/29/walkers-swallow-rfid-pills-for-science/.

Minimitter Co. Inc. "Actiheart" Traditional 510(k) Summary. Sep. 27, 2005.

Minimitter Co. Inc. Noninvasive technology to help your studies succeed. MiniMitter.com Mar. 31, 2009.

Mini Mitter Co, Inc. 510(k) Premarket Notification Mini-Logger for Diagnostic Spirometer. Sep. 21, 1999.

Mini Mitter Co, Inc. 510(k) Premarket Notification for VitalSense. Apr. 22, 2004.

Minimitter Co. Inc. VitalSense Integrated Physiological Monitoring System. Product Description.

Minimitter Co. Inc. VitalSense Wireless Vital Signs Monitoring. Temperatures.com Mar. 31, 2009.

Mohaverian et al., "Estimation of gastric residence time of the Heidelberg capsule in humans: effect of varying food composition" Gastroenterology (1985) 89:(2): 392-7.
"New 'smart pill' to track adherence" E-Health-Insider (2010) http://www.e-health-insider.com/news/5910/new_'smart_pill'_monitors_medicines.
Philips Respironics (http/minimitter.com/products.cfm) Products, Noninvasive Technology To Help Your Studies Succeed. 510(k) Permanent Notification for Vital Sense. Apr. 22, 2004.
"RFID "pill" monitors marchers" RFID News (2008) http://www.rfidnews.org/2008/07/23/rfid-pill-monitors-marchers/.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
"SensiVida minimally invasive clinical systems" Investor Presentation Oct. 2009 28pp; http://www.sensividamedtech.com/SensiVidaGeneralOctober09.pdf.
Shrivas et al., "A New Platform for Bioelectronics-Electronic Pill", Cummins College, N.D.; http://www.cumminscollege.org/downloads/electronics_and_telecommunication/Newsletters/Current%20Newsletters.pdf.
"The SmartPill Wireless Motility Capsule" SMARTPILL, The Measure of GI Health; http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Swedberg, "University Team Sees Ingestible RFID Tag as a Boon to Clinical Trials" RFID Journal Apr. 27, 2010; http://www.rfidjournal.com/article/view/7560/1.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
University of Florida News "Rx for health: Engineers design pill that signals it has been swallowed" (2010) 2pp.; http://news.ufl.edu/2010/03/31/antenna-pill-2/.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.
Hotz "The Really Smart Phone" The Wall Street Journal, What They Know (2011); 6 pp.; http://online.wsj.com/article/SB10001424052748704547604576263261679848814.html?mod=djemTECH_t.
ISFET—Ion Sensitive Field-Effect Transistor; MICROSENS S.A. pdf document. pp. 1-4.
Walkey, "MOSFET Struture and Processing"; 97.398* Physical Electronics Lecture 20; pp. 1-24.
AADE, "AADE 37th Annual Meeting San Antonio Aug. 4-7, 2010" American Association of Diabetes Educators (2010); http://www.diabeteseducator.org/annualmeeting/2010/index.html; 2 pp.
Juvenile Diabetes Research Foundation International (JDRF), "Artificial Pancreas Project" (2010); http://www.artificialpancreasproject.com/; 3 pp.
Lifescan, "OneTouch UltraLink™" http://www.lifescan.com/products/meters/ultralink (N.D.) 2 pp.
Medtronic, "CareLink Therapy Management Software for Diabetes" (2010); https://carelink.minimed.com/patient/entry.jsp?bhcp=1; 1 pp.
Medtronic, "Carelink™ USB" (n.d.) http://www.medtronicdiabetes.com/pdf/carelink_usb_factsheet.pdf 2pp.
Medtronic "The New MiniMed Paradigm® REAL-Time Revel™ System" http://www.medtronicdiabetes.com/products/index.html; 2 pp.
Medtronic, "Mini Med Paradigm® Revel™ Insulin Pump" (n.d.) http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Park, "Medtronic to Buy MiniMed for $3.7 Billion" (2001) HomeCare; http://homecaremag.com/mag/medical_medtronic_buy_minimed/; 2 pp.
"Smartlife awarded patent for knitted transducer" Innovation in Textiles News: http://www.innovationintextiles.com/articles/208.php; 2pp. (2009).
Gilson, D.R. "Molecular dynamics simulation of dipole interactions", Department of Physics, Hull University, Dec. 2002, p. 1-43.
Li, P-Y, et al. "An electrochemical intraocular drug delivery device", Sensors and Actuators A 143 (2008) p. 41-48.
NPL_AntennaBasics.pdf, p. 1-3.
Santini, J.T. et al, "Microchips as controlled drug delivery-devices", Agnew. Chem. Int. Ed. 2000, vol. 39, p. 2396-2407.
Shawgo, R.S. et al. "BioMEMS from drug delivery", Current Opinion in Solid State and Material Science 6 (2002), p. 329-334.
Soper, S.A. et al. "Bio-Mems Technologies and Applications", Chapter 12, "MEMS for Drug Delivery", p. 325-346.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Description of ePatch Technology Platform for ECG and EMG, located it http://www.madebydelta.com/imported/images/DELTA_Web/documents/ME/ePatch_ECG_EMG.pdf, Dated Sep. 2, 2010.

* cited by examiner

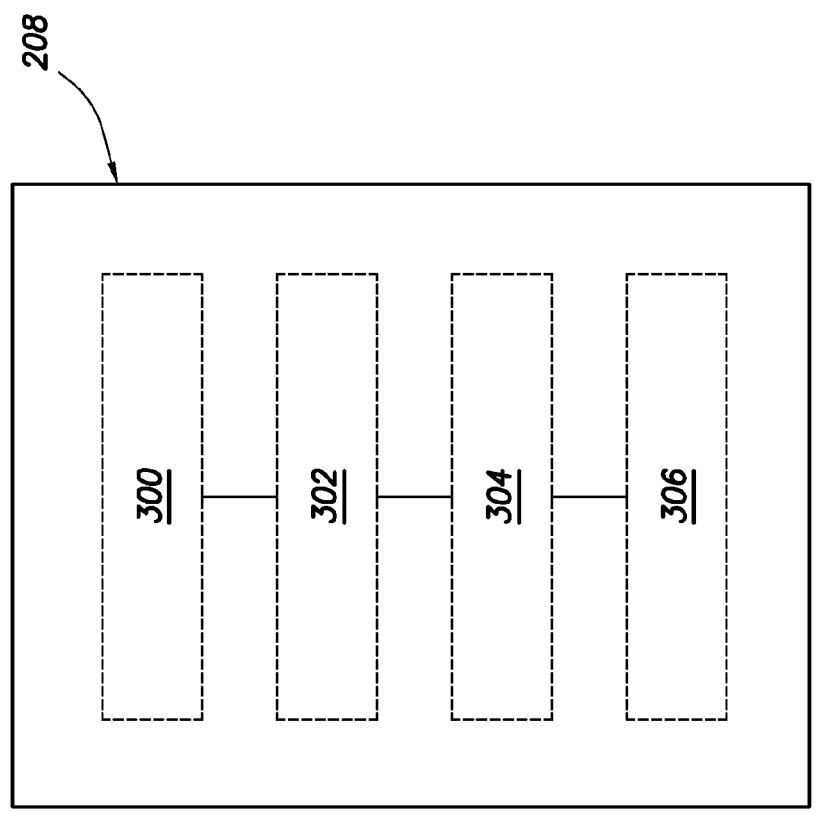
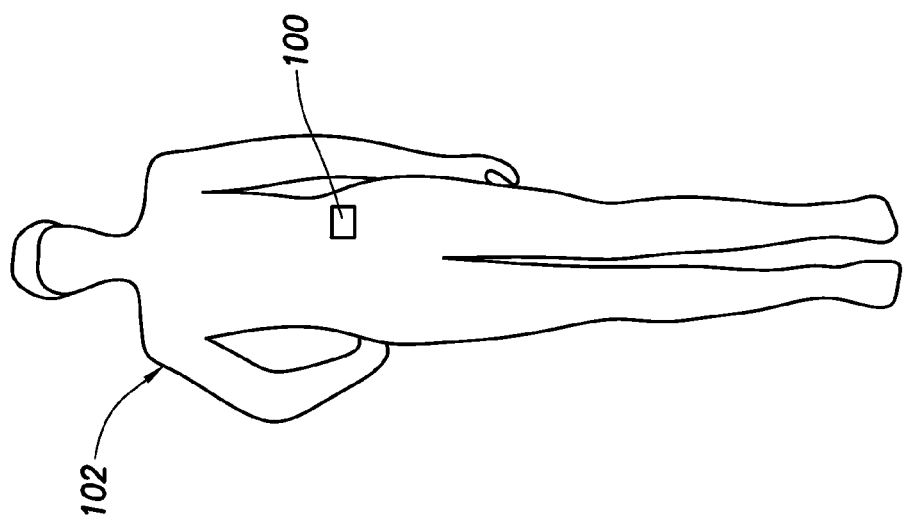
FIG. 1B
FIG. 1

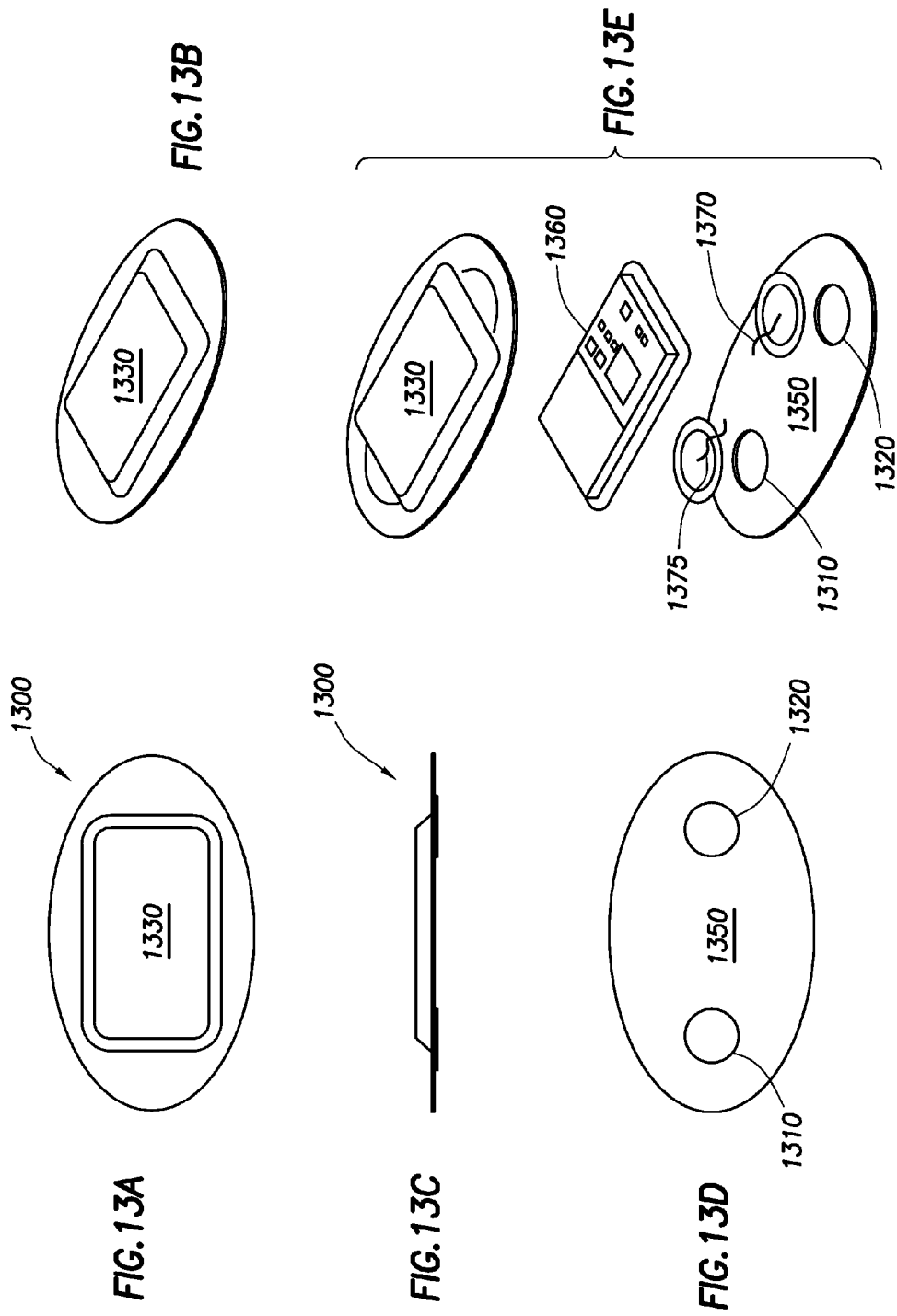

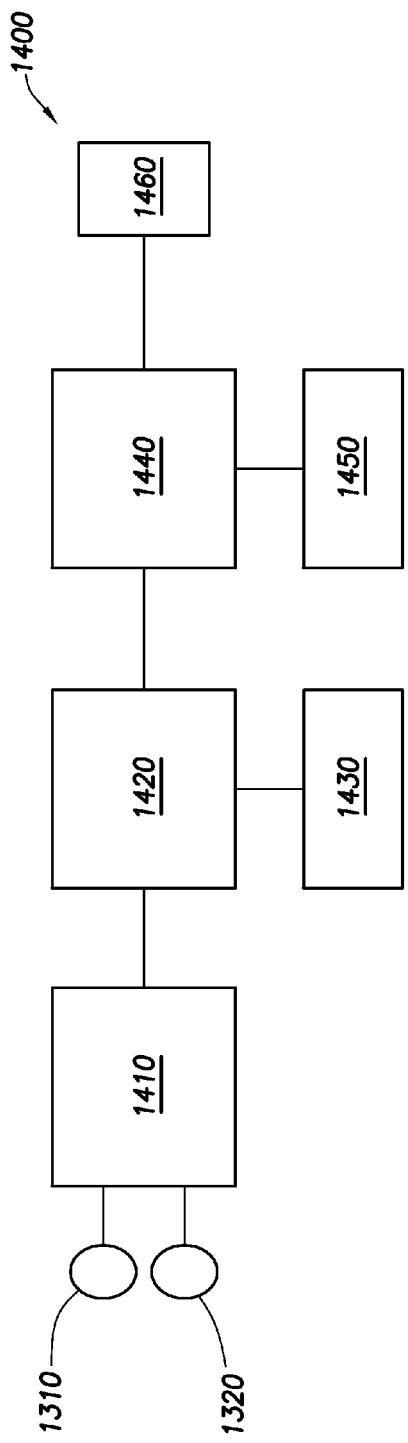
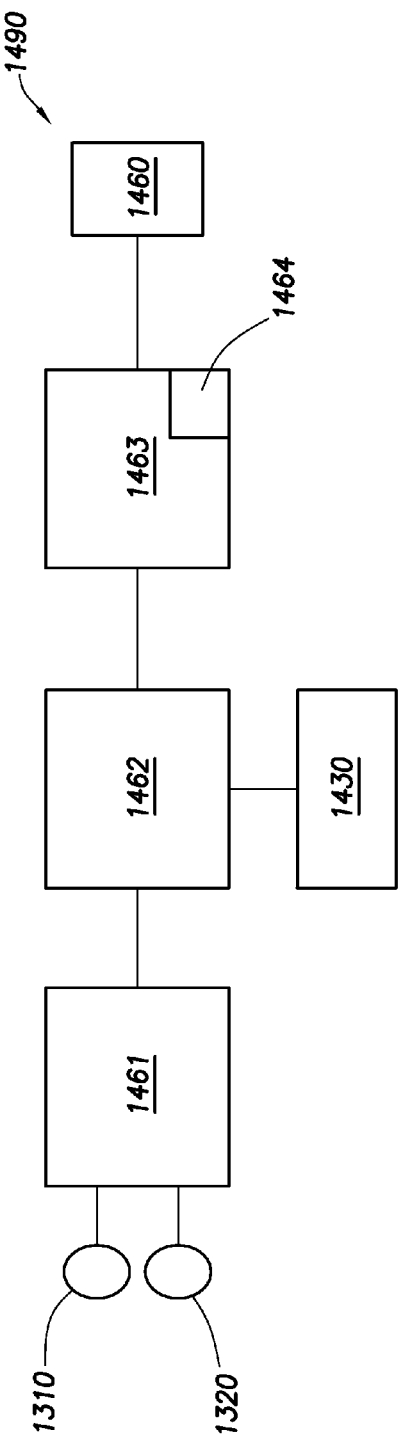

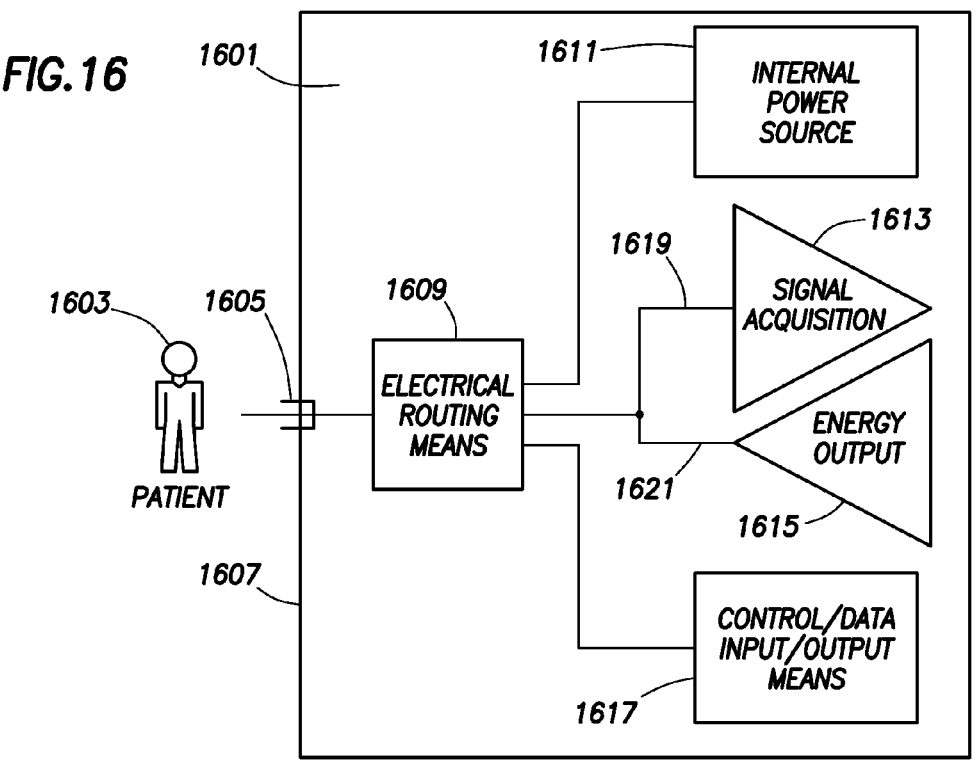
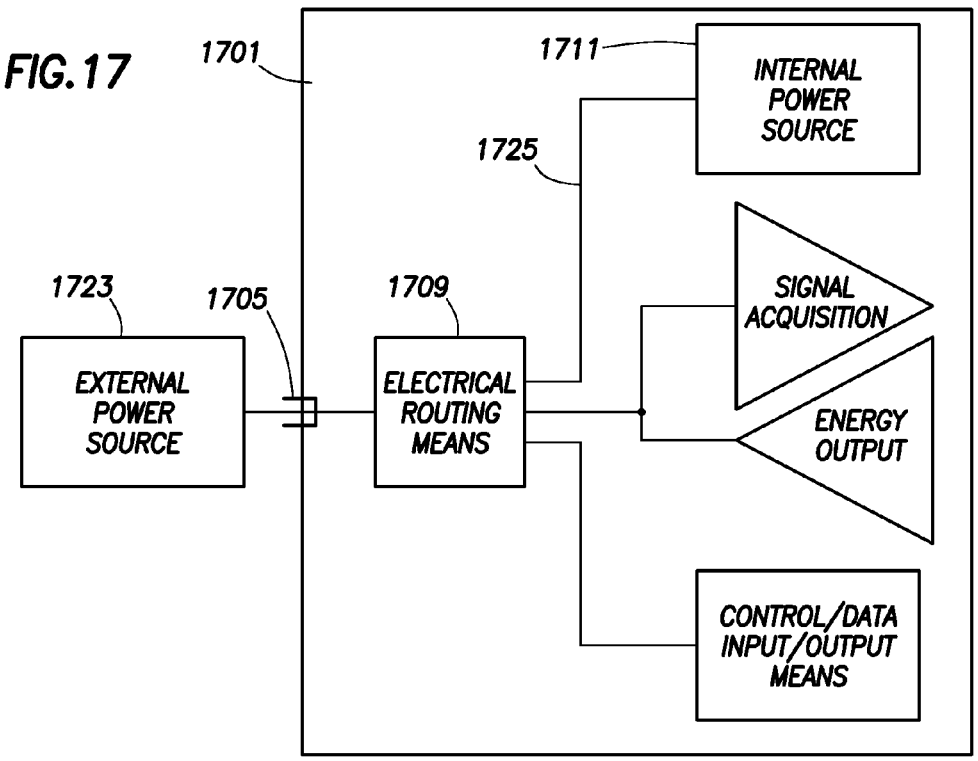

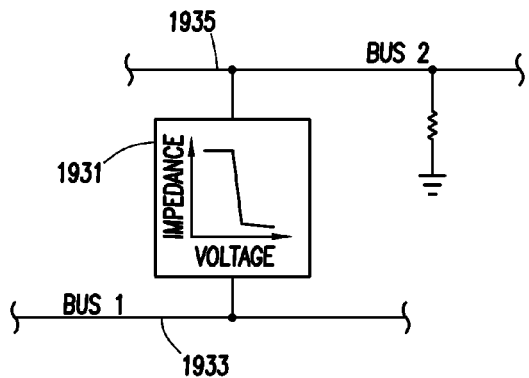
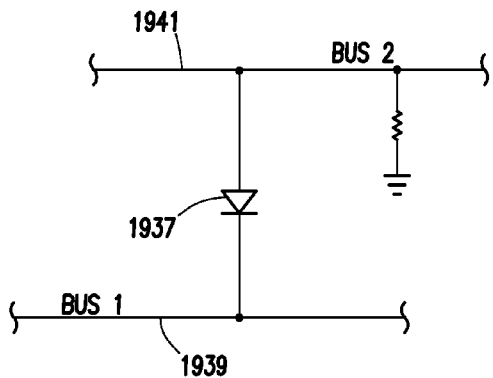
FIG.19A    FIG.19B
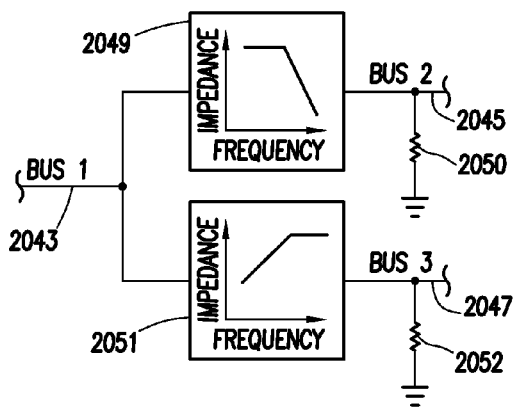
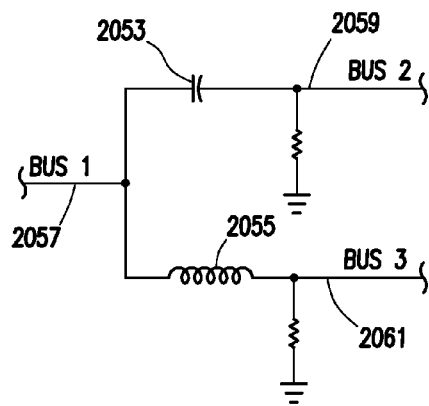
FIG.20A    FIG.20B
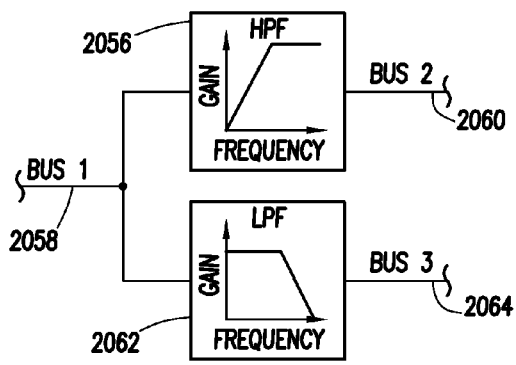
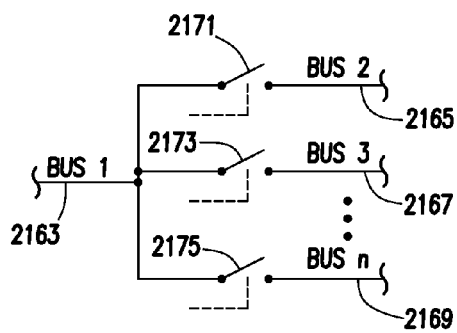
FIG.20C    FIG.21

BODY-ASSOCIATED RECEIVER AND METHOD

CROSS-REFERENCE TO RELATED APPLICATIONS

Pursuant to 35 U.S.C. §119 (e), this application claims priority to the filing date of U.S. Provisional Patent Application Ser. No. 61/122,723 filed on Dec. 15, 2008; U.S. Provisional Patent Application Ser. No. 61/160,289 filed on Mar. 13, 2009; U.S. Provisional Patent Application Ser. No. 61/240,571 filed on Sep. 8, 2009; and U.S. Provisional Patent Application Ser. No. 61/251,088 filed on Oct. 13, 2009, the disclosures of which applications are herein incorporated by reference. This application is also a continuation-in-part of U.S. patent application Ser. No. 11/912,475 filed on Apr. 28, 2006 and a continuation-in-part of U.S. patent application Ser. No. 12/324,798 filed on Nov. 26, 2008, the disclosures of which applications are herein incorporated by reference.

FIELD OF THE INVENTION

The present invention relates to receivers in a communication system and, more specifically, to receivers that detect data transmission encoded in current flow through a conducting solution with the ability to manage power and control dosage.

INTRODUCTION

There are many instances in both medical and non-medical applications where one desires to note a personal event, i.e., an event that is specific to a given individual. Examples of medical applications where one may wish to note an event that is specific to a given individual include, but are not limited to, the onset of one or more physiological parameters of interest, including disease symptoms, the administration of a medication, etc. Examples of non-medical applications where one desires to note an event that is specific to a given individual include, but are not limited to: the ingestion of certain types of foods (e.g., for individuals on controlled diets), the commencement of an exercise regimen, etc.

Because there are many instances where one wishes to note a personal event, a variety of different methods and technologies have been developed to make such notation possible. For example, log books and techniques have been developed in which individuals, e.g., patients and/or their health care provides, can record, e.g., by manually writing or data entry, time and date of an event. However, there continues to be a need for improvements in personal event monitoring. For example, manually logging when an event takes place can be time consuming and prone to error.

SUMMARY

Receivers, which may be external, implantable, semi-implantable, etc., are provided. Aspects of receivers of the invention include the presence of one or more of: a high power-low power module; an intermediary module; a power supply module configured to activate and deactivate one or more power supplies to a high power processing block; a serial peripheral interface bus connecting master and slave blocks; and a multi-purpose connector. Receivers of the invention may be configured to receive a conductively transmitted signal. Also provided are systems that include the receivers, as well as methods of using the same.

BRIEF DESCRIPTION OF THE FIGURES

FIG. 1 is a representation of a receiver for detection of data transmission through a living subject.

FIG. 1B is a block diagram representation of a power management module of the receiver of FIG. 1A in accordance with the teaching of the present invention.

FIGS. 13A to 13E provide various views of a two-electrode external signal receiver, according to one aspect.

FIGS. 14A to 14D provide block diagrams of hardware configurations that may be present in a signal receiver as shown in FIGS. 13A to 13E, according to one aspect.

FIG. 16 provides a block diagram showing a receiver connected to a patient.

FIG. 17 provides a block diagram showing a receiver connected to an external power charger.

FIGS. 19A-19B show a diagram of a router according to an aspect of the invention that discriminates a signal based on voltage level.

FIGS. 20A-20C show a diagram of a router according to an aspect of the invention that discriminates a signal based on frequency.

FIG. 21 shows a diagram of a router according to an aspect of the invention that discriminates a signal by employing active switches.

DETAILED DESCRIPTION

Figure 1A:
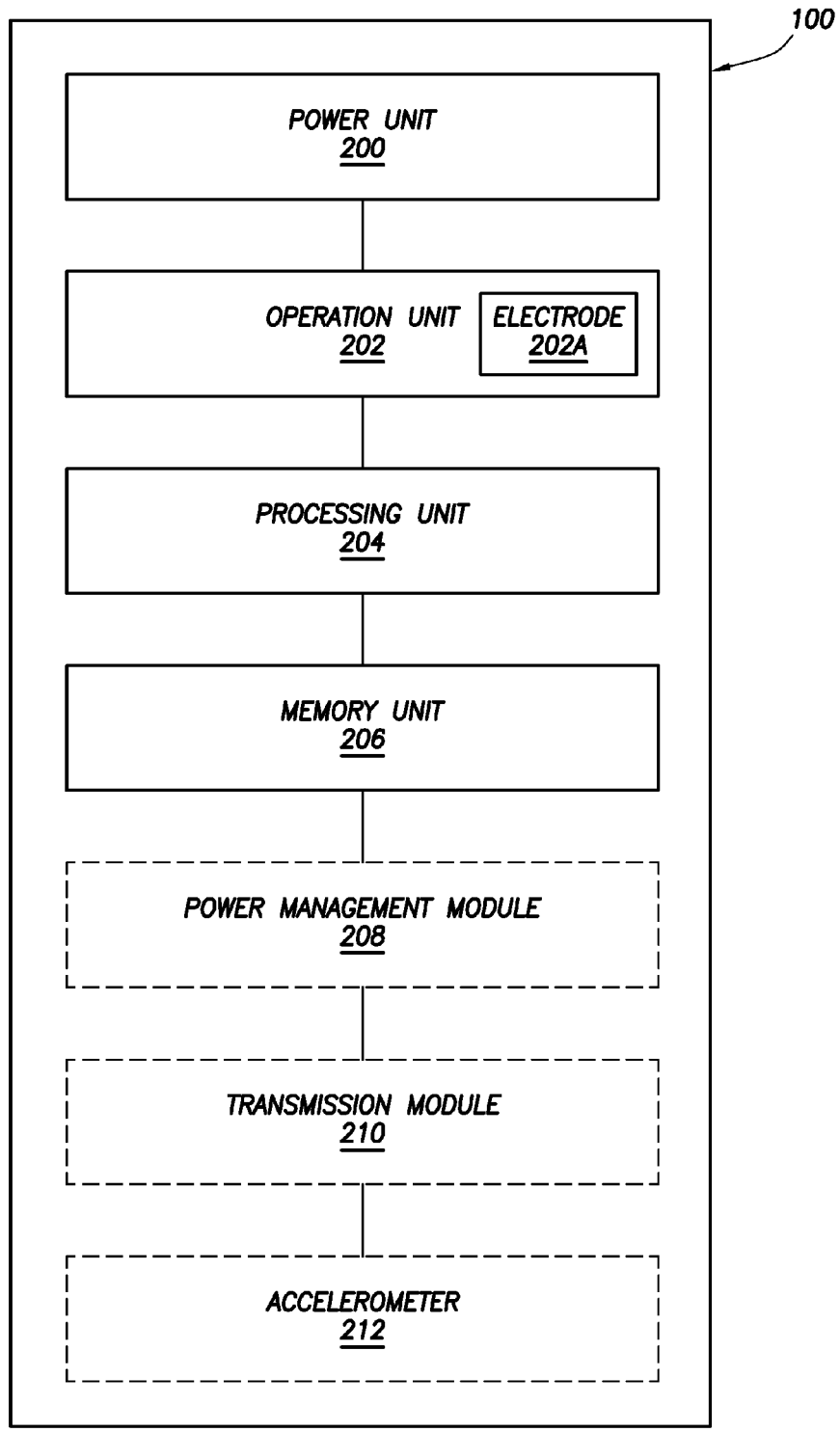
FIG. 1A is a block diagram representation of the receiver of FIG. 1 in accordance with the teachings of the present invention.

Receivers, which may be external or implantable, are provided. Aspects of receivers of the invention include the presence of one or more of: a high power-low power module; an intermediary module; a power supply module configured to activate and deactivate one or more power supplies to a high power processing block; a serial peripheral interface bus connecting master and slave blocks; and a multi-purpose connector. Receivers of the invention may be configured to receive a conductively transmitted signal. Also provided are systems that include the receivers, as well as methods of using the same.

Receivers of the present invention are electrical devices that include circuitry and logic present in housing, where the devices are configured to perform one or more medical functions. The term "medical" is used broadly to refer to any type of function that is performed in regard to the health of a living subject, such as a patient. As such, a device is considered to be medical device if it functions to receive data with respect to one or more parameters of a subject, whether the subject is in a healthy state or in a disease state. Parameters of interest include those described in greater detail below, such as physiologic parameters, signals from other medical devices, such as ingestible event marker (IEM) devices, etc. As such, medical devices of interest are those that may be used in therapeutic applications or non-therapeutic applications, e.g., as described in greater detail below.

In certain embodiments of the present invention, the receivers are devices that are sized to be stably associated with a living subject, e.g., patient, in a manner that does not substantially impact movement of the living subject and yet provides an intended function, such as signal receiving functionality, for extended periods of time. The term "patient" as used herein refers broadly to subjects suspected of or known to be suffering from a disease or abnormality, as well as subjects who are healthy. Receivers in accordance with the teaching of the invention may be associated with a patient's body by any convenient means, such as attaching the device to a patient's body or clothing, e.g., with tape, or by use of a clip, loop, or belt. Alternatively, the device may be placed in a compartment of clothing worn by the patient, such as the patient's pocket. Where desired, the device may be configured to be continuously associated with the patient for an extended period of time, e.g., minutes to months. In one example, the device may be configured to be continually associated with the patient for one week or more. In some instances, the devices are configured to be associated directly with a topical skin site of a subject. In yet other aspects, the devices are configured to be implantable. As the devices are sized to be stably associated with a living subject in a manner that does not substantially impact movement of the living subject, aspects of the devices have dimensions that, when employed with a subject, such as a human subject, will not cause the subject to experience any difference in its ability to move. As such, in these aspects, the device is dimensioned such that its size and shape do not hinder the ability of the subject to physically move. Devices of the invention may have a size that provides for functionality when applied to a topical body location, for example as described above. In such instances, the devices may have a total volume of 50 cm3 or less, such as 30 cm3 or less, including 25 cm3 or less, such as 20 cm3 or less. In certain aspects, the device has a small size, where in certain aspects, the device occupies a volume of space of about 5 cm3 or less, such as about 3 cm3 or less, including about 1 cm3 or less. Devices of the invention may have a longest dimension that is 30 cm or less, such as 20 cm or less, including 15 cm or less.

Despite the small size of the receivers, the devices can operate for extended time periods. As such, the receivers may operate for periods of one week or longer, such as two weeks or longer, including one month or longer, three months or longer, six months or longer, including twelve months or longer. To provide for this operation over extended time periods and in view of the small size of the receivers, the devices are configured for low power consumption. By low power consumption is meant that the average power consumption of the device for a 24 hour period is mA or less, such as 100 μA or less, and including 10 μA or less. The average current draw of the receiver when present in an idle mode (described in greater detail below) is 100 μA or less, such as 10 μA or less and including μA or less. The average current draw of the receiver when present in a storage mode (described in greater detail below) is 10 μA or less, such as 1 μA or less and including 0.1 μA or less. In some instances, the current draw of the receiver when present in an active state (as described in greater detail below) ranges from 3 μA to 30 mA, such as from 30 μA to 3 mA, and including from 30 μA to 300 μA.

In certain aspects, the receivers of the invention are signal receivers. Signal receivers are devices that are configured to receive a signal from another device, such as a trans-body conductively transmitted signal (reviewed in greater detail below). Where the receivers are signal receivers, the receivers may be configured to receive an ingestible event marker emitted signal, as described in greater detail below.

Receivers of the invention may include a variety of different modules which are configured, e.g., via hardware and/or software implementation, to perform one or more functions of the device. Modules are made up of one or more functional blocks which act in concert to perform a particular function, which is the purpose of the module. A given module may be implemented as hardware, software or a combination thereof. Modules that may be present in receivers of the invention are now reviewed in greater detail below.

Aspects of the devices include a high power-low power module. High power-low power modules are modules that include high power functional block and a low power functional block. By low power functional block is meant a functional block that performs processing and requires low current draw and power consumption. The low power functional block performs at least one discrete function—e.g., a function requiring non-high performance processing, where examples of such functions include maintaining an idle state, monitoring a bus, awaiting an occurrence of a signal, such as an interrupt signal, etc. Of interest as low power functional blocks are functional blocks that draw a current of 10 μA or less and including 1 μA or less. By high power functional block is meant a functional block that performs higher performance processing requiring larger current draw and power consumption than the low power functional block. The high power functional block performs at least one discrete function, such as processing conductively transmitted signals, processing received physiological data, etc. The larger computational processing may involve, for example, executing digital signal processing algorithms (such as, Finite Impulse Response (FIR) filters, Fast Fourier transforms (FFTs), etc.). Examples of high power functional blocks are functional blocks that draw a current of 30 μA or more, such as 50 μA or more in order to perform their designated functions.

The low and high power functional blocks may be implemented in a variety of different ways. For example, the low and high power functional blocks may be implemented on separate processors or may be implemented as separate circuit elements of a system on chip (SOC) structure, among other configurations. Further details regarding hardware implementations of interest are provided below. Receivers of interest include at least one low power functional block and at least one high power functional block. In some instances, the receivers will include additional low and/or high power functional blocks, as desired to implement a particular receiver.

Receivers of the invention may also include an intermediary module which is configured to cycle the high power functional block between active and inactive states. By active state is meant a state in which the functional block is performing its designated function or functions, such as demodulating and/or processing a received signal, processing physiological data, etc. By inactive state is meant a state in which the functional block is not performing its designated function or functions, where the inactive state may be an idle or sleep state, e.g., where the functional block draws minimal current (such as 1 μA or less, including 0.1 μA or less) or an off state, where the functional block draws no current. By "cycle" is meant that the intermediary module transitions the high power functional block between active and inactive states. In other words, the intermediary module changes the state of the functional block from active to inactive, or vice versa. The intermediary module may cycle the high power functional block between an active and inactive state according to different inputs, such as a predetermined schedule (for example as providing by programming of the receiver) or an applied stimulus. In some instances, the intermediary module may cycle the high power functional block between active and inactive states according to a predetermined schedule. For example, the intermediary module may cycle the high power functional block between active and inactive states every 20 sec, such as every 10 sec, and including every 5 sec. In some instances, the intermediary module may cycle the high power functional block between active and inactive states according to an applied stimulus, such as receipt of a conductively transmitted signal, in response to one or more predetermined physiological parameters, in response to user instructions (for example as implemented by depressing an operational button on the receiver or sending a command signal to the receiver) etc.

The receiver may be configured to have various states—e.g., an idle state or one or more active states. Accordingly, the intermediary module may cycle the high power functional block between an active and inactive state as needed, depending on the desired function at a given time of the device. In the active state, the receiver is performing one or more active functions, such as receiving a signal, processing a signal, transmitting a signal, obtaining physiological data, processing physiological data, etc. In an idle state, the receiver draws minimal current, for example as described above. In the idle state, the receiver may perform minimal functions in order to minimize current draw, such as maintain configurations, maintain sleep modes, etc. However, in the idle state the receiver does not perform functions that require more than the minimal current draw. The intermediary module may cycle the receiver between active and idle states according to different inputs, such as a predetermined schedule (for example as provided by receiver programming) or applied stimulus, such as described above.

Receivers of interest may be configured to perform a transbody conductive signal (such as an IEM or smart parenteral device signal) detection protocol. Such devices may be viewed as signal receivers. Transbody conductive signal detection protocols are processes in which the signal receiver is in a state in which it can receive a signal emitted by an IEM or smart parenteral device, and process the signal as desired, e.g., by performing one or more tasks, such as decoding the signal, storing the signal, time-stamping the signal, and retransmitting the signal, as described in greater detail below.

Receivers of interest, such as signal receivers, may also be configured to perform a physiological data detection protocol when present in an active state, e.g., to obtain ECG data, accelerometer data, temperature data, etc., as described in greater detail below.

Referring now to FIGS. 1, 1A, and 1B illustrate one embodiment of a receiver of the present invention. The receiver 100 is shown in position on a living subject 102. The receiver 100 is shown attached to a left mid-section of the subject 102. However, the scope of the present invention is not limited by the location of the receiver 100 on the subject 102.

Referring now to FIG. 1A, the receiver 100 includes a power unit or power source 200, an operation unit 202 that includes an electrode 202A, an operation or processing unit 204, and a memory unit 206. The receiver 100 also includes a power management module 208 that controls the power consumption. The receiver 100 is capable of communicating with other near-by devices using a transmission module 210. Furthermore, the receiver 100 may include various features such as an accelerometer for detection of the orientation of the receiver 100. In instances where the subject is laying down or in a horizontal position, the receiver 100 is capable of detecting that position and the duration of time that the subject remains in that position.

Additionally, the receiver 100 may further include one or more distinct physiological parameter sensing abilities. By physiological parameter sensing ability is meant a capability of sensing a physiological parameter or biomarker, such as, but not limited to: heart rate, respiration rate, temperature, pressure, chemical composition of fluid, e.g., analyte detection in blood, fluid state, blood flow rate, accelerometer motion data, IEGM (intra cardiac electrogram) data, etc.

Accordingly, the receiver 100 may include physiological parameter measuring tools that allows it to determine if the subject is simply laying down or if the subject has suffered some medical condition that has caused them to end-up in that position. For example, the subject may have had a heart attack and the receiver 100 can detect that condition and in conjunction with information from the accelerometer 212, the receiver 100 is able to determine that the patient has a potentially serious medical condition. Another example would include the instant where the subject suffers from an epileptic seizure. The accelerometer 212 would provide information to the receiver 100 and the information from the accelerometer 212 combined with the measured physiological parameters would allow the receiver 100 to determine that a medical condition is taking place that will require immediate attention.

Referring now to FIG. 1B, the power management module 208 includes a high power operation module 300, an intermediate power operation module 302, and a low power operation module 304. The power management module 208 controls the power supplied to the components of the receiver 100 through the beacon switching module 306. The beacon switching module 306 generates a signal that allows the power management module 208 to transition the state of the receiver from active to active non-operation to inactive state depending on the information provided by the various modules and unit of the receiver 100.

As discussed above, in the embodiment set forth in FIG. 1, the receiver 100 may move from one state to another depending on the information provided by the environment. At an idle or inactive state the receiver 100 is not performing any active function and remains idle. The receiver 100 may transition between inactive state and other states depending on the required function(s) to be performed. Depending on the function, the intermediate power operation module may cycle the receiver 100 between the inactive state (e.g., idle) and the active state. For example, when the receiver 100 transitions from inactive state to detecting or active non-operational in order to collect ECG and/or accelerometer data, the intermediary module cycles the receiver 100 from an inactive (such as idle) state to an active state. When the receiver 100 is done collecting the ECG and accelerometer data, the intermediary module cycles the receiver 100 back to an inactive (such as idle state), and the receiver 100 returns to inactive state.

When the receiver 100 transitions from inactive state to a sniff state for active non-operational condition in order to scan for data transmission signals (for examples by using a sniff module, such as described in greater detail below) associated with ionic emission for producing current flow with the data transmission encoded as a part thereof or for detection of data transmission associated with wireless communication, the intermediary module cycles the receiver 100 from an inactive (such as idle) state to an active non-operational state. If the receiver 100 receives a signal during this scanning or sniffing period, the receiver 100 then goes to active operational state and the high power operation module 300 of FIG. 1B supplies high power to the operation unit 202, the processing unit 204, and the memory unit 206 all of FIG. 1A. Then the receiver 100 processes the signal, e.g., demodulates, time-stamps and stores the signal as described in greater detail below, at the active operational state. When the receiver 100 completes processing the signal, the power management module 208 cycles the receiver 100 back to the inactive (such as idle state), and the receiver 100 returns to the inactive state.

In some aspects, scanning for data transmission signals from a communication module within the subject 102 of FIG. 1, such as the active non-operation state 130, the receiver 100 does not require high power to be cycled to the active non-operational state. In such cases the high power demand is not needed until a signal is detected for demodulation and decoding.

In accordance with the teaching of the present invention, the signal receiver aspects of the receiver 100 may be configured to receive a conductively transmitted signal. The conductively transmitted signal may be a signal that is conductively transmitted signal by any physiologic part of the body or from a device that conductively transmits a signal through a body using ionic emission through controlled release of mass from solid into a conducting solution or fluid. The signal may be produced by an ionic emission module or an ingestible event marker (IEM) or a smart-parenteral delivery system. Ingestible event markers of interest include those described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753 published as WO 2009/042812; the disclosures of which applications are herein incorporated by reference. Smart parenteral delivery systems are described in PCT application serial no. PCT/US2007/015547 published as WO 2008/008281; each of the foregoing disclosures is herein incorporated by reference in its entirety.

As the receiver of these aspects is configured to receive data encoded in current flow through a conductive fluid, the receiver and the device that emits the signal (such as an IEM) use the living body with which they are associated as a communication medium. To employ the body as a communication medium for the signal, the body fluids act as the conducting fluid and the body of the patient is used as a conduction medium for communication. As such, the signal that is transferred between an ionic emission device and any other signal emitting device and the receiver, such as the receiver 100 of FIG. 1, travels through the body of the subject 102. The conductively transmitted signal of interest may be transmitted through and received from the skin and other body tissues of the subject body in the form of electrical alternating current (a.c.) signals that are conducted through the body tissues. As a result, such receivers do not require any additional cable or hard wire connection between the device emitting the signal and the receiver.

As the signal receivers are configured to receive a conductively transmitted signal, they may include a transbody conductive communication module. The transbody conductive communication module is a functional module that is configured to receive a conductively transmitted signal, such as a signal emitted by an IEM. Where desired, the transbody conductive communication module may be implemented by a high power functional block, such as described above. In some instances, the signal which the transbody conductive communication module is configured to receive is an encoded signal, by which is meant that the signal has been modulated in some manner (for example using a protocol such as binary phase shift keying (BPSK), frequency shift keying (FSK), amplitude shift keying (ASK), etc.). In such instances, the receivers and transbody conductive communication module thereof are configured to decode a received encoded signal, such as a signal emitted by an ingestible event marker. The receivers may be configured to decode the encoded signal in a low signal to noise ratio (SNR) environment, e.g., where there may be substantial noise in addition to the signal of interest, e.g., an environment having an SNR of 7.7 dB or less. The receivers may be further configured to decode the encoded signal with substantially no error. In certain aspects, the signal receiver has a high coding gain, e.g., a coding gain ranging from 6 dB to 12 dB, such as a coding gain ranging from 8 dB to 10 dB, including a coding gain of 9 dB. The signal receivers of aspects of the invention can decode encoded signals with substantially no error, e.g., with 10% error or less.

In those aspects where the received signal is encoded, such as where the received signal is an encoded IEM signal, the transbody conductive communication module may be configured to process the received signal with at least one demodulation protocol, where the transbody conductive communication module may be configured to process the received signal with two or more, three or more, four or more, etc., different demodulation protocols, as desired. When two or more different demodulation protocols are employed to process a given encoded signal, the protocols may be run simultaneously or sequentially, as desired. The received signal may be processed using any convenient demodulation protocol. Demodulation protocols of interest include, but are not limited to: Costas Loop demodulation (for example, as described in PCT Application Serial No. PCT/US07/024,225 and published as WO 2008/063626, the disclosure of which is herein incorporated by reference); coherent demodulation (for example, as described in PCT Application Serial No. PCT/US07/024,225 and published as WO 2008/063626, the disclosure of which is herein incorporated by reference); accurate, low overhead iterative demodulation (for example, as described in PCT Application Serial No. PCT/US07/024,225 and published as WO 2008/063626, the disclosure of which is herein incorporated by reference); incoherent demodulation; and differential coherent demodulation.

In some instances, a coherent demodulation protocol is employed. Coherent demodulation modules that may be employed in aspects of the receivers include, but are not limited to, those described in PCT Application Serial No. PCT/US2007/024225; the disclosure of which is herein incorporated by reference.

In some instances, a differential coherent demodulation protocol is employed. Differentially coherent demodulation compares the phase of adjacent bits in a Binary phase-shift keying modulated signal (BPSK). For example an 8 bit binary code of 11001010 would result in a differential signal of 0101111. Since the technique leverages phase differences between adjacent bits, it is inherently more robust against signal frequency instability and drift than a coherent demodulation scheme.

Coherent Demodulation

The demodulation of BPSK in the presence of AWGN (Additive White Gaussian Noise) is performed in certain embodiments to minimize BER (Bit Error Rate) using coherent demodulation.

In these embodiments, the in vivo transmitter facilitates the receiver coherent demodulation process by sending a pilot carrier in the "front porch" of each burst of BPSK modulation. This protocol provides a stable carrier at full amplitude and a reference phase that corresponds with the transmission of a 0 bit. The presence of a front porch gives a useful detection signature to the receiver and a large number of carrier cycles for accurate estimation of the carrier frequency and phase.

An additional practical use is made of the carrier frequency to simplify derivation of the data rate. The transmitted signal is formatted to have the data clock frequency an integer division of the carrier frequency. This permits easy and rapid data clock acquisition once the carrier acquisition has been accomplished.

The receiver samples the incoming signal at a rate of around 4 times the carrier frequency in certain embodiments. This signal is mixed with a DDS (Direct Digital Synthesizer) set to the nominal carrier frequency to create complex baseband (real and imaginary components). The output of the mixer is low pass filtered and decimated. The low pass filter bandwidth must be sufficiently wide to capture frequencies in the band due to carrier oscillator uncertainty and frequency hopping dither. The frequency of the BPSK is subsequently in the vicinity of 0 Hz with a frequency accuracy of +/−20%.

The receiver squares the complex baseband BPSK signal to create a strong double frequency line. The front porch signal and following BPSK modulation all contribute to this line. The squared complex time domain signal is transformed to the frequency domain using an FFT (Fast Fourier Transform). The peak energy bin is identified as the 2× carrier frequency. This frequency is divided by two to provide an estimate of the carrier offset frequency to about 0.1% accuracy using a 1024 point FFT.

The complex baseband signal is then mixed a second time with the determined offset frequency. The result after narrow band low pass filtering is a complex BPSK signal centered at 0 Hz with an accuracy of 0.1%. The bandwidth of the narrow band low pass filter corresponds with the half bandwidth of the BPSK signal.

The front porch signal is then extracted. The frequency offset is determined by first computing the phase (phi=arctan (imag/real)) of all sample points in the front porch, and then estimating the slope of phi vs. time using a least mean square fit to a line. The slope of the line corresponds to the residual frequency offset. The complex baseband signal is then mixed a third time to remove this frequency offset with an accuracy better than 0.01%.

The complex signal front porch is then averaged to determine the mean imaginary and real values. The arctan(mean imag/mean real) provides the front porch phase. A rotator factor is computed based on this phase to rotate the BPSK on to the imaginary axis with the front porch at 270 degrees.

A second averaging is then performed on the entire rotated BPSK signal to identify the center of gravity of the 90 degree (data=1) and the BPSK is rotated in a similar manner to center this on the imaginary axis. The imaginary signal is then sliced to extract the data.

The sliced data is strobed with a data clock that is derived from the prior determination of the carrier frequency and apriori knowledge of the integer factor relating the carrier frequency to the data clock frequency.

In embodiments of the above protocols, it is assumed that the carrier frequency holds to a sufficient accuracy in frequency and phase through the duration of the entire burst.

Aspects of Coherent Demodulation modules that may be employed in embodiments of the receivers include, but are not limited to, those described in PCT Application Serial No. PCT/US2007/024225; the disclosure of which is herein incorporated by reference.

Accurate, Low Overhead Iterative Decoding

In certain embodiments, the receivers include an accurate, low overhead interactive decoder, also referred to herein as a communications decoder. The communications decoder provides highly accurate communications in a simple, elegant, and cost-effective manner despite the presence of significant signal distortion due to noise and other factors. The communications decoder utilizes error correcting codes and a simple, iterative process to achieve the decoding results. The communications decoder can be used across multiple and varied applications to realize a low cost, high coding gain.

Broadly, an embodiment of a communications decoder provides decoding capabilities for data communications. An embodiment of a communications decoder provides a high coding gain with minimal overhead. In some instances, the communications decoder facilitates data transmission rates close to the theoretical maximum, the Shannon Limit, while minimizing processing overhead. The low overhead ensures cost-effective implementations. Various implementations of the present invention include hardware, software, and circuitry.

Various embodiments of the inventive communications decoder of the present invention use error correcting codes and a simple, unique process to "urge" a measurement signal associated with a bit in error toward a measurement signal associated with the correct, original bit, thus improving the likelihood of identifying destination data that matches the data encoded at origin and significantly improving data accuracy at destination. The simple, unique process facilitates efficient implementations. The low overhead associated with the simple, unique process minimizes costs. LDPC decoding is far less complex by using the iterative communications decoder of the present invention.

Generally, the decoder module generates the decoded data via variations of the following technique. For each bit set of the encoded data, a set of measured signals associated with the encoded data are rounded to the nearest most likely possible measurement if no noise were present, e.g., to a nearest transmission symbol. The set of transmission symbols is converted into a set of hard code decision values. An error check is performed on the set of hard code decision values. The set of measured signals is adjusted based on an outcome of the error check of the set of hard code decision values. The foregoing is performed in passes across all measured signal sets of the encoded data until a predetermined stopping condition is met. Aspects of Accurate, Low Overhead Iterative Decoding modules that may be employed in embodiments of the receivers include, but are not limited to, those described in PCT Application Serial No. PCT/US2007/024225; the disclosure of which is herein incorporated by reference.

Forward Error Correction

In certain embodiments, the receiver is configured for use with an in vivo transmitter that employs FEC (Forward Error Correction) to provide additional gain to combat interference from other unwanted signals and noise. The error correction is simple in the transmitter and receiver, and provides high coding gain. This functionality is achieved using single parity check product codes and a novel SISO (Soft In Soft Out) iterative decoding algorithm.

The transmitter encodes the message by arranging it in rows and columns. Each row has an appended parity bit, and similarly each column has an appended parity bit. For example, a 100 bit message could be arranged in a 10 by 10 bit array. Parity bits would be added to create a final 11 by 11 bit array that would then be transmitted on the channel using BPSK. For additional gain, additional dimensions could be used, such as three if a cube were created to arrange the message and parity bits.

The receiver decodes the message by an iterative process to achieve high coding gain. Each bit is sampled and saved in "soft" form. Assuming ideal samples (i.e., hard decision points) are normalized to −1 and +1, received bits would come in a range between say, −2.0 and +2.0. A hard decision is made on all samples and parity checked. If a row or column has a parity error, the samples of that row or column are repulsed from their corresponding hard decision point by a small delta. If the row or column has no parity error, the samples of that row or column are attracted to their corresponding hard decision point by a small delta. Using a properly selected delta, based on expected channel SNR (Signal to Noise Ratio), ten iterations is usually sufficient to achieve an 8 to 10 dB coding gain on AWGN (Additive White Gaussian Noise). This method is easy to implement in stored program DSP or FPGA/ASIC logic. It also comes within one or two dB of the Shannon limit for forward error correction given the particular coding rate.

Aspects of Forward Error Correction modules that may be employed in embodiments of the receivers include, but are not limited to, those described in PCT Application Serial No. PCT/US2007/024225 published as WO 2008/063626; the disclosure of which is herein incorporated by reference.

Beacon Functionality Module

Various aspects may employ the beacon functionality module. In various aspects, the beacon functionality sub-module may employ one or more of the following: a beacon wakeup module, a beacon signal module, a wave/frequency module, a multiple frequency module, and a modulated signal module.

The beacon functionality module may be associated with beacon communications, e.g., a beacon communication channel, a beacon protocol, etc. For the purpose of the present disclosure, beacons are typically signals sent either as part of a message or to augment a message (sometimes referred to herein as "beacon signals"). The beacons may have well-defined characteristics, such as frequency. Beacons may be detected readily in noisy environments and may be used for a trigger to a sniff circuit, such as those described above.

In one aspect, the beacon functionality module may comprise the beacon wakeup module, having wakeup functionality. Wakeup functionality generally comprises the functionality to operate in high power modes only during specific times, e.g., short periods for specific purposes, e.g., to receive a signal, etc. An important consideration on a receiver portion of a system is that it be of low power. This feature may be advantageous in an implanted receiver, to provide for both small size and to preserve a long-functioning electrical supply from a battery. The beacon wakeup module may enable these advantages by having the receiver operate in a high power mode for very limited periods of time. Short duty cycles of this kind can provide optimal system size and energy draw features.

In practice, the receiver may "wake up" periodically, and at low energy consumption, to perform a "sniff function" via, for example, a sniff circuit. For the purpose of the present application, the term "sniff function" generally refers to a short, low-power function to determine if a transmitter is present. If a transmitter signal is detected by the sniff function, the device may transition to a higher power communication decode mode. If a transmitter signal is not present, the receiver may return, e.g., immediately return, to sleep mode. In this manner, energy is conserved during relatively long periods when a transmitter signal is not present, while high-power capabilities remain available for efficient decode mode operations during the relatively few periods when a transmit signal is present.

Several modes, and combination thereof, may be available for operating the sniff circuit. By matching the needs of a particular system to the sniff circuit configuration, an optimized system may be achieved.

Further examples of beacon functionality modules are described in PCT Application Serial No. PCT/US08/85048; the disclosure of which is herein incorporated by reference.

Frequency Hopping Functionality Module

Various aspects may employ frequency hopping functionality module. The frequency hopping functionality module may be associated with the specific communications channel(s), frequency hopping protocol, etc. As such, various aspects may utilize one or more frequency hopping protocols. For example, the receiver may search the designated range of frequencies, e.g., two or more different frequencies, in which the transmission could fall. When a single proper decode is achieved, the in vivo transmitter has accomplished its mission of communicating its digital information payload to the receiver.

In some instances, a transmitted frequency uncertainty provided by random frequency hopping, e.g., via a random module, may create multiple benefits. One example of such a communication protocol is frequency hopping spread spectrum communication (FHSS). FHSS is a method of transmitting radio signals by rapidly switching a carrier among many frequency channels, using a pseudorandom sequence known to both the transmitter and the receiver. One such benefit, for example, may be easy implementation on a small die. To illustrate, the in vivo transmitter carrier frequency oscillator can be an inaccurate free running oscillator that is easily implemented on a small portion of a 1 mm die. Accuracies on the order of +/−20 are easily tolerated. This is because the receiver employs frequency searching algorithms.

Another such benefit may be extended battery life. To illustrate, over the course of the transmitter battery life, e.g., three to ten minutes, the probability of the transmitter transmitting on a clear channel that can be received by the frequency agile receiver may be significantly enhanced due to random frequency hopping.

Still another benefit may be minimized collision events in high volume environments. To illustrate, minimization of collision probability when multiple in vivo transmitters, e.g., ingestible event markers, are potentially transmitting simultaneously, such as in instances where the multiple ingestible event markers are ingested concurrently or in close temporal proximity. Stated differently, without frequency hopping functionality, there may be a high probability that ingestible event markers of a similar lot will transmit on the same (or nearly the same) frequency, resulting in multiple collisions.

In certain aspects, the useful frequency spectrum for use in volume conduction applications ranges from about 3 kHz to 150 kHz. Through detailed animal studies it has been observed that in some environments, the in vivo transmitter, supra, having a received signal level in the range of 1 to 100 $\mu V$ may compete with narrow band interfering signals on the order of hundreds to thousands of $\mu V$ in the same frequency spectrum. To mitigate the destructive nature of interfering signals, a frequency hopping channel or protocol may be employed in which the in vivo transmitter randomly frequency hops a narrow band transmitted signal, e.g., a modulated signal such as a binary phase shift keying (BPSK) signal or FSK signal, output on each transmission.

Further examples of Frequency Hopping modules are described in PCT Application Serial No. PCT/US08/85048; the disclosure of which is herein incorporated by reference.

Collision Avoidance Functionality Module

Various aspects may employ a collision avoidance functionality module. The collision avoidance functionality module may be associated with the specific communications channel(s), collision avoidance protocols, etc. As such, various aspects may utilize various collision avoidance protocol techniques associated with the specific communications channel(s). Collision avoidance techniques may be particularly useful, for example, in environments where two or more in vivo transmitters are present, e.g., where an individual ingests multiple IEMs. In such an environment, if the various in vivo transmitters send their signals continuously, the transmission of one may obscure the transmission from all the other in vivo transmitters. As a result, failure to detect signals may increase significantly.

Various aspects may include various collision avoidance approaches, alone or in various combinations.

One such approach employs multiple transmit frequencies. By using frequency-selective filtering, the transmitter broadcasting at f1 can be distinguished from the transmitter broadcasting at f2, even if they are transmitting simultaneously.

Further examples of Collision Avoidance modules are described in PCT Application Serial No. PCT/US08/85048; the disclosure of which is herein incorporated by reference.

Physiological Sensing

In addition to receiving a conductively transmitted signal, such as one emitted by an identifier of an ingestible event marker, the signal receiver may further include one or more distinct physiological parameter sensing abilities. By physiological parameter sensing ability is meant a capability of sensing a physiological parameter or biomarker, such as, but not limited to: cardio-data, including heart rate, electrocardiogram (ECG), and the like; respiration rate, temperature; pressure; chemical composition of fluid, e.g., analyte detection in blood, fluid state, blood flow rate, accelerometer motion data, etc. Where the signal receiver has physiological parameter or biomarker sensing capability, the number of distinct parameters or biomarkers that the signal receiver may sense may vary, e.g., 1 or more, 2 or more, 3 or more, 4 or more, 5 or more, 10 or more, etc. The term "biomarker" refers to an anatomic, physiologic, biochemical, or molecular parameter associated with the presence and severity of specific disease states. Biomarkers are detectable and measurable by a variety of methods including physical examination, laboratory assays and medical imaging. Depending on the particular embodiment, the signal receiver may accomplish one or more of these sensing functions using the signal receiving element, e.g., using electrodes of the receiver for signal receiving and sensing applications, or the signal receiver may include one or more distinct sensing elements that are different from the signal receiving element. The number of distinct sensing elements that may be present on (or at least coupled to) the signal receiver may vary, and may be 1 or more, 2 or more, 3 or more, 4 or more, 5 or more, 10 or more, etc.

In certain embodiments, the signal receiver includes a set of 2 or more, such as 2 or 3, electrodes that provide for dual functions of signal receiving and sensing. For example, in addition to receiving signal, the electrodes can also serve additional sensing functions. In certain embodiments, the electrodes are used to generate electrocardiogram data. From that data, there are many kinds of processing that can be done, e.g., to detect various cardiac events, such as tachycardia, fibrillations, heart rate, etc. The obtained electrocardiogram data can be used to titrate medications, or be used for alerts when an important change or significant abnormality in the heart rate or rhythm is detected. This data is also helpful in certain embodiments for monitoring heart rate in patients who do not have pacemakers or as an alternative to patients who might normally require a Holter monitor or a Cardiac Event Monitor, portable devices for continuously monitoring the electrical activity of the heart for 24 hours or other devices. An extended recording period is useful for observing occasional cardiac arrhythmias that are difficult to identify in shorter time periods.

Figure 2:
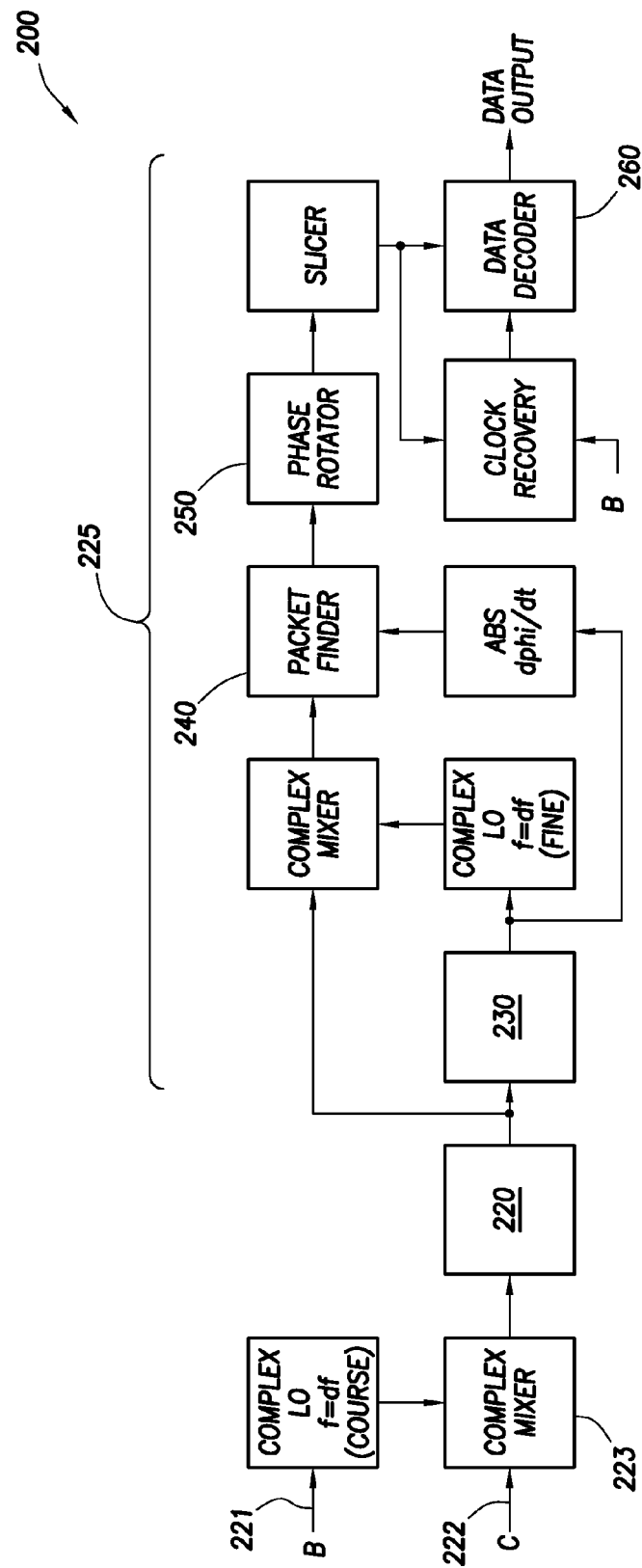
FIG. 2 is a functional block diagram of a demodulation circuit that performs coherent demodulation that may be present in a receiver, according to one aspect.

As described above, two or more different demodulation protocols may be employed to decode a given received signal. In some instances, both a coherent demodulation protocol and a differential coherent demodulation protocol may be employed. FIG. 2 provides a functional block diagram of how a receiver may implement a coherent demodulation protocol, according to one aspect of the invention. It should be noted that only a portion of the receiver is shown in FIG. 2. FIG. 2 illustrates the process of mixing the signal down to baseband once the carrier frequency (and carrier signal mixed down to carrier offset) is determined. A carrier signal 221 is mixed with a second carrier signal 222 at mixer 223. A narrow low-pass filter 220 is applied of appropriate bandwidth to reduce the effect of out-of-bound noise. Demodulation occurs at functional blocks 225 in accordance with the coherent demodulation scheme of the present invention. The unwrapped phase 230 of the complex signal is determined. An optional third mixer stage, in which the phase evolution is used to estimate the frequency differential between the calculated and real carrier frequency can be applied. The structure of the packet is then leveraged to determine the beginning of the coding region of the BPSK signal at block 240. Mainly, the presence of the sync header, which appears as an FM porch in the amplitude signal of the complex demodulated signal is used to determine the starting bounds of the packet. Once the starting point of the packet is determined the signal is rotated at block 250 on the IQ plane and standard bit identification and eventually decoded at block 260.

In addition to demodulation, the transbody communication module may include a forward error correction module, which module provides additional gain to combat interference from other unwanted signals and noise. Forward error correction functional modules of interest include those described in PCT Application Serial No. PCT/US2007/024225; the disclosure of which is herein incorporated by reference. In some instances, the forward error correction module may employ any convenient protocol, such as Reed-Solomon, Golay, Hamming, BCH, and Turbo protocols to identify and correct (within bounds) decoding errors.

Receivers of the invention may further employ a beacon functionality module. In various aspects, the beacon switching module 306 may employ one or more of the following: a beacon wakeup module, a beacon signal module, a wave/frequency module, a multiple frequency module, and a modulated signal module.

The beacon switching module 306 of FIG. 1B may be associated with beacon communications, e.g., a beacon communication channel, a beacon protocol, etc. For the purpose of the present disclosure, beacons are typically signals sent either as part of a message or to augment a message (sometimes referred to herein as "beacon signals"). The beacons may have well-defined characteristics, such as frequency. Beacons may be detected readily in noisy environments and may be used for a trigger to a sniff circuit, such as described below.

In one aspect, the beacon switching module 306 may comprise the beacon wakeup module, having wakeup functionality. Wakeup functionality generally comprises the functionality to operate in high power modes only during specific times, e.g., short periods for specific purposes, to receive a signal, etc. An important consideration on a receiver portion of a system is that it be of low power. This feature may be advantageous in an implanted receiver, to provide for both small size and to preserve a long-functioning electrical supply from a battery. The beacon switching module 306 enables these advantages by having the receiver operate in a high power mode for very limited periods of time. Short duty cycles of this kind can provide optimal system size and energy draw features.

In practice, the receiver 100 may "wake up" periodically, and at low energy consumption, to perform a "sniff function" via, for example, a sniff circuit. For the purpose of the present application, the term "sniff function" generally refers to a short, low-power function to determine if a transmitter is present. If a transmitter signal is detected by the sniff function, the device may transition to a higher power communication decode mode. If a transmitter signal is not present, the receiver may return, e.g., immediately return, to sleep mode. In this manner, energy is conserved during relatively long periods when a transmitter signal is not present, while high-power capabilities remain available for efficient decode mode operations during the relatively few periods when a transmit signal is present. Several modes, and combination thereof, may be available for operating the sniff circuit. By matching the needs of a particular system to the sniff circuit configuration, an optimized system may be achieved.

Figure 3A:
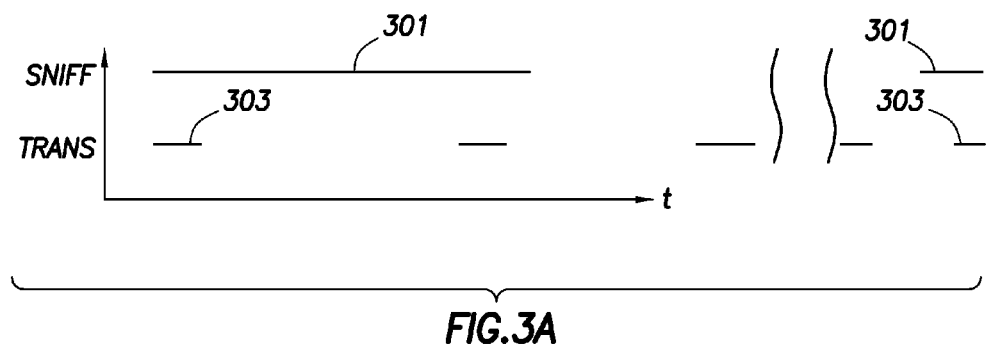
FIG. 3A illustrates a beacon switching module providing a sniff period longer than a transmit signal repetition period.

FIG. 3A illustrates a beacon switching module 306 wherein a sniff period 301 is longer than a transmit signal repetition period 303. The time function is provided on the x axis. As shown, the transmit signal repeats periodically, with a sniff function also running. In practice, effectively, the sniff period 301 may be longer than the transmit signal repetition period 303. In various aspects, there may be a relatively long period of time between the sniff periods. In this way, the sniff function, e.g., implemented as a sniff circuit, is guaranteed to have at least one transmission to occur each time the sniff circuit is active.

Figure 3B:
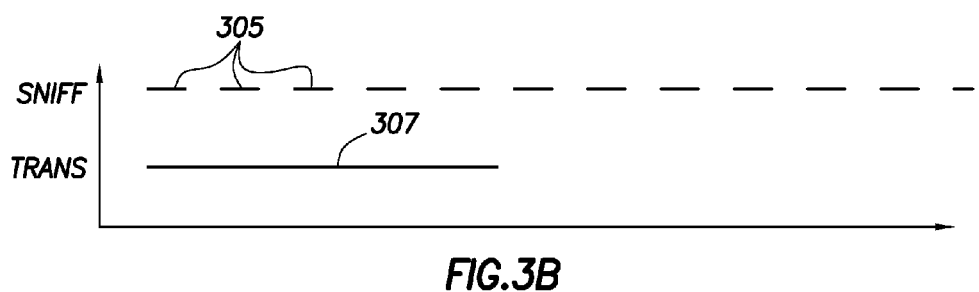
FIG. 3B illustrates a beacon switching module providing a short but frequent sniff period and a long transmit packet are provided.

Referring now to FIG. 3B illustrates the beacon switching module 306 wherein a short but frequent sniff period 305 and a long transmit packet 307 are provided. The sniff circuit will activate at some point during the transmit time. In this manner, the sniff circuit may detect the transmit signal and switch into a high power decode mode.

An additional beacon wakeup aspect is to provide the "sniffing" function in a continuous mode. In contrast to the approaches provided above, this aspect of the transbody beacon transmission channel may exploit the fact that the total energy consumption is the product of average power consumption and time. In this aspect, the system may minimize the total energy consumption by having very short periods of activity, in which case the periods of activity are averaged down to a small number. Alternately, a low continuous sniff activity is provided. In this case, the configuration provides a sufficiently low power so that the transmission receiver runs continuously with total energy consumption at an appropriate level for the parameters of a specific system.

Figure 3C:
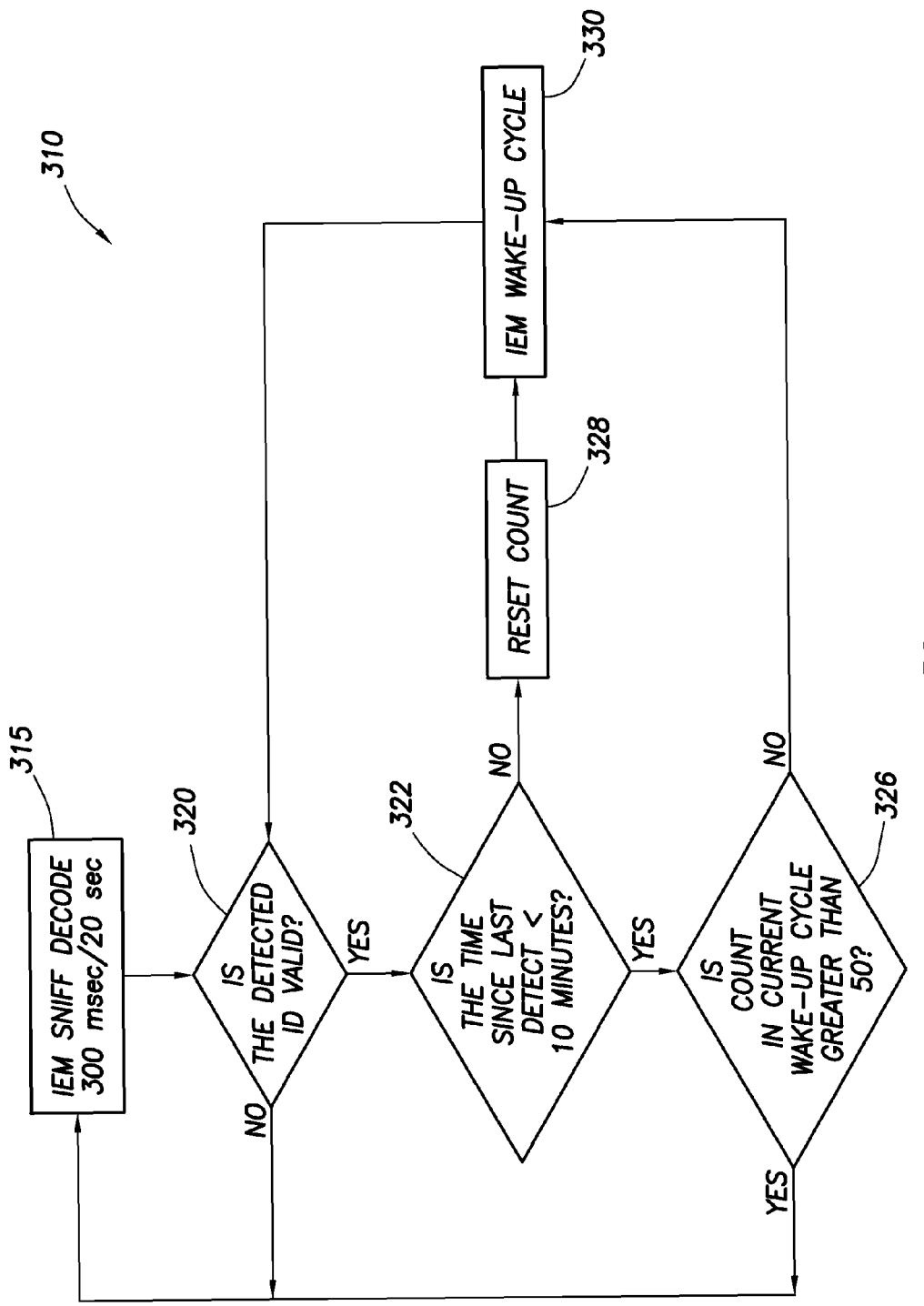
FIG. 3C illustrates a flow chart for a sniff procedure performed by a sniff module, according to an aspect.

A functional flow diagram of the beacon switching module 306 of FIG. 1B is shown in FIG. 3C. In FIG. 3C, the beacon switching module is shown as sniff module 310. The sniff module 310 is configured to scan for data encoded in current flow produced by ionic emission. The data are received at the receiver as a conductive signal at a set schedule, e.g., every 20 seconds. At step 315, the period during active sniff is limited, e.g., 300 msec. This relatively low duty-cycle allows for lower average power functionality for extended system life. At step 320, the receiver determines if a signal is present and if that signal has a valid ID. If no signal having a valid ID is detected during active sniff (as illustrated by arrow 320), the process returns to step 315 and the active sniff is turned off until the next predetermined active period. If at step 320 a signal having a valid ID is received, then the process moves to step 322. At step 322, the receiver determines if the signal received is from a previously detected ionic transmitter. If the signal is from a previously detected ionic transmitter, then the process moves to step 326. At step 326 the receiver determines whether the count (in other words, individual valid detections of the same ID) in the current wake up cycle (specified time since the last reported ID, such as 10 minutes) is greater than a specified number (such as 50) as measured by a threshold counter. If the count exceeds this threshold as determined by the threshold counter, the receiver returns to sniff mode. If the count does not exceed the threshold value, then the process moves to step 330 and the receiver operates in 100% detection mode to analyze the received data encoded in the current flow by the ionic emission. Once the received data are decoded and analyzed, the process return to step 315. If at step 322, the receiver determines that the data encoded in the current flow is coming from a different valid source than previously detected, then the process moves to step 328. At step 328 the threshold counter is reset.

Figure 3D:
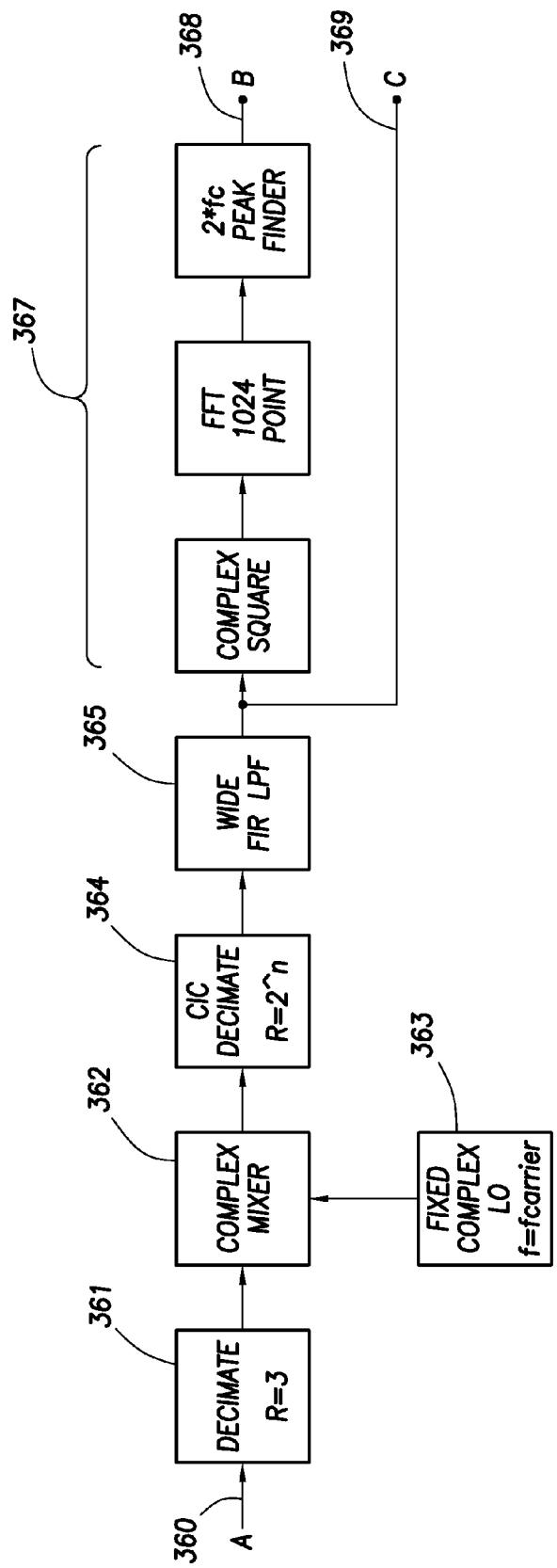
FIG. 3D illustrates a functional block diagram for a beacon module within a receiver, according to one aspect.
Figure 3E:
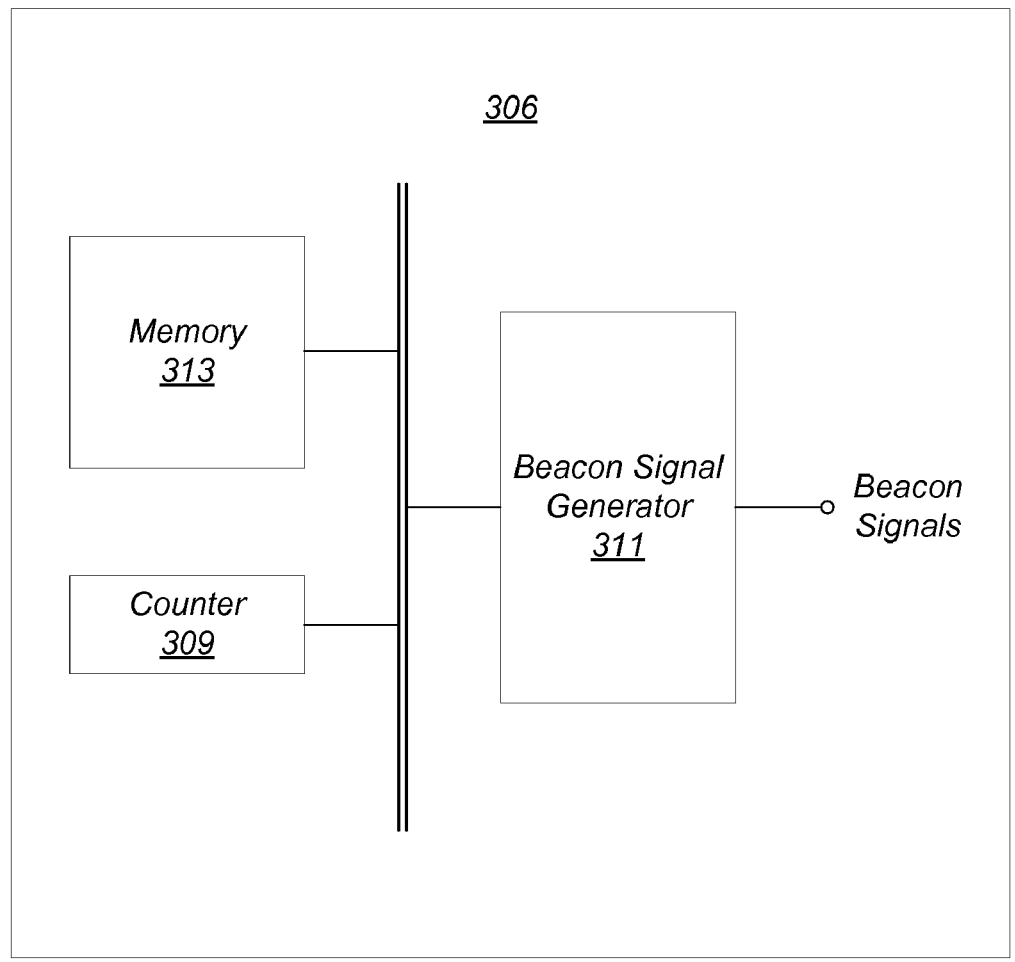
FIG. 3E illustrates a block diagram of a beacon switching module comprising a counter coupled to a beacon signal generator and a memory unit coupled to the beacon signal generator.

Another view of a beacon module is provided in the functional block diagram shown in FIG. 3D. The scheme outlined in FIG. 3D outlines one technique for identifying a valid beacon. The incoming signal 360 represents the signals received by electrodes, bandpass filtered (such as from 10 KHz to 34 KHz) by a high frequency signaling chain (which encompasses the carrier frequency), and converted from analog to digital. The signal 360 is then decimated at block 361 and mixed at the nominal drive frequency (such as, 12.5 KHz, 20 KHz, etc.) at mixer 362. The resulting signal is decimated at block 364 and low-pass filtered (such as 5 KHz BW) at block 365 to produce the carrier signal mixed down to carrier offset—signal 369. Signal 369 is further processed by blocks 367 (fast Fourier transform and then detection of two strongest peaks) to provide the true carrier frequency signal 368. This protocol allows for accurate determination of the carrier frequency of the transmitted beacon.

Figure 4:
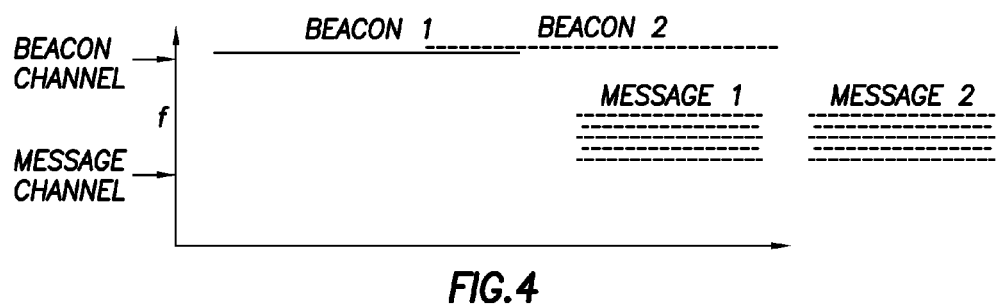
FIG. 4 illustrates a beacon functionality wherein a beacon is associated with one frequency and a message is associated with another frequency.

FIG. 4 illustrates a beacon functionality wherein a beacon is associated with one frequency, e.g., a beacon channel, and a message is associated with another frequency, e.g., a message channel. This configuration may be advantageous, for example, when the system is dealing with multiple transmit signals. The solid line represents the beacon from Transmit Signal 1. The dashed line represents the beacon from Transmit Signal 2. In various transmission situations, the Transmit Signal 2's beacon might overlap with that of Transmit Signal 1, as depicted. Message Signal 1 and Message Signal 2 can be at different frequencies from their respective beacons. One advantage may be that the beacon from Transmit Signal 2 does not interfere with the message from Transmit Signal 1 at all, even though they are transmitted at the same time. While 4 is shown with two transmitters, it will be apparent to one of ordinary skill in the art to modify the system so as to scale it to many more transmitters. The requirements of a particular system may, to some extent, dictate the particular architecture of that system.

Further examples of beacon functionality modules are described in PCT Application Serial No. PCT/US08/85048; the disclosure of which is herein incorporated by reference.

Various aspects may employ a frequency hopping functionality module. The frequency hopping functionality module may be associated with the specific communications channel(s), frequency hopping protocol, etc. As such, various aspects may utilize one or more frequency hopping protocols. For example, the receiver may search the designated range of frequencies, e.g., two or more different frequencies, in which the transmission could fall. When a single proper decode is achieved, the in vivo transmitter has accomplished its mission of communicating its digital information payload to the receiver.

In some instances, a transmitted frequency uncertainty provided by random frequency hopping, e.g., via a random module, may create multiple benefits. One such benefit, for example, may be easy implementation on a small die. To illustrate, an in vivo transmitter carrier frequency oscillator can be an inaccurate free running oscillator that is easily implemented on a small portion of a 1 mm die. Accuracies on the order of +/−20 are easily tolerated because the receiver employs frequency searching algorithms.

Another such benefit may be extended battery life. To illustrate, over the course of the transmitter battery life, e.g., three to ten minutes, the probability of the transmitter transmitting on a clear channel that can be received by the frequency agile receiver may be significantly enhanced due to random frequency hopping.

Still another benefit may be minimized collision events in high volume environments. To illustrate, minimization of collision probability when multiple in vivo transmitters, e.g., ingestible event markers, are potentially transmitting simultaneously, such as in instances where the multiple ingestible event markers are ingested concurrently or in close temporal proximity. Stated differently, without frequency hopping functionality, there may be a high probability that ingestible event markers of a similar lot will transmit on the same (or nearly the same) frequency, resulting in multiple collisions.

In certain aspects, the useful frequency spectrum for use in volume conduction applications ranges from about 3 kHz to 150 kHz. Through detailed animal studies it has been observed that in some environments, the in vivo transmitter, supra, having a received signal level in the range of 1 to 100 µV may compete with narrow band interfering signals on the order of hundreds to thousands of µV in the same frequency spectrum. To mitigate the destructive nature of interfering signals, a frequency hopping channel or protocol may be employed in which the in vivo transmitter randomly frequency hops a narrow band transmitted signal, e.g., a modulated signal such as a binary phase shift keying (BPSK) signal or FSK signal, output on each transmission.

Further examples of Frequency Hopping modules are described in PCT Application Serial No. PCT/US08/85048; the disclosure of which is herein incorporated by reference.

Various aspects of the receivers may employ a collision avoidance functionality module. The collision avoidance functionality module may be associated with the specific communications channel(s), collision avoidance protocols, etc. As such, various aspects may utilize various collision avoidance protocol techniques associated with the specific communications channel(s). Collision avoidance techniques may be particularly useful, for example, in environments where two or more in vivo transmitters are present, e.g., where an individual ingests multiple IEMs. In such an environment, if the various in vivo transmitters send their signals continuously, the transmission of one may obscure the transmission from all the other in vivo transmitters. As a result, failure to detect signals may increase significantly.

Various aspects may include various collision avoidance approaches, alone or in various combinations.

One such approach employs multiple transmit frequencies. By using frequency-selective filtering, the transmitter broadcasting at f1 can be distinguished from the transmitter broadcasting at f2, even if they are transmitting simultaneously.

Further examples of Collision Avoidance modules are described in PCT Application Serial No. PCT/US08/85048; the disclosure of which is herein incorporated by reference.

Additional functional modules that may be included in the transbody communication module of the receivers of the invention include a clock functionality module, which associates a particular time with a given signal, e.g., as described in one or more of PCT Application Serial No. PCT/US08/85048; PCT Application Serial No. PCT/US2007/024225 published as WO 2008/095183 and PCT Application Serial No. PCT/US2007/024225 published as WO 2008/063626; the disclosures of which are herein incorporated by reference.

As indicated above, the transbody conductive signal may also be a signal produced by smart parenteral delivery systems, e.g., as described in PCT application serial no. PCT/US2007/015547 published as WO 2008/008281; the disclosure of which is herein incorporated by reference. In these instances, the body-associate medical device may be configured to derive a number of different types of information about a fluid delivery event from the received signal. Types of information that may be derived include, but are not limited to: that the delivery event is about to occur or has occurred, how much fluid was administered, the identity of the fluid that was administered, etc. For those instances where the receiver is configured to determine how much fluid was administered, the device may be configured to receive variable volume administration data, such that it is configured to receive different values for this data field.

The receivers may provide a further communication path via which collected data can be transferred from the receiver to another device, such as but not limited to, a smart phone, hospital information system, etc. This further communication path is provided by an "extra-corporeal communication" module. This extra-corporeal communication module may employ a variety of different protocols. Protocols of interest include both wired and wireless communication protocols. For instance, a receiver may include conventional RF circuitry (for example, operating in the 405-MHz medical device band) with which a practitioner can communicate, e.g., by using a data retrieval device, such as a wand or analogous device. Of interest in some aspects are low power wireless communication protocols, such as BLUETOOTH™ wireless communication protocols. Also of interest are communications protocol that employ a multi-purpose connector, such as described in greater detail below.

Where the receiver includes at least a portion that is external to a living body during use, that portion may have output devices for providing, e.g., audio and/or visual feedback; examples of which include audible alarms, LEDs, display screens, etc. The external portion may also include an interface port via which the component can be connected to a computer for reading out data stored therein. In addition, the external portion may include one or more operation elements, such as buttons or analogous structures, that allow a user to manually interact with the body-associate medical device in some way, e.g., to test operability, to turn the device on, to reset the device, etc.

In some instances, an extra-corporeal communication module is employed to reconfigure various parameters of the receiver. As such, the communication module may be a two-way communication module. Parameters that may be re-configured include the "Duty Cycle" of the data acquisition, e.g., how often the receiver sniffs for IEMs, how often and for how long the receiver collects ECG or activity data, etc.

In one aspect, the extra-corporeal communication module may be implemented to have its own power supply so that it may be turned on and off independently from other components of the device, for example, by a microprocessor.

Receivers in accordance with the teachings of the invention may include one or more distinct physiological sensing modules. By physiological sensing module is meant a capability or functionality of sensing one or more physiological parameters or biomarkers of interest, such as, but not limited to: cardio-data, including heart rate, electrocardiogram (ECG), and the like; respiration rate, temperature; pressure; chemical composition of fluid, e.g., analyte detection in blood, fluid state, blood flow rate, accelerometer motion data, etc. Where the receiver has physiological parameter or biomarker sensing capability, the number of distinct parameters or biomarkers that the signal receiver may sense may vary, e.g., one or more, two or more, three or more, four or more, five or more, ten or more, etc. The term "biomarker" refers to an anatomic, physiologic, biochemical, or molecular parameter associated with the presence and severity of a health state, such as a specific disease state. Depending on the particular aspect, the device may accomplish one or more of these sensing functions using a signal receiving element of the device, such as by using electrodes of the receiver for signal receiving and sensing applications, or the receiver may include one or more distinct sensing elements (such as micro-needles described below) that are different from the signal receiving element. The number of distinct sensing elements that may be present on the (or at least coupled to the) signal receiver may vary, and may be one or more, two or more, three or more, four or more, five or more, ten or more, etc.

In certain aspects, the receiver includes a set of two or more, such as two or three, electrodes that provide for dual functions of signal receiving and sensing. For example, in addition to receiving signal, the electrodes can also serve additional sensing functions. In certain aspects, the electrodes are used to generate electrocardiogram data. From that data, there are many kinds of processing that can be done, e.g., to detect various cardiac events, such as tachycardia, fibrillations, heart rate, etc., to detect neurological conditions, such as seizures (e.g., as may occur in epilepsy (see for example devices and modules configured for seizure detection, described in greater detail below), etc. The obtained electrocardiogram data can be used to titrate medications, or can be used for to provide an alert when an important change or significant abnormality in the heart rate or rhythm is detected. These data are also helpful in certain aspects for monitoring heart rate in patients who do not have pacemakers or as an alternative to patients who might normally require a Holter monitor or a Cardiac Event Monitor, portable devices for continuously monitoring the electrical activity of the heart for 24 hours or other devices. An extended recording period is useful for observing occasional cardiac arrhythmias that are difficult to identify in shorter time periods.

As mentioned above, one or more additional physiological sensors distinct from the electrodes may be included in the receiver. For example, a temperature sensor, such as a thermistor, CMOS temperature sensor, resistive temperature devices (RTDs), may be employed to obtain precise measurements of temperature. An additional physiological sensor may include an LED and a photodiode combined into a pulse oximeter, which may be employed to measure blood oxygenation, which would also give information about pulse pressure. In addition, aspects of the signal receivers include a pressure sensor, e.g., where the signal receiver is implanted next to an artery to get measurements of arterial blood pressure. Strain gauges are present in certain aspects to measure pressure deflections, which are then attached to the signal receiver.

The receivers may also include analyte detection sensors. For example, specific chemical sensors may be incorporated into the signal receivers to detect the presence of various agents, e.g., alcohol, glucose, BNP (B-type Natriuretic peptide, which is associated with cardiac disease), etc. Sensors of interest include those configured to detect the presence of a chemical analyte in a biological fluid sample, where analytes of interest include, but are not limited to: blood sugar (glucose), cholesterol, bilirubin, creatine, various metabolic enzymes, hemoglobin, heparin, hematocrit, vitamin K or other clotting factors, uric acid, carcinoembryonic antigen or other tumor antigens, various reproductive hormones such as those associated with ovulation or pregnancy, drugs of abuse and/or metabolites thereof; blood alcohol concentration, etc. In certain aspects, substances or properties for which the receiver is configured to detect include lactate (important for athletes), oxygen, pH, alcohol, tobacco metabolites, and illegal drugs (important for both medical diagnosis and law enforcement). Where the receiver includes an analyte detecting sensing element, this sensing element can be configured in the receiver in a number of different ways. For example, a sensor that includes a selectively permeable membrane which is permeable to the agent one wants to detect may be provided, where there is an isolated cell behind the membrane and the agent passes through the membrane. Changes in the properties, such as electrical properties, of the cell, are then measured. In certain aspects, a small reservoir on the side of the receiver with a membrane across it is employed, and electrical circuitry behind it is measured. Also of interest are ChemFET sensors, which are based on the binding of analyte to the sensor causing a change in the conductivity. In certain aspects, a material whose electrical properties (or other properties) are changed when the material, e.g., protein analyte, binds to it are employed. Blood alcohol concentration may be determined any number of ways, including but not limited to: sensors that analyze fluid samples, such as perspiration, optical spectroscopic sensors, etc.

Of interest are receivers that include at least an electrocardiography (ECG) sensor module. An ECG sensor module is a module which is configured to obtain ECG data and, if desired, additionally perform one or more of processing the data in some way, storing the data and retransmitting the data. The ECG data may be employed by the receiver to derive a number of different metrics, including but not limited to: R-wave, heart rate, heart rate variability, respiration rate, etc. Where the receiver includes one or more physiological sensing functionalities, the device may further include sensing modules that are configured to obtain and process data from these sensing functionalities. For example, where the receiver includes an ECG sensing functionality, the device may include an appropriate functional module (for example in the form of programming) that can handle and process the raw data from these sensors. An example of a physiological sensing module of interest is of an ECG sensing module as illustrated in FIG. 5.

Figure 5:
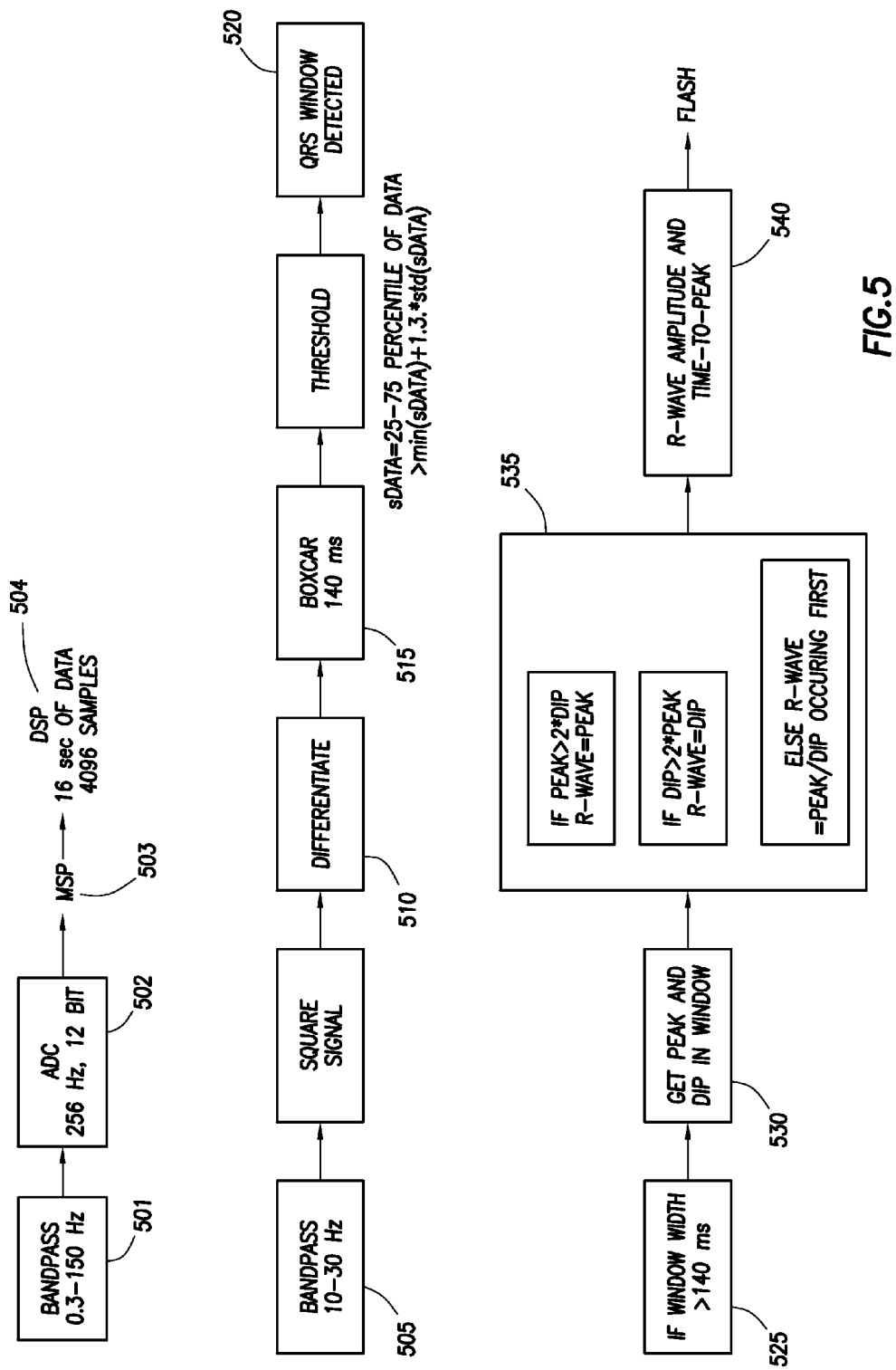
FIG. 5 illustrates a functional block diagram of an ECG sensing module that may be present in a receiver, according to one aspect.

Referring now to FIG. 5, an illustration of an ECG sensing module which implements a modified Hamilton and Tompkins algorithm is shown. FIG. 5 represents one possible implementation of an R-wave detection algorithm, according to one aspect of the invention. As illustrated in FIG. 5, the ECG sensing modules receives signals via electrodes and bandpasses those signals (e.g., 0.3 to 150 Hz) at filter 501, before converting the signal to a digital signal at A/D converter 502. The signal is then sent to microprocessor 503 and on to digital signal processor 504 for processing. For example, the data signal received by the DSP 504 is bandpass filtered (e.g., at 10-30 Hz) at block 505, differentiated at block 510, and further filtered at block 515 to emphasize and eventually identify the window in which the QRS complex exists at block 520. Logic is then applied to identify the R-wave within each window. At logic block 525, it is determined if the window width is, for example, greater than 140 ms. The peak and dip in the window is determined, as shown by logic block 530. If the peak is greater than twice the dip, then the R-wave is equal to the peak. If the dip is greater than twice the peak, then the R-wave is equal to the dip. Otherwise, the R-wave is equal to the ratio of the peak to the dip occurring first. This is shown by logic block 535. Thereafter, the R-wave amplitude and time-to-peak is sent to memory (e.g., flash), as shown by logic block 540.

Also of interest are accelerometer modules. An accelerometer module is a module which is configured to obtain accelerometer data and, if desired, additionally perform one or more of processing the data in some way, storing the data and retransmitting the data. The accelerometer module may be employed by the receiver to derive a number of different metrics, including but not limited to: data regarding patient activity, mean activity, patient position and angle, activity type, such as walking, sitting, resting (where this data may be obtained with a 3-axis accelerometer); and then save the obtained data. Of interest are both analog accelerometers and digital accelerometers. An example of an accelerometer module of interest is shown in FIG. 6.

Figure 6:
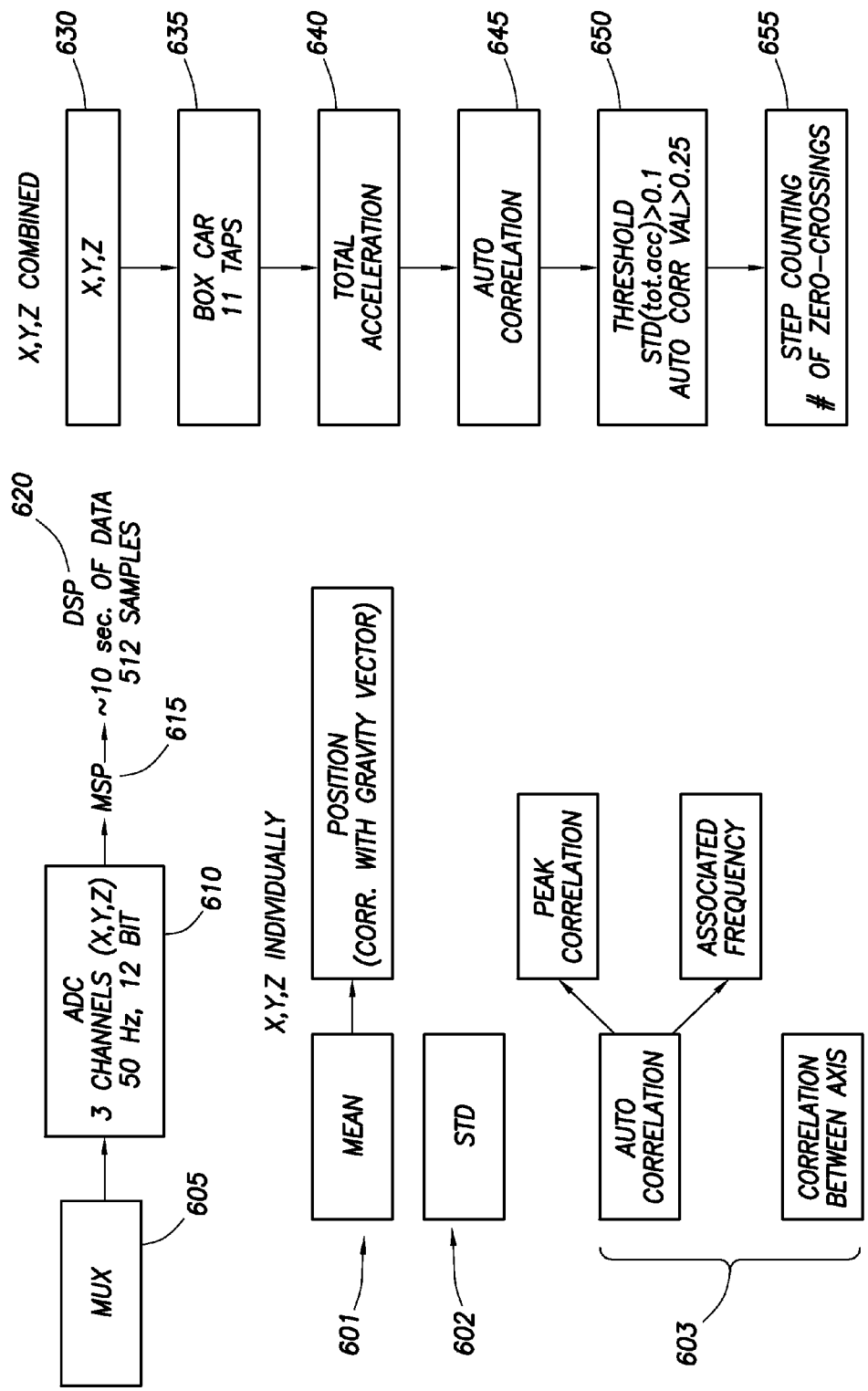
FIG. 6 illustrates a functional block diagram of an accelerometer module that may be present in a receiver of the invention, according to one aspect.

Referring now to FIG. 6, a functional block diagram of a 3-axis accelerometer module that is configured to obtain and process accelerometer data from three different axes, according one aspect of the invention, is shown. Each axis of the accelerometer is processed to determine the mean (as shown at block 601), standard deviation (as shown at blocks 602), and auto-correlation (as shown at block 603). The mean is reflective of the orientation of the accelerometer with respect to gravity, whereas the standard deviation and autocorrelation are important metrics describing the amplitude and frequency of the observed motion, for example, peak correlation, associated frequency, and correlation between axes. In order to perform step-counting, the three axes are combined at block 630 and filtered at block 635. The total acceleration is constructed, as shown at block 640. The use of the total acceleration makes the system robust against different orientations of the receiver with respect to the subject. Once the total acceleration is computed the standard deviation and auto correlation are calculated, as shown at block 645. These values are then thresholded (for example standard deviation>0.1 and Auto-correlation>0.25) to determine whether significant, cyclic motion exists, as shown at block 650. Then, as shown at block 655, if the thresholded values are exceeded, the number of steps is determined as the number of zero-crossings of the mean corrected total acceleration.

In some receivers, the device may include an environmental functional module. Environmental functional modules are modules that are configured to or acquire data related to the environment of the receiver, e.g., the environmental conditions, whether the receiver is connected to a skin surface, etc. For example, the environmental functional module may be configured to obtain receiver ambient temperature data. The environmental functional module may be configured to determine electrode connection, e.g., by impedance measurement. The environmental functional module may be configured to determine battery voltage. The above specific functions of the environmental functional module are merely illustrative and are not limiting.

A receiver may be configured to handle received data in various ways. In some aspects, the receiver simply retransmits the data to an external device (e.g., using conventional RF communication). In other aspects, the receiver processes the received data to determine whether to take some action such as operating an effector that is under its control, activating a visible or audible alarm, transmitting a control signal to an effector located elsewhere in the body, or the like. In still other aspects, the receiver stores the received data for subsequent retransmission to an external device or for use in processing of subsequent data (e.g., detecting a change in some parameter over time). The receivers may perform any combination of these and/or other operations using received data.

In certain aspects where the receiver is an IEM signal receiver, the data that are recorded on the data storage element includes at least one of, if not all of, time, date, and an identifier (e.g., global unique serial no.) of each IEM administered to a patient, where the identifier may be the common name of the composition or a coded version thereof. The data recorded on the data storage element of the receiver may further include medical record information of the subject with which the receiver is associated, e.g., identifying information, such as but not limited to: name, age, treatment record, etc. In certain aspects, the data of interest include hemodynamic measurements. In certain aspects, the data of interest include cardiac tissue properties. In certain aspects, the data of interest include pressure or volume measurements, temperature, activity, respiration rate, pH, etc.

Receivers may include a variety of different types of power sources which provide operating power to the device in some manner. The nature of the power block module may vary. In some instances, the power block may include a battery. When present, the battery may be a onetime use battery or a rechargeable battery. For rechargeable batteries, the battery may be recharged using any convenient protocol. Of interest is a protocol that results in multi-tasking of elements of the receiver. For example, receivers of the invention may include one or more electrodes which are used for a variety of functions, such as receiving conductively transmitted signals, sensing physiological data, etc. The one or more electrodes, when present, may also be employed as power receivers which may be employed for recharging the rechargeable battery, e.g., as further described in the Multi-Purpose Connection Module section below. Alternatively, the power block may be configured to receive a power signal, e.g., where the power block comprises a coil which can impart power to the device when an appropriate magnetic field is applied to the receiver. In yet other instances, the device may include a body-powered power block, such as that described in U.S. patent application Ser. No. 11/385,986, the disclosure of which is herein incorporated by reference.

The receiver may include a power supply module which controls when certain states are assumed by the device, e.g., in order to minimize device power usage. For example, the power supply module may implement a duty cycle for data collection based on time of day, or patient activity, or other events, where the implemented duty cycle may be based on a signal factor or multiple factors. For example, the power supply module may cause the receiver to obtain patient activity data (for example by an accelerometer module) when the patient is moving around and not when the patient is at rest. In other aspects, the power management module may have the receiver collect ECG data only at night, for example by using a real time clock in the receiver to collect ECG only in a predetermined time range, e.g., from 9 PM to 7 AM.

As stated earlier, the receiver may be configured to have various states—e.g., an idle state or one or more active states—with the intermediary module cycling the high power functional block between active and inactive states as needed for each desired receiver state. In addition, other receiver elements may be cycled on and off during different states of the receiver by a power supply module. The power supply module may be configured to control the power supply to various circuit blocks within the medical device—e.g., circuit blocks relating to power supply to processors, circuit blocks relating to various peripheral components (e.g., wireless communication module, etc.) and their power supplies, etc. Therefore, during each state of the receiver, the power supply to various components of the receiver may be independently cycled on and off as needed to achieve power efficiency (and independently from the cycling of the high power functional block between active and inactive states as discussed earlier). For example, in some instances, receivers may be configured to be present in two or more different active states, where a different task or set of tasks is performed in each different active state. The receivers of interest may be configured to perform an IEM signal detection protocol when present in a first active state and a physiological data detection protocol when present in a second active state. In these types of receivers, various components of the receiver may be independently cycled on and off as required to achieve power efficiency (and independently from the cycling of the high power functional block between active and inactive states as discussed earlier).

The power supply module may comprise one or more individual power supplies to activate and deactivate power supply to these various components. For example, in one aspect, the power supply module may comprise a high power processing input/output power supply to supply input/output power to the high power processing block; and, a high power processing core power supply to supply core power to the high power processing block. Furthermore, the power supply module may comprise a wireless communication input/output power supply to supply input/output power to the wireless communication module; and, a wireless communication core power supply to supply core power to the wireless communication module.

It should be understood that a single power supply may be used to provide power to multiple components. For example, a single power supply may provide input/output power to both the high power processing block and to the wireless communication module. In one aspect, the power supply module receives control signals from a low power processing block (for example, the microprocessor) which determines which power supplies are turned on/off.

Figure 26A:
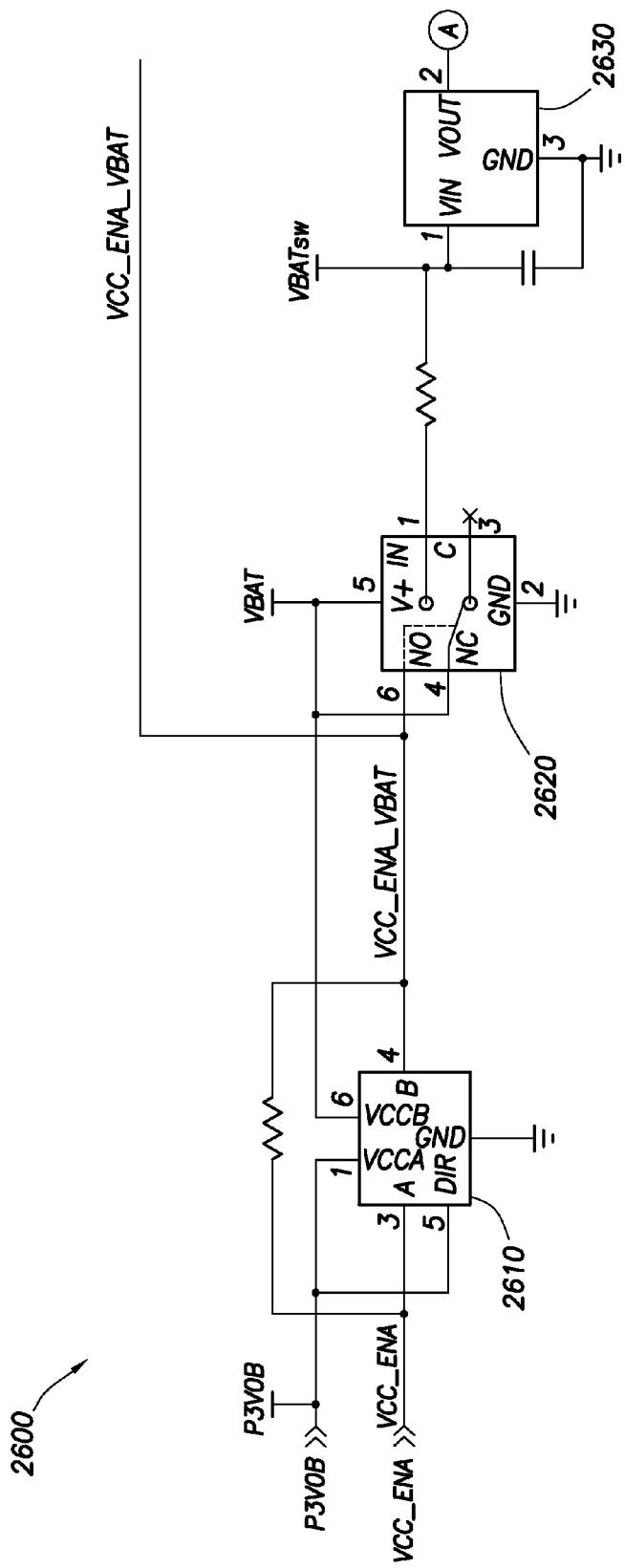
FIGS. 26A-B (referred to collectively as FIG. 26) provide a circuit diagram of circuitry for controlling the power supply to various components of a receiver that includes a multi-purpose connector, according to one aspect.
Figure 26B:
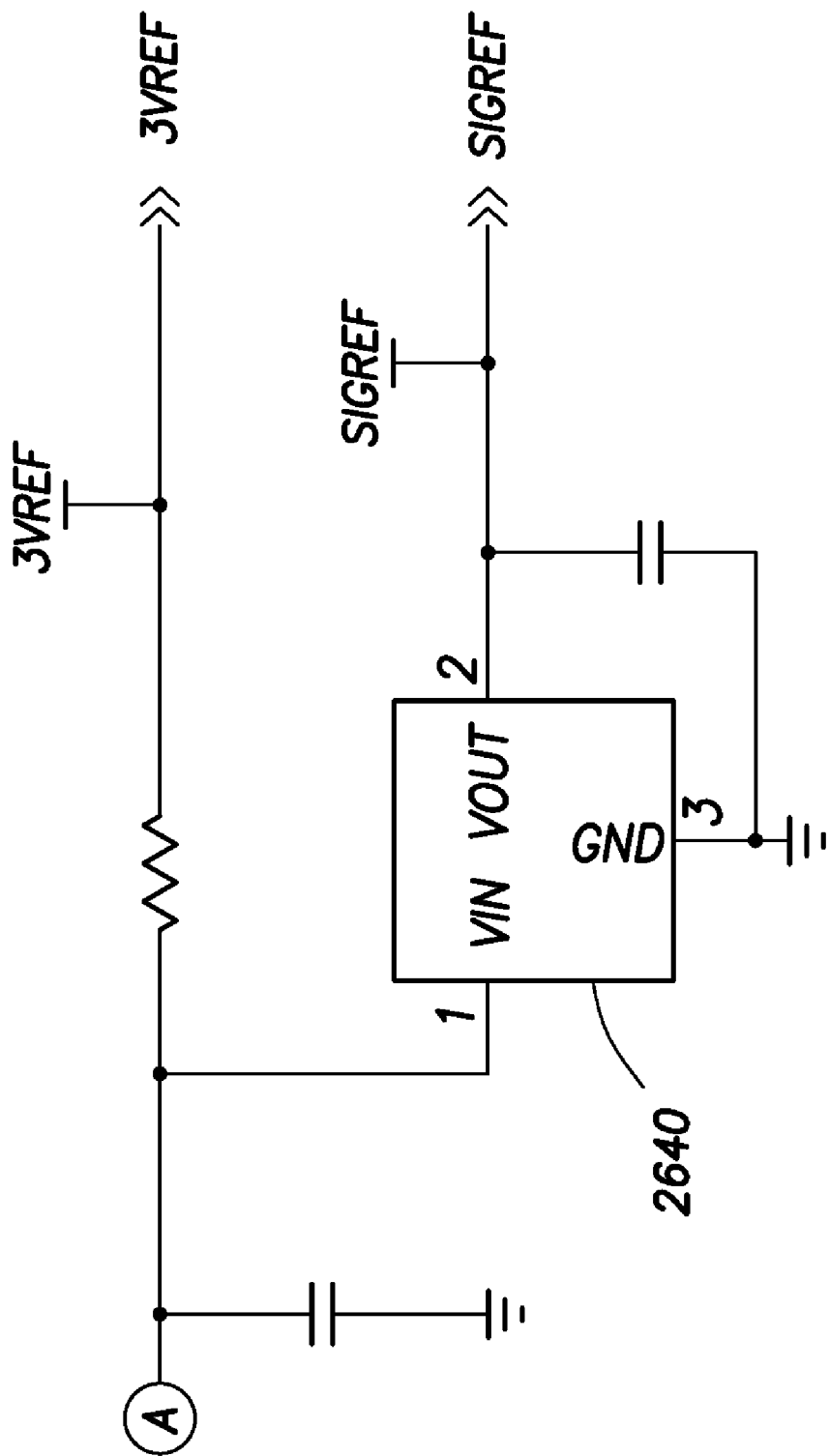

Referring now to FIG. 26, a circuit diagram of part of the receiver's circuitry in accordance with the teaching of the present invention is provided. The circuitry 2600 is responsible for controlling the power supply to various components of the receiver. FIG. 26 is connected to FIG. 24 at signal line "VCC_EN_BAT" shown in both figures, and works in conjunction with part of the circuit in FIG. 24 to control the power supplies. As illustrated in FIG. 26, translator 2610 is shown electrically coupled to switch 2620 which is electrically coupled to voltage references 2630 and 2640. Translator 2610 translates data signal VC_ENA on its A bus to signal VC_EN_BAT on its B bus. Signal VCC_EN_BAT is connected to the enable pins of regulators 24155, 24157, and 24159 (illustrated in FIG. 24) which supply power to various components. Therefore, data signal VCC_EN_BAT may enable/disable the power supply for various components of the receiver. For instance, regulator 24155, 24157, and 24159 provide power to the DSP core, DSP & wireless communication I/Os, and wireless communication core, respectively. Therefore, each of these components can be powered off and on with a corresponding enable/disable data signal (VCC_EN_BT) from circuitry 2600.

Receivers may include a multi-purpose connector module. A multipurpose connector module includes living subject contacts, such as electrodes, as described herein (also referred to hereinafter as "multi-purpose connectors"), and may be used for periodic recharging of a power source of the device, reprogramming of a control function of the device and/or data retrieval from the device. This configuration is in contrast to configurations that include a separate connector for each of these functions, such as distinct patient connectors, power connectors and device configuration connectors.

Receivers that include multi-purpose connector modules are capable of variable connection between a target object, such as a patient or patient-related device, and a second external device, such as an external programming device and an external charger device. The connection may be used to facilitate communication of signals, e.g., electrical signals, digital signals, optical signals, combinations of various types of signals, etc. The term "variable connection", as used herein, refers to the capability of the multi-purpose connector to receive a connecting component associated with one of a living subject, such as a patient, and the second external device and to form a connection based on the specific connecting component, e.g., a connecting component associated with a patient or a connecting component associated with the second external device. The receiver further includes multiple functional blocks to control signals associated with a communication of signals via the connection. In various aspects, the second external device comprises an external programming device and the second functional block comprises a controller functional block to control signals associated with a communication between the external programming device and the receiver. When the receiver is connected to the external programming device via the multi-purpose connector, the external programming device may be used to programmatically control the receiver. In various aspects, the second external device comprises an external charger device and the second functional block comprises a power functional block to control signals associated with a communication between the external charger device and the receiver. When the receiver is connected to the external charger via the multi-purpose connector, the external charger may be used to charge the receiver. In various aspects, the second functional block comprises a patient interactive functional block. When the receiver is connected to the patient or to a patient-related device via the multi-purpose connector, the device may be used to interactively communicate with the patient or patient-related device. For example, the receiver may be configured with electrodes to stimulate or sense various patient parameters and physically attached to the patient to facilitate various functional goals, e.g., deliver a pacing stimulation to the patient; receive physiologic information from the patient, etc.

In some aspects, at least one of the multiple functional blocks is configured as a signal director. The signal director may be any component, subcomponent, or combination thereof capable of carrying out the described functionality. In one example, the receiver is physically associated with, e.g., configured to include, the signal director. Such a configuration may comprise one or more circuits, etc. In another example, the signal director is physically distinct from the receiver. Such a configuration may comprise a router or other network device capable of facilitating the signal functionality described herein. The signal director may comprise a control element configured to control signals, e.g., discriminate the signals. In various aspects, the signal director comprises at least one of software and circuitry.

Signal control or discrimination may be based on various criteria, e.g., voltage, frequency, manual control, programmatic control, etc. Control element configuration varies accordingly. For example, a control element that discriminates based on voltage may be implemented as one or more diodes, a thermistor, etc. A control element that discriminates based on frequency may be implemented as a high-pass filter or as a low-pass filter. A control element providing manual and/or programmatic control may be implemented as an analog switch, a relay, a multiplexor, etc. Various other implementations may be based on various parameters such as light, temperature, time, etc.

As indicated above, multi-purpose connectors are connector elements that are configured to provide connection to a patient and one or more second external devices, such as an external programming device, an external charger device, or an external data processor. Accordingly, the structure of the multi-purpose connector is such that it can provide connection of the receiver to a patient, either directly or through another device (as described below) and to another device. Accordingly, the receiver can be connected to a patient via the multi-purpose connector at a first time and to another device via the same multi-purpose connector at a second time that is different from the first time, such that the same multi-purpose connector is employed to connect the receiver to different entities at different times. As such, the multi-purpose connector may be used to connect, at different times, one or more of the physical implementations of functional blocks of the device to the patient and to at least one or more additional external devices, such as an external charger, an external programming device, or an external data processor.

The structure of the multi-purpose connector may vary as desired, where connector structures of interest include, but are not limited to: IS-1 connectors, Association for the Advancement of Medical Instrumentation Electrocardiographic (AAMI ECG) cord connectors, and medical grade shrouded multi-pin connectors. In some instances, the connector includes one or more electrodes, such as two to ten electrodes, including three electrodes or four electrodes.

Where desired, the multi-purpose connector may be configured to connect directly with a patient or other external device, such that no additional connector device is required to provide connection between the multi-purpose connector of the receiver and the patient or other external device. Alternatively, the multi-purpose connector may be configured to connect to the patient or other external device through a physically distinct connector device, such as a cable or cord. The physically distinct electrical connector may have one termination configured to fit into the multi-purpose connector, and another termination configured to perform a specific purpose, such as connecting to a patient or an external device, such as a battery charger or external programming device. It should be noted that where a receiver connects to a patient via a distinct connector, such as wire, the device is still considered a receiver.

In receivers of the invention, the multi-purpose connector is operatively connected (such as electrically connected, optically connected, etc.) to multiple functional blocks (for example two or more, three or more, four or more, five or more, seven or more, ten or more functional blocks), e.g., as described elsewhere in the present application.

In addition to being configured to connect a patient, the multi-purpose connectors of interest may be configured to connect the receiver to other external devices, including but not limited to external charger devices, external programming devices, data processing devices, modems, keyboards, displays, and/or external storage devices, etc. By using the same connector to connect the receiver to the patient and to other devices, connection of the patient to the receiver while the medical device is connected to another device, such as a charger, is avoided. This configuration enhances patient safety, because it eliminates the possibility that a signal from the other external device, such as the power charger, programming device, data processor, etc., will be transferred to the patient, potentially harming the patient. Using a single connector for multiple functions also makes waterproofing of the device easier because there are fewer openings on the housing of the device.

The receiver of interest may include a router functionally positioned between the multi-purpose connector and one or more of the multiple functional blocks of the device. By "functionally positioned between" is meant that a signal, such as an incoming signal, outgoing signal, or bidirectional signal, will, after passing through the multi-purpose connector, pass through the router before entering one of the multiple functional blocks. The router may be configured to selectively allow signals to pass through to certain functional blocks depending on one or more parameters. For example, the router may be configured to discriminate the signal based on voltage, e.g., allowing only voltage above or below a certain threshold (or within a certain band) to pass through; frequency, e.g., allowing only signals above or below a threshold frequency (or within a certain frequency band) to pass through; or operating mode, e.g., power-charging mode, data transmission mode, patient interactive mode, etc. In some instances, there may be a router functionally positioned between the multi-purpose connector and only some of the multiple functional blocks. In other words, there may be one or more functional blocks that are not separated from the multi-purpose connector by a router.

In some instances, the router may be configured to discriminate signals based on the unique characteristics of the signals of interest to the device. A signal measured from the body may be a relatively low voltage, for example 500 mV or less, such as 100 mV or less, or 50 mV or less. Similarly, a signal measured from the body may be of relatively low frequency, for example 20 kHz or less, such as 5 kHz or less, or 1 kHz or less. In comparison, a typical power signal used to recharge the internal battery of a device such as the external medical device may be a relatively higher voltage, such as 1 V or more, 2 V or more, or 5 V or more. A typical signal used for data transmission may have a relatively higher frequency than a body-measured signal, for example 100 kHz or more, such as 1 MHz or more, or 10 MHz or more. Thus, by distinguishing based on frequency and voltage, the router can selectively route a signal to the appropriate functional block or blocks. A router may discriminate the signal based on any characteristic of the signal, including but not limited to voltage, frequency, and the combination of the two. In other instances, the router can route the incoming signal based on the operating mode of the device, which may be set by other circuitry, by software, or by a manual switch or command.

In certain instances, the router is configured to route a certain type of signal to a particular functional block while isolating the signal from one or more other functional blocks. For example, if it is desired to make a high impedance measurement of the signal from the patient, it can be important to isolate the low impedance of the power functional block. In this case, a router can be placed between the power functional block and the multi-purpose connector which only allows a signal above a certain voltage to pass through. Thus, the relatively low voltage of a signal measured from the patient's body will be isolated from the power functional block, and the patient interactive functional block will be able to properly measure the signal.

However, in some instances, it may not be important to isolate a particular block from the other functional blocks when it is not being used. As such, in some instances the router may not be configured to disconnect one or more particular functional blocks from the signal. That is, in these instances, the incoming signal will always pass to a particular functional block. However, in some cases, the functional block may only respond to certain types of signals, such as a certain range of frequency or voltage, and will not suffer harm when exposed to other signals. This selective responsiveness may effectively act as a routing means.

The router, as used here, may itself be made up of multiple functional routing blocks, each one functionally positioned between one or more of the device functional blocks and the multi-purpose connector. In this way, the individual router blocks may discriminate the signal based on different parameters, allowing a different class of signal to reach the respective device functional blocks.

The router may route signals to the appropriate circuitry either inherently, actively, or by a combination of inherent and active techniques. In some instances, the routers may discriminate the incoming signal based on voltage. For example, a router functionally positioned between the multiple-purpose connector and one or more of the functional blocks may allow only a signal above a certain voltage threshold to pass through to those functional blocks. In some instances this may be done with one or more diodes. In some instances, the diodes may be arranged as a rectifier, e.g., a half-wave rectifier, full-wave rectifier, three phase rectifier, etc. In other instances, the router may allow only a signal below a certain threshold voltage to pass through to the associated functional blocks.

In other instances, the router may route signals based on frequency. For example, a router functionally positioned between the multiple-purpose connector and one or more of the functional blocks may allow only a signal above a certain frequency to pass through to the associated functional blocks. In other instances, the router may allow only a signal below a certain frequency, within a certain frequency band, or outside of a certain frequency band to pass through. A router that discriminates based on frequency may contain a filter, such as a low-pass filter, a high-pass filter, or a band-pass filter. The filter may have any convenient design, and the filter characteristics may vary depending on the characteristics of the signals that need to be distinguished.

In some aspects, the router may contain one or more controlled switches that route the signal to the appropriate functional blocks. The switches may include, but are not limited to, analog switches, a multiplexer, relays, etc., or any combination of these. The switches may be controlled by other circuitry which detects the signal present and routes it accordingly. Alternatively, the switches may be controlled by software. In other aspects, the switches may be controlled by the user. For example, there may be a user interface on the housing of the device or on an external controller. The user interface may include, but is not limited to one or more switches, one or more buttons, a touchscreen, etc. by which the user can select the appropriate operating mode and the router switches can be set accordingly. In some instances, the operating mode of the device can be modified by the internal circuitry or software based on the signal input from the multi-purpose connector. The potential operating modes may include, but are not limited to, patient interactive mode, power charging mode, data communication mode, etc. The switches may then be routed according to the operating mode.

In some instances where data or processing commands are to be sent through the multiple-purpose connector, it may be desirable to select a signaling protocol that is compatible with the patient connection circuitry. To comply with regulatory requirements, the patient electrical connections may have safety capacitors connected to the electrical connections to protect the patient from DC voltages. In these aspects, it may be desirable to select a communication protocol that does not rely on DC levels to represent the data bits, i.e., a 1 or a 0. Instead, a data communication protocol may be chosen that relies on transitions or frequency modulation to represent the data. In other instances, it may not be necessary to avoid a DC data protocol, and any convenient data protocol may be used.

A block diagram of a receiver comprising a multi-purpose connector is shown in FIG. 16, where the device is shown in patient interactive mode. Receiver 1601 is connected to patient 1603 through multi-purpose connector 1605. Multi-purpose connector 1605 is located on housing 1607 and is connected to router 1609. Router 1609 connects to internal power source 1611, signal acquisition block 1613, energy output block 1615, and/or controller and data input/output block 1617. As shown, the receiver 1601 is connected to a patient 1603, and thus the router 1609 passes a signal to signal acquisition block 1613 via connection 1619. Energy can be delivered to the patient by energy output block 1615 through connection 1621. Connection 1621 may or may not share the same electrical lines as connection 1619.

The same receiver is shown in FIG. 17, where the device is shown in power charging mode. External power source 1723 is connected to receiver 1701 through multi-purpose connector 1705. Multi-purpose connector 1705 is connected to router 1709. Router 1709 recognizes that the incoming signal is a power charging signal, and accordingly routes the signal to internal power source 1711 through connection 1725, thus charging internal power source 1711.

Figure 18:
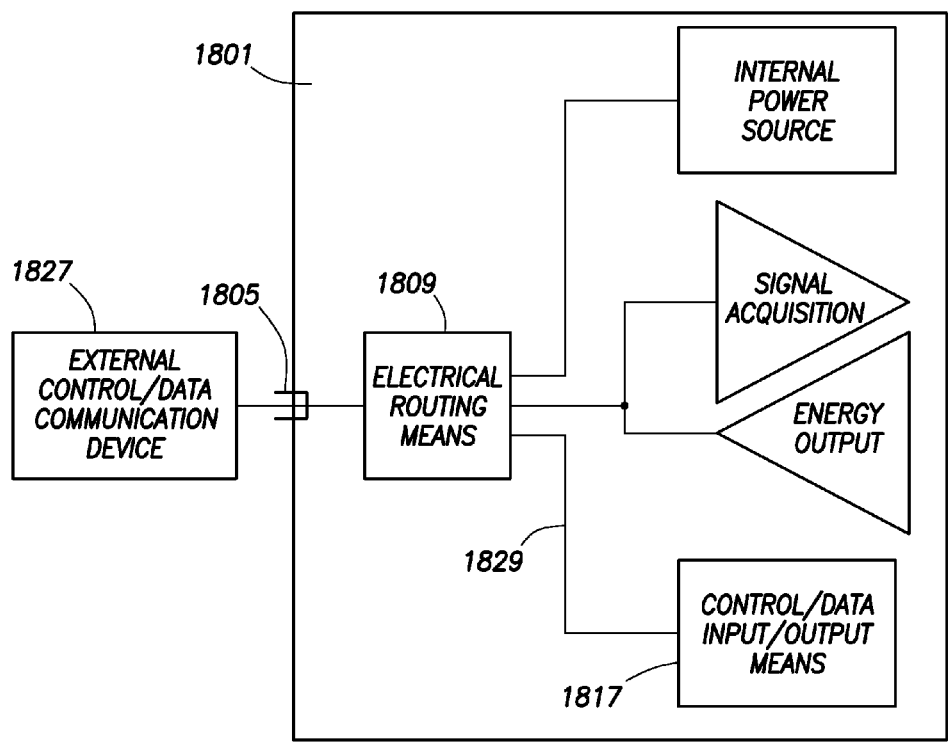
FIG. 18 provides a block diagram showing a receiver connected to an external control and data communication device.

FIG. 18 shows receiver 1801 when the device is in data communication mode. External control and data communication device 1827 is connected to receiver 1801 through multi-purpose connector 1805. Multi-purpose connector 1805 is connected to router 1809. Router 1809 recognizes the incoming signal as a control and/or data communication signal, and accordingly routes the signal to control and data input/output block 1817 along connection 1829. External control and data communication device 1827 may then send a control signal and/or data packet to control and data input/output block 1817 or send a signal requesting data from control and data input/output block 1817. Control and data input/output block 1819 may send data to external control and data communication device 1827 over the same connection 1829, or over a different connection, including a wireless connection.

An example of a router which can be employed in receivers of the invention is shown in FIGS. 19A and 19B. FIG. 19A depicts a router that discriminates the signal based on voltage level. Only signals that exceed the threshold voltage of router 1931 will be passed from bus 1933 to bus 1935. A simple example of this principle is shown in FIG. 19B, in which diode 1937 acts as the signal director, e.g., router 1909. Only signals which are greater than the threshold voltage of diode 1937 will be passed from bus 1939 to bus 1941.

FIGS. 20A and 20B show examples of routers that discriminate based on the frequency of the incoming signal. FIG. 20A shows the principle of a router based on frequency with incoming signal bus 2043 and functional block busses 2045 and 2047. Element 2049 has an impedance which increases with frequency, and forms a high pass filter with resistor 2050. Only signals above the design frequency of the high-pass filter will be passed from bus 2043 to bus 2045. Element 2051 has an impedance which reduces with frequency, and forms a low pass filter with resistor 2052. Only signals below the design frequency of the low-pass filter will be passed from bus 2043 to bus 2047. The high-pass filter and low-pass filter may or may not have different design frequencies. FIG. 20B shows a simple example of this principle. Capacitor 2053 and resistor 2054 form a high-pass filter between bus 2057 and bus 2059, and inductor 2055 and resistor 2056 form a low-pass filter between bus 2057 and bus 2061. Only those signals above the cutoff frequency are allowed to pass from bus 2057 to bus 2059, while only those signals below the cutoff frequency are allowed to pass from bus 2057 to bus 2061.

FIG. 20C shows another example of a router that discriminates based on the frequency of the incoming signal. High-pass filter 2056 has a gain that drops off below a certain design frequency. Only signals above the design frequency will pass from bus 2058 to bus 2060. Low-pass filter 2062 has a gain that drops off above a second design frequency. Only signals above the design frequency will pass from bus 2058 to bus 2064.

FIG. 21 shows an aspect of the router that employs active switches. Bus 2163 is separated from busses 2165, 2167, and 2169 by switches 2171, 2173, and 2175. Busses 2165, 2167, and 2169 each connect to one or more functional blocks of the external receiver. Switches 2171, 2173, and 2175 may be controlled by other circuitry, software, and/or by the user to open or close as needed to connect or disconnect bus 2163 to the corresponding functional block.

Receivers of the invention may incorporate circuitry connected to a multi-purpose connector which inherently routes an applied AC voltage, which is above a certain threshold, to a rectifying means, a power conversion means, and then to a battery charger circuit which uses the energy to charge the internal battery. The data acquisition circuitry inside the receiver is immune to the specified applied AC voltage. The receiver also detects the presence of this voltage and can change its operating mode based on that information.

Figure 22A:
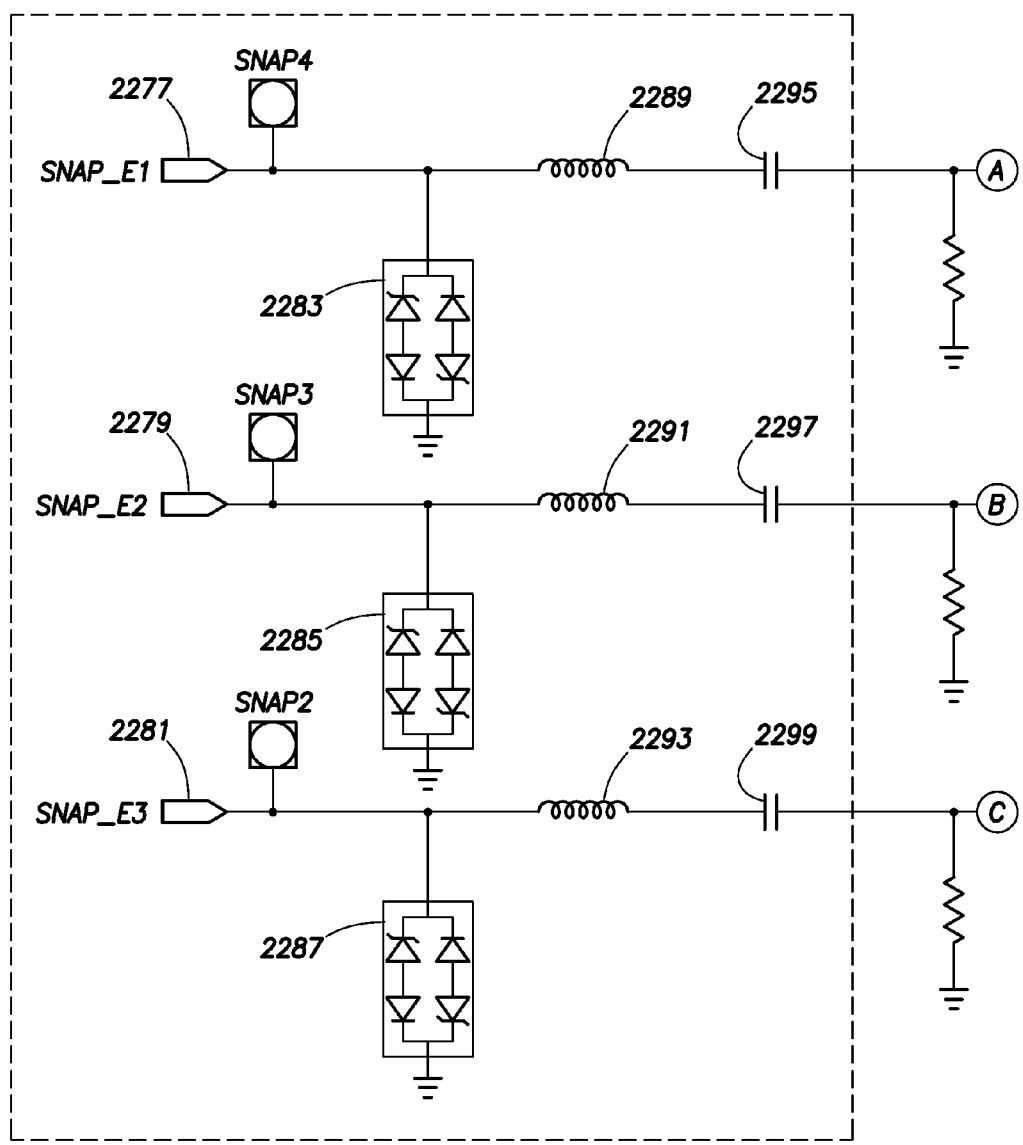
FIGS. 22A-C (referred to collectively as FIG. 22) provide a circuit schematic for multi-purpose electrode connections in accordance with an aspect of the invention.
Figure 22B:
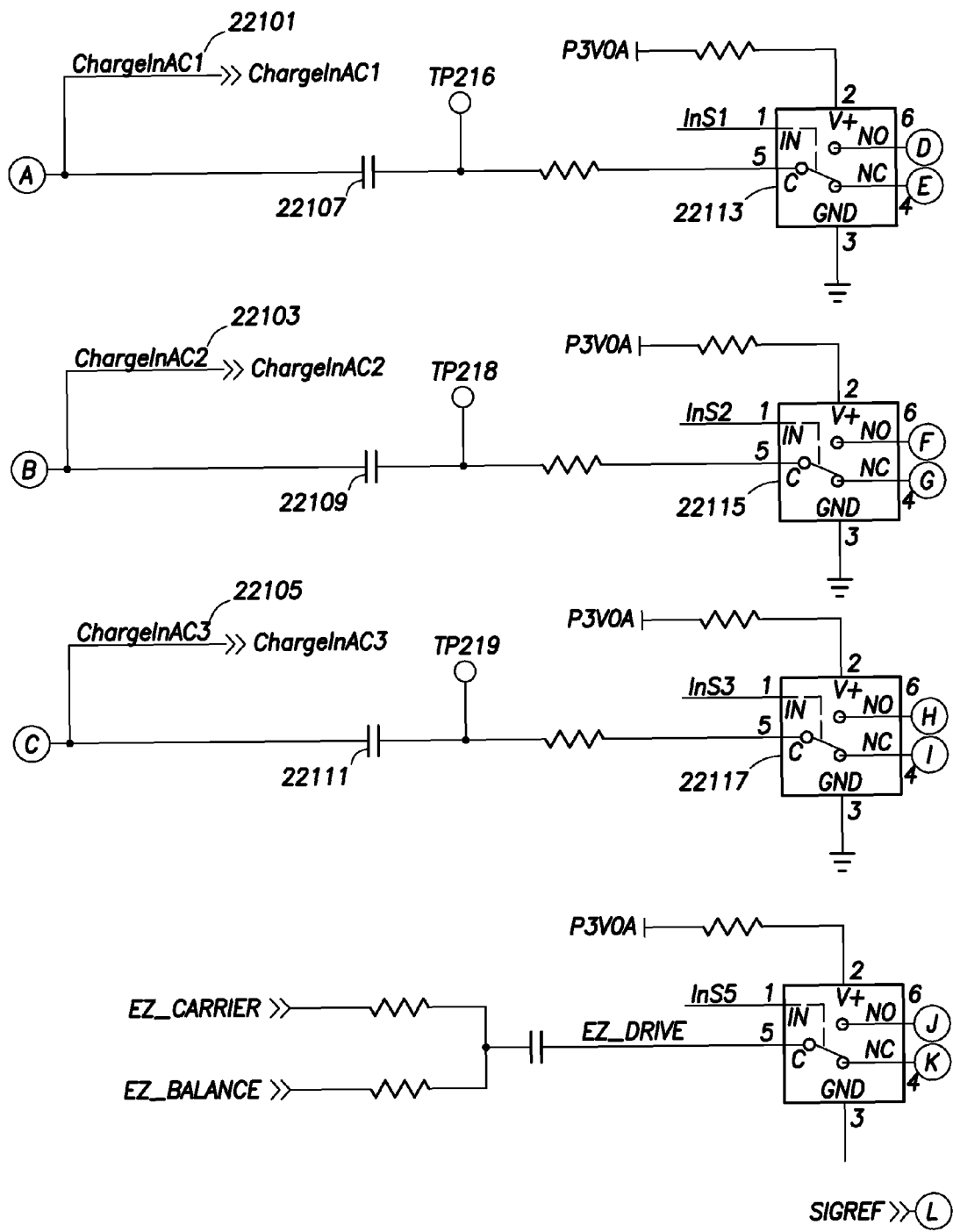
Figure 22C:
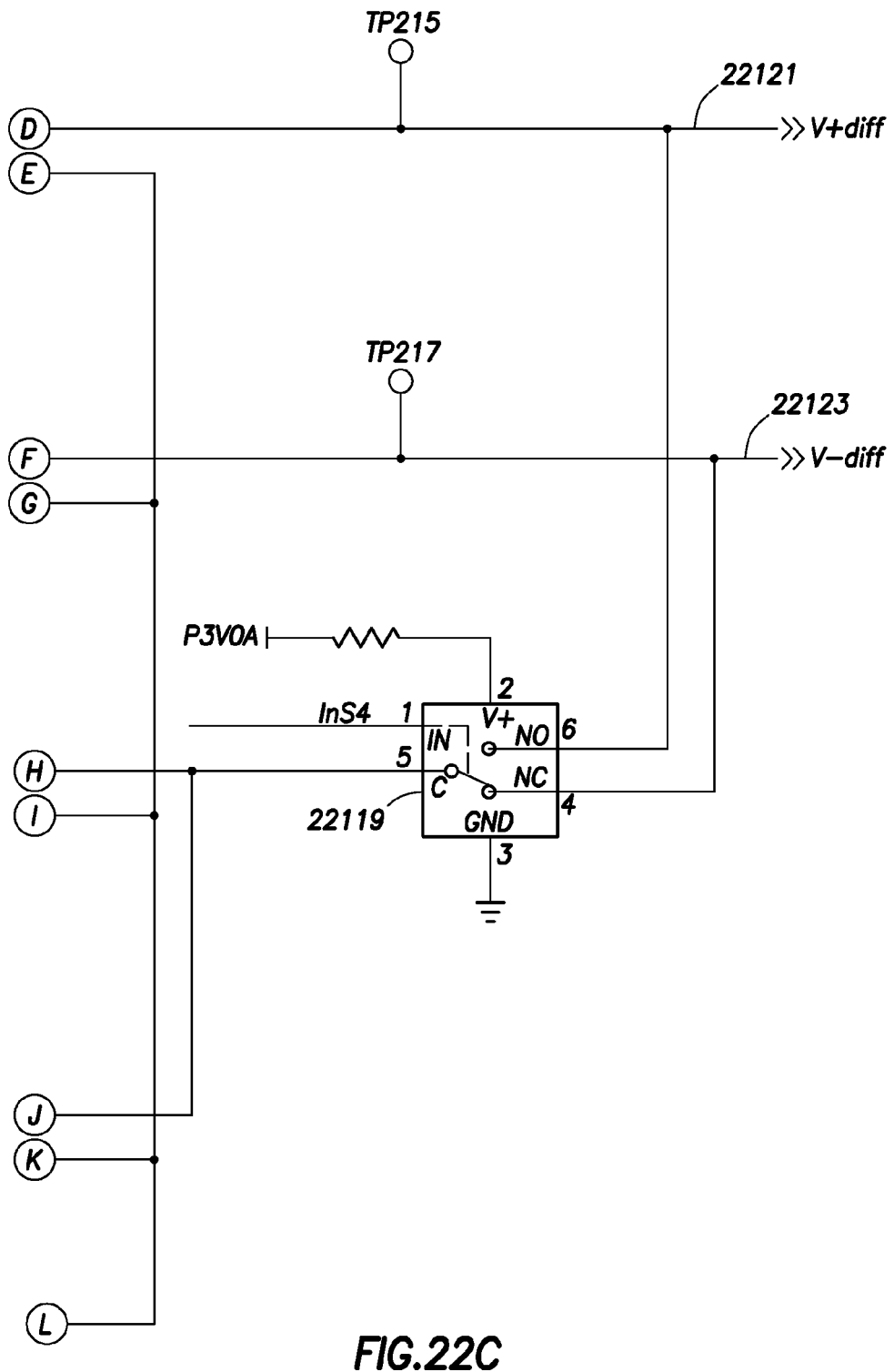
Figure 23A:
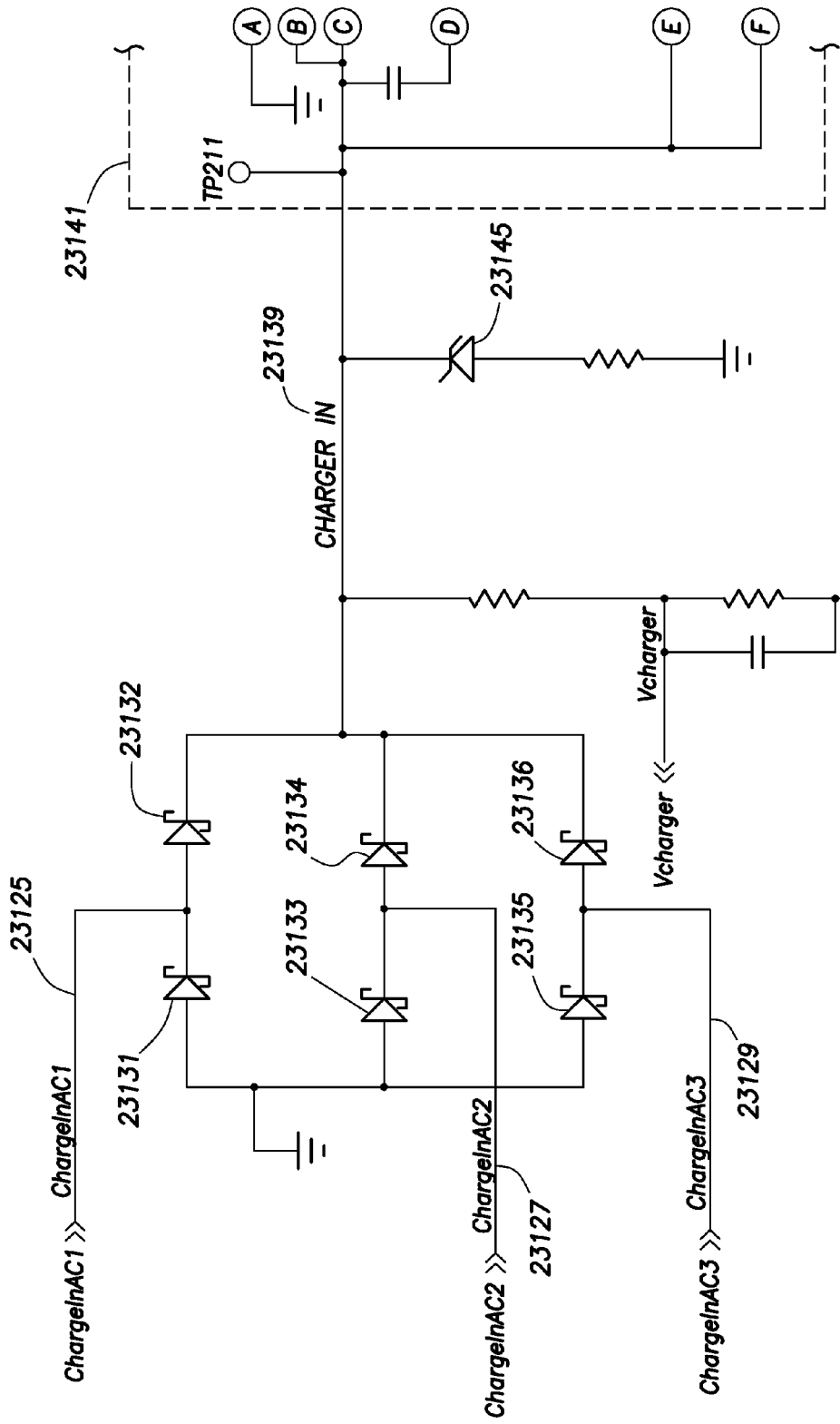
FIGS. 23A-B (referred to collectively as FIG. 23) provide a circuit schematic for an internal power source block of an external receiver in accordance with an aspect of the invention.
Figure 23B:
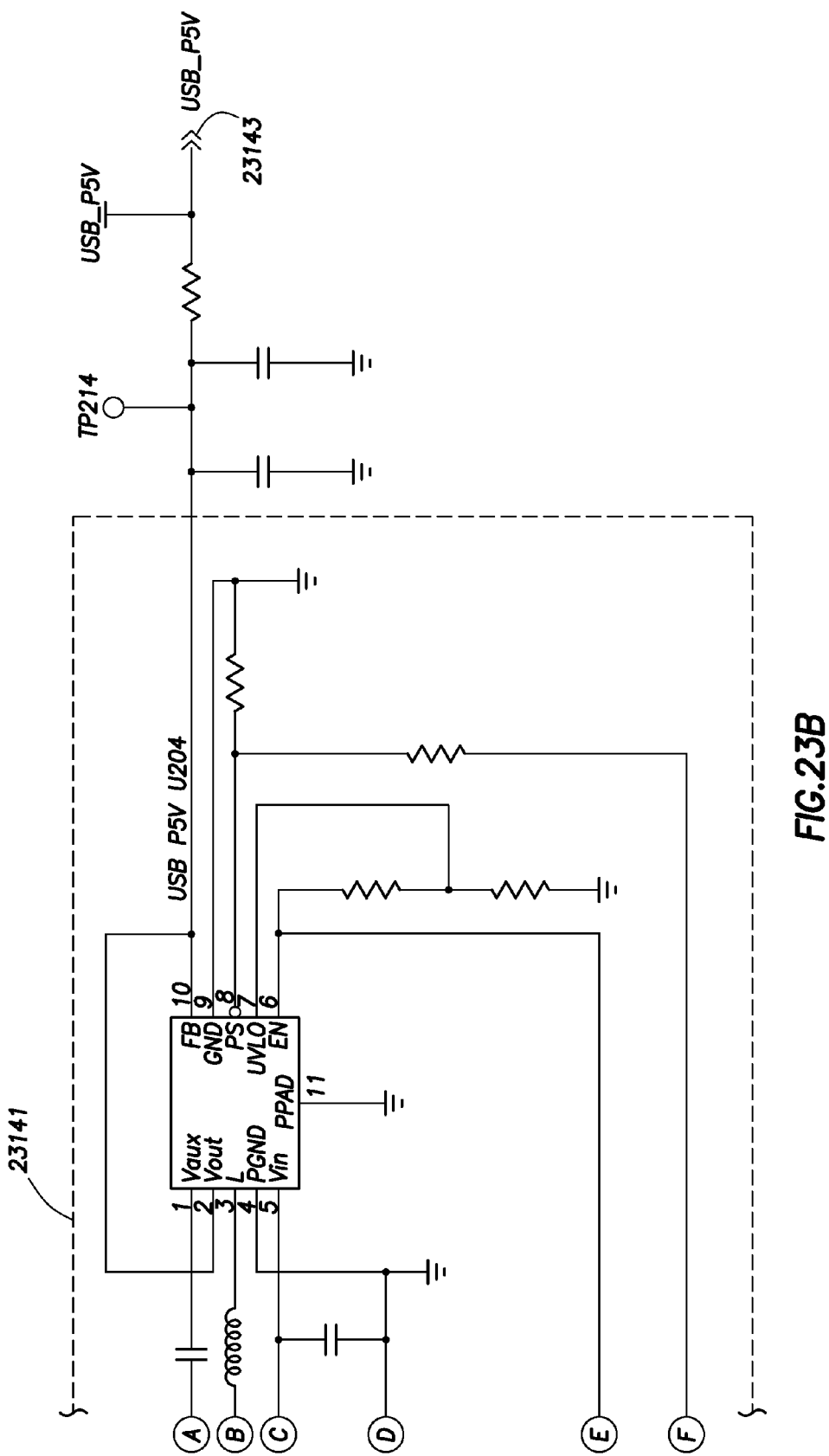
Figure 24A:
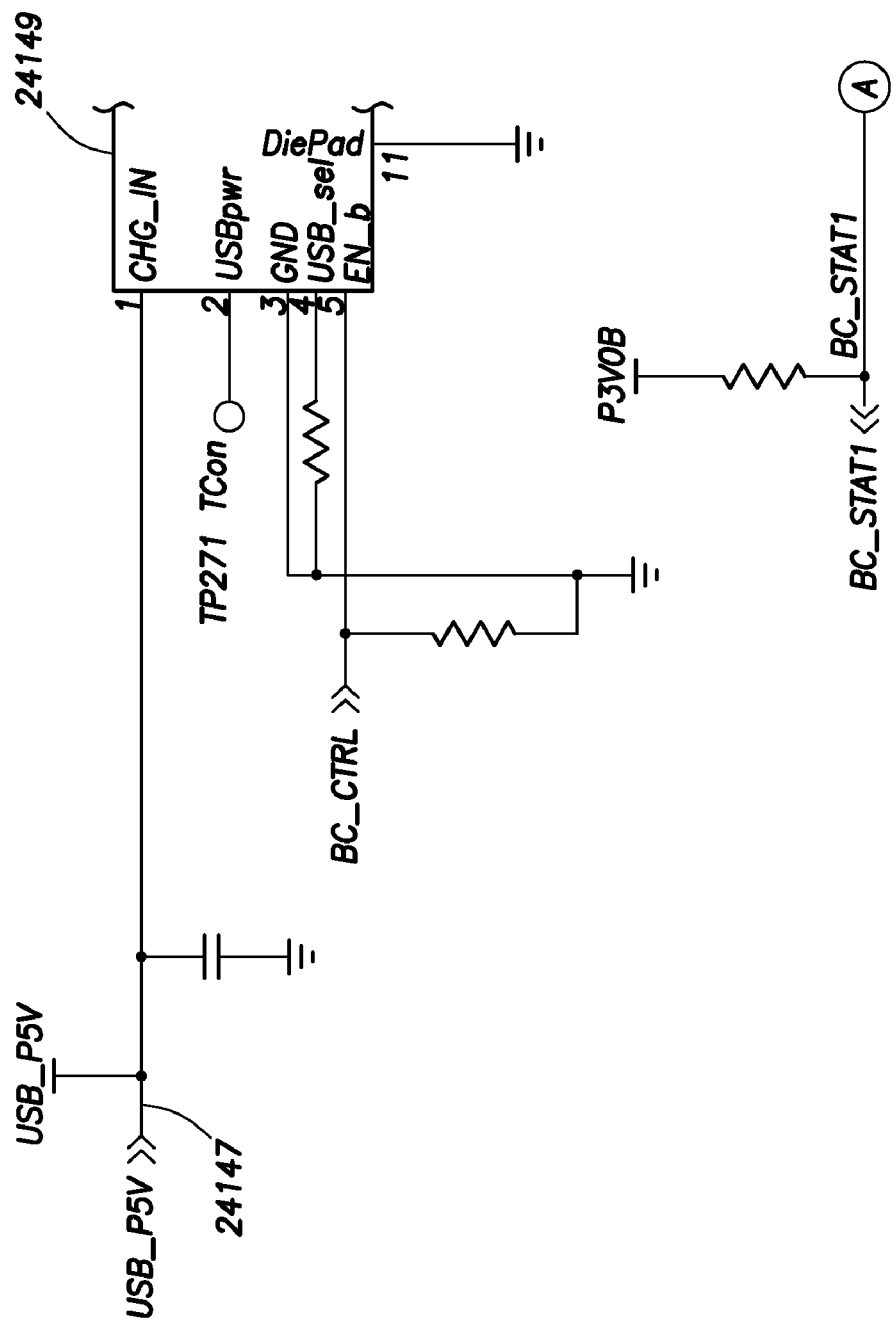
FIGS. 24A-C (referred to collectively as FIG. 24) provide a circuit schematic for an internal power source block of an external receiver in accordance with an aspect of the invention FIG. 25 provides a schematic of component/functionality relationships.
Figure 24B:
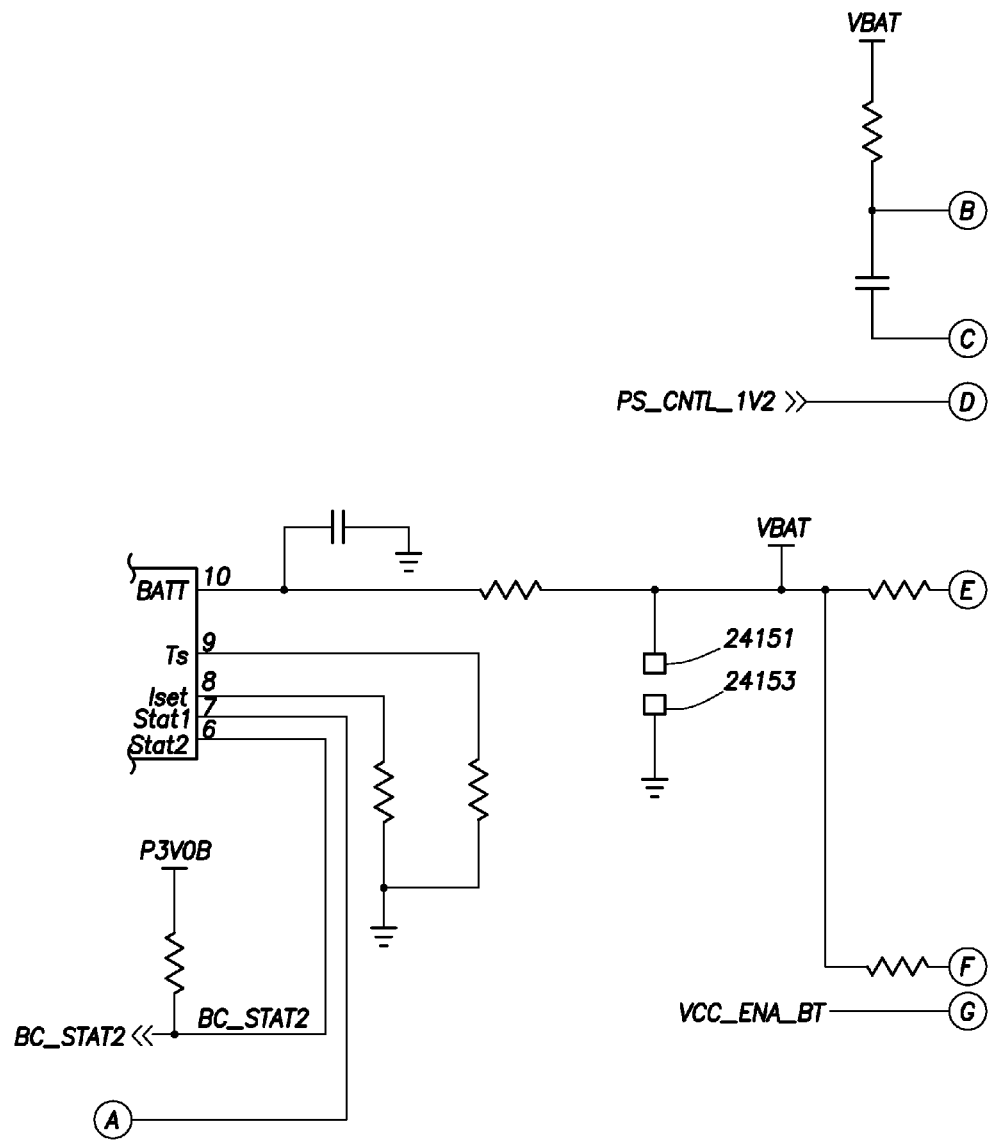
Figure 24C:
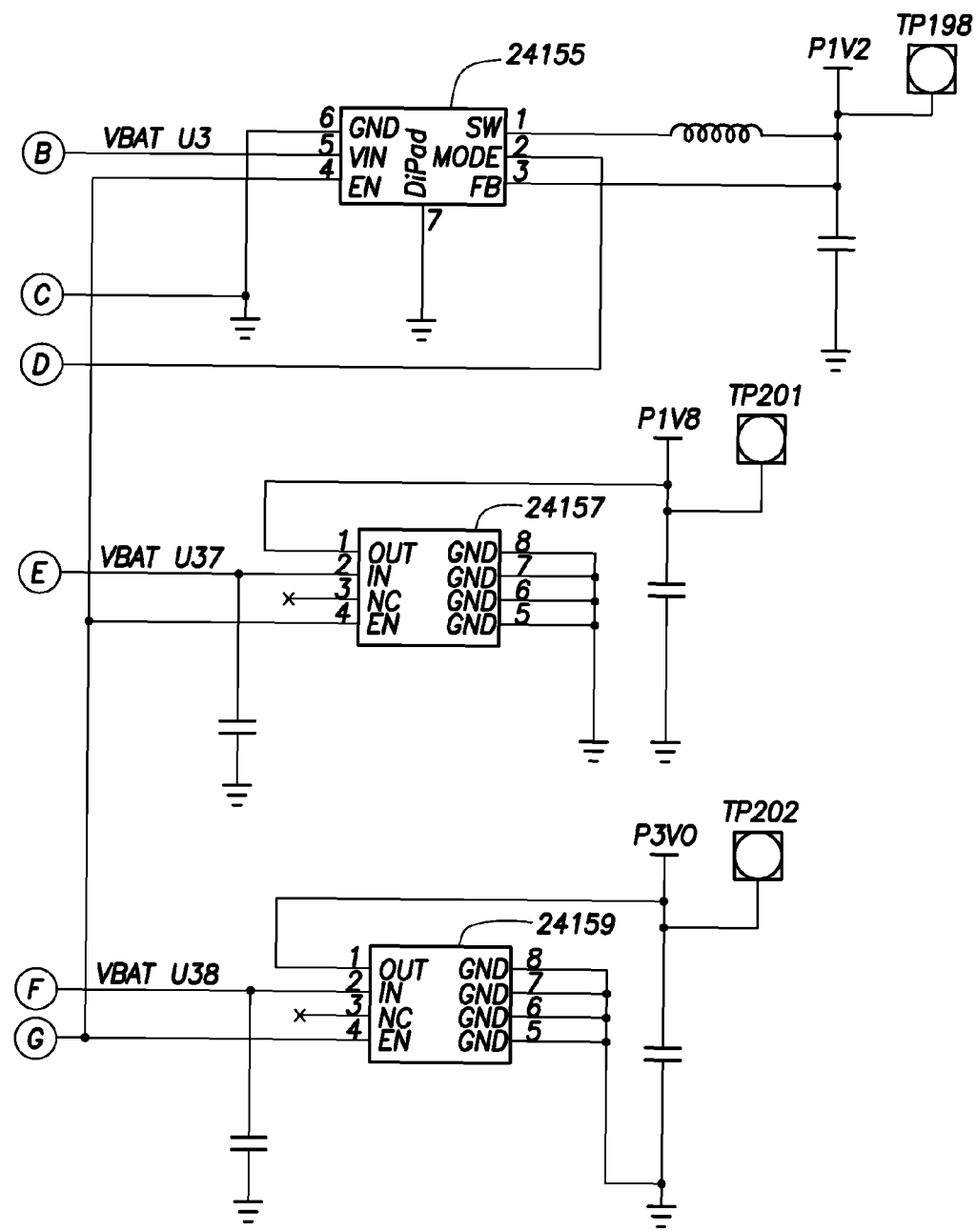

FIGS. 22-24 show one example of circuitry for an aspect of the receiver. FIG. 22 shows the multi-purpose electrode connections SNAP_E1 2277, SNAP_E2 2279, and SNAP_E3 2281, along with switches 22113, 22115, and 22117 which connect the electrodes to the signal reception block through signal reception amplifier inputs 22121 and 22123. Diodes 2283, 2285, and 2287 protect the circuitry from damage due to electrostatic discharge (ESD). Inductors 2289, 2291, and 2293 reduce electromagnetic interference (EMI). Capacitors 2295, 2297, and 2299 protect the patient by preventing any DC voltage from being applied to electrodes 2277, 2279, and 2281. Lines ChargeInAC1 22101, ChargeInAC2 22103, and ChargeInAC3 22105 connect the inputs to the internal power source which is shown in a subsequent figure. Capacitors 22107, 22109, and 22111 prevent any DC voltage from being applied to the signal reception amplifier. Switches 22113, 22115, 22117, and 22119 are used to select any combination of the three electrodes 2277, 2279, and 2281 to go to the two signal reception amplifier inputs V+diff 22121 and V−diff 22123.

In the device shown in FIG. 22, it is not possible to disconnect the signal reception block completely. If a power charging signal is applied to the electrodes, it will be passed through the switches and on to the amplifier inputs. However, the amplifier inputs are designed to be immune to the relatively large voltage, so disconnecting the signal reception block is unnecessary.

In an alternative configuration, it may be possible to disconnect the signal reception block when a signal other than a data signal is received on the electrodes. This may be accomplished, for example, by using additional switches and/or a different arrangement of switches.

The battery charger inputs to the internal power source functional block are shown in FIG. 23. Lines ChargeInAC1 22101, ChargeInAC2 22103, and ChargeInAC3 22103 from FIG. 22 connect to the power source functional block at ChargeInAC1 23125, ChargeInAC2 23127, and ChargeInAC3 23129, respectively. Diodes 23131-23136 form a three-phase rectifier. When the device is connected to an external power charger, the rectifier takes the power charging signal, which may be an alternating current, e.g., a 100 kHz square wave, and converts it to a DC current on net Charger_In 23139. When the voltage present on the inputs is less than about 0.6 V, such as when the device is connected to a patient, the signal is not passed through the rectifier and Charger_In node 23139 is disconnected from inputs 23125, 23127, and 23129. This isolates the low impedance of Charger_In node 23139 from the electrodes when it is needed to make a high impedance measurement of the signal on the patient. Boost converter 23141 boosts the voltage on net Charger_In 23139 to the desired power charging voltage, e.g., about 5V. The boosted voltage is passed on to the battery charger through node 23143. Diode 23145 protects the circuit in case a higher than desired voltage is placed on Charger_In node 23139.

An aspect of the battery charger circuitry is shown in FIG. 24. Output node 23143 from FIG. 23 connects with the battery charger circuit in FIG. 24 at battery charger input node 24147. Battery charger input 24147 connects to battery charger integrated circuit 24149. In this aspect, battery charger input 24147 is configured to recharge a battery, e.g., a lithium battery, at battery pads 24151 and 24153. The rest of the circuitry shown in FIG. 24 includes regulators 24155, 24157 and 24159 which condition the battery voltage for use in the rest of the circuitry in the device.

During use, the receiver may be operatively coupled to either a living subject, such as a patient, or another external device via the multi-purpose connector. Other external devices which may be connected include, but are not limited to, an external power charger device, an external programming device, an external data processing device. The receiver may also be operatively coupled to another medical device via the multi-purpose connector, including to the external proximal end of an implanted medical device. When the patient or another device is connected to the external medical device via the multi-purpose connector, when present the router may open and close signal pathways based on the type of signal or characteristics of the signal. As discussed above, the routing may be done inherently, actively, or by a combination of these and other techniques.

Figure 25:
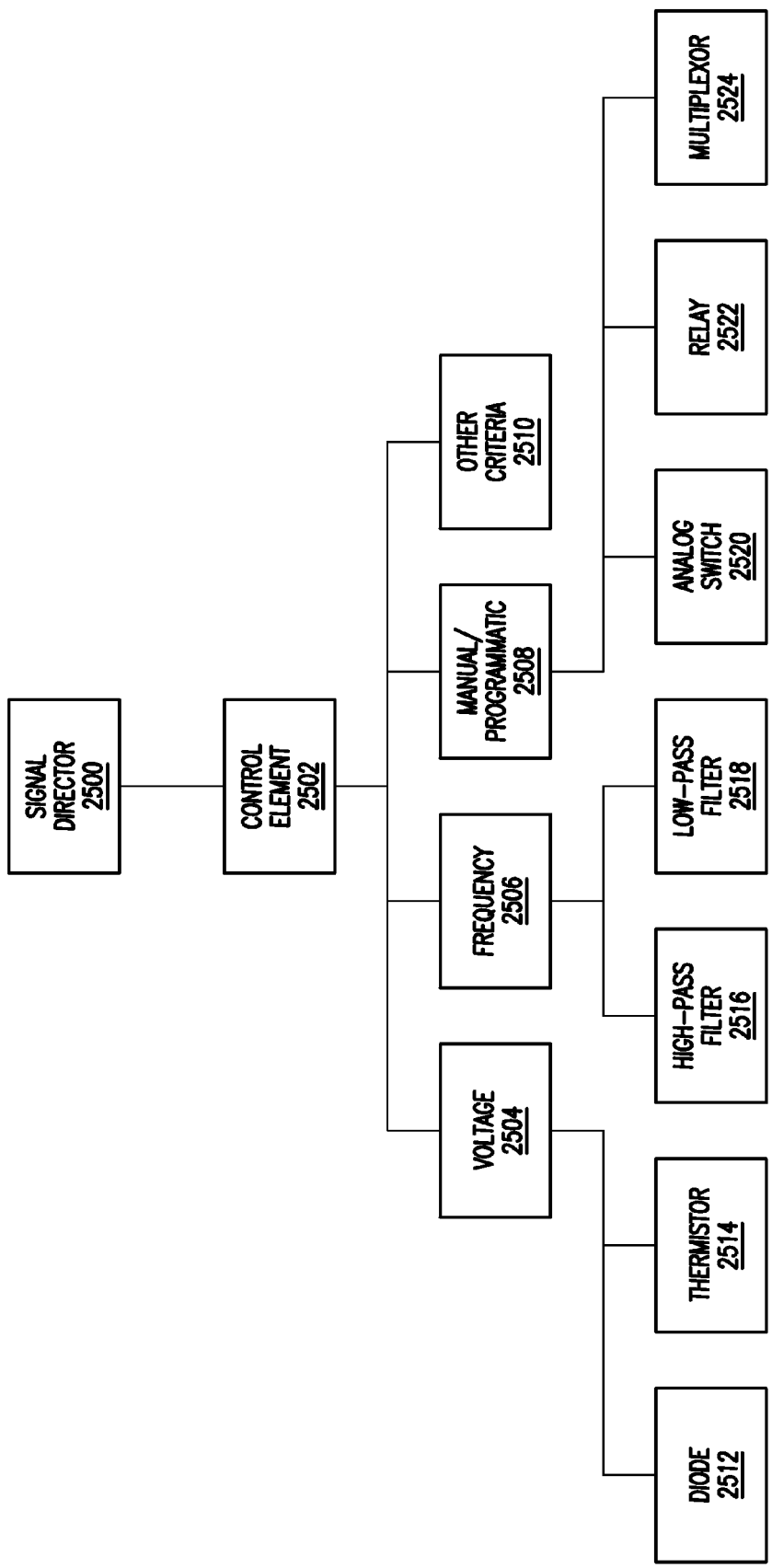

FIG. 25 provides a schematic of component/functionality relationships that may be achieved in aspects that have multi-purpose connectors. The schematic, for example, provides for a signal director 2500. The signal director 2500 comprises a control element 2502. The control element 2502 may control, or be responsive to, voltage 2504, frequency 2506, manual/programmatic commands 2508, and other criteria 2510. The voltage 2504 may be discriminated via one or more diodes 2512, a thermistor 2514, etc. The frequency 2506 may be discriminated by a high-pass filter 2516, a low-pass filter 2518, etc. Signals may be manually and/or programmatically controlled by manual/programmatic commands 2508 via analog switches 2520, a relay 2522, a multiplexor 2524, etc. Other criteria 2510 for signal control/response may include, for example, light, temperature, time, etc.

Methods of using devices with multi-purpose connectors of the invention also include disconnecting the receiver from either the patient or one of the other devices discussed above, and operatively coupling the device to another one of either the patient or one of the other devices via the multi-purpose connector. When present, the router in the receiver may route the signal from the second connected device differently than the signal from the first connected device. In addition, the operating mode of the external medical device may change in response to the signal from the second connected device.

Further details regarding receivers that may include multi-purpose connectors of the invention and methods of their use may be found in U.S. Provisional Patent Application Ser. No. 61/122,723 filed on Dec. 15, 2008; the disclosure of which is herein incorporated by reference.

Impedance (EZ) Measurement Module

Receivers of the invention may include an impedance measurement module, for example where the devices are configured to measure impedance across at least a pair of electrodes of the device. Impedance measurement modules may be configured to determine the loop impedance of the series combination of two electrodes and a resistive load (for example as provided by intervening tissue). The impedance measurement module comprises a current source block to provide current across the electrodes, and a voltage processing block to measure the voltage signal across the resistive load and to determine the electrode impedance. For example, the receiver may be configured to apply a 2 µApp (RMS amplitude is 1 µArms) square wave current across its two electrodes. This is sufficient to detect a detached electrode. Applications may include, but are not limited to receiver diagnostic applications, e.g., where measured impedance is employed to determine if an electrode is disconnected from the patient and/or is not working, patient monitoring applications, such as where impedance is employed to determine one or more physiological parameters, etc.

Figure 27:
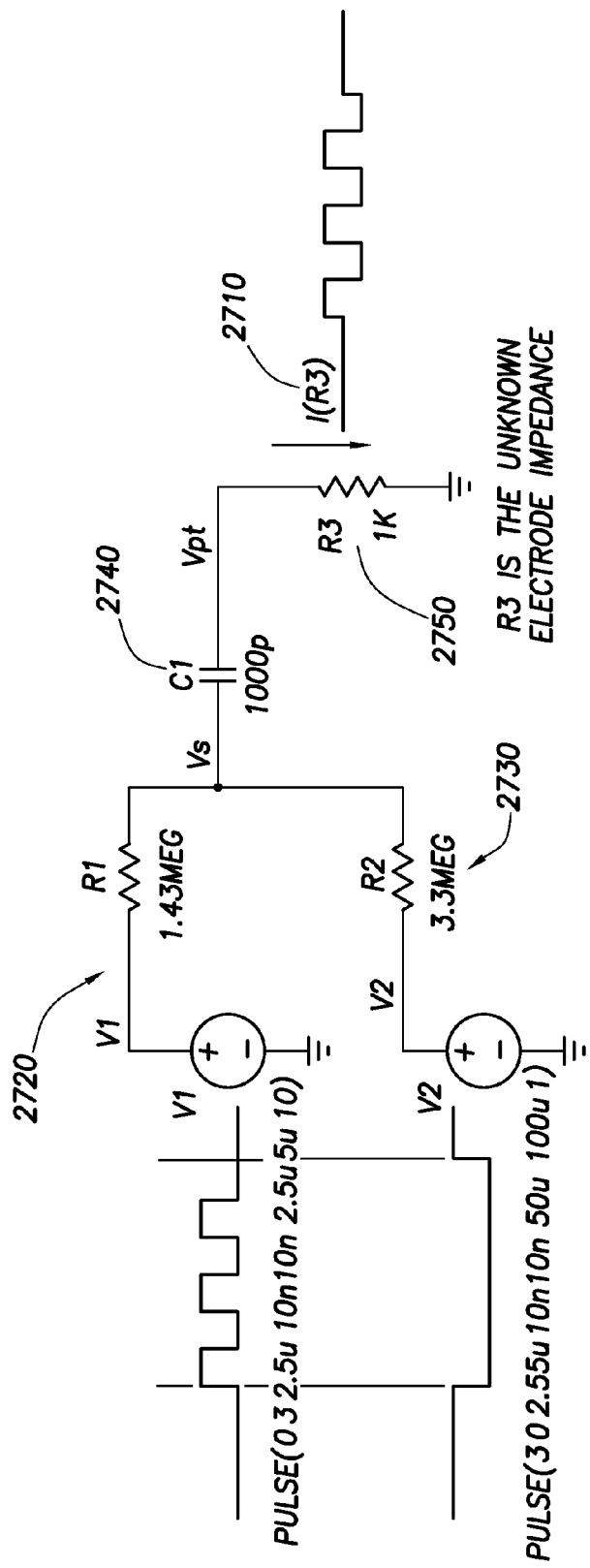
FIG. 27 provides a circuit diagram modeling the drive scheme in an electrode impedance measurement module, according to one aspect.

FIG. 27 provides a circuit diagram modeling a drive scheme 2700 implemented by the current source block, according to one aspect of the invention. As shown in this aspect, a bipolar current may be derived from a unipolar logic drive, with no "DC" component in the drive scheme. Two currents, "EZ_Carrier" 2720 and "EZ_Balance" 2730, are generated and provide an electrode current Iez 2710 across the two electrodes. "EZ_Carrier" 2720 and "EZ_Balance" 2730 may, for example, be generated by the low power processor (e.g., microprocessor), and implemented together in series with capacitor 2740 and resistor 2750 (the unknown electrode impedance).

The voltage processing block measures a voltage signal 2760 across the electrodes (i.e., across the resistive load—resistor 2710) resulting from electrode current Iez 2710. The voltage processing block may then use voltage signal 2710 to determine the electrode impedance. For example, voltage signal 2710 may first be amplified by [Gain=287], band-limited by a 5 KHz HPF and 33 KHZ LPF to reduce noise, and applied to an A/D converter input (e.g., a 12-bit A/D converter sampling at 500 KHz) to provide a digital data stream from the voltage signal. A DSP, for example, may process the digital data stream to determine the electrode impedance. For example, the DSP may mix the input data stream with a sine wave at an EZ Carrier frequency (e.g., 20 KHz), apply a Hogenauer ("CIC") filter to low-pass filter, and decimate (e.g., by 16) the data stream. This moves the fundamental of the carrier energy to 0 Hz. The DSP may then calculate the absolute value (magnitude) of the data stream, average that over a 1 second period, and convert to impedance using the formula:

$$Zelectrode = (Vc/(Iez*Gain)) - 300$$

where: Vc is the measured amplitude at the A/D converter, at the Iez carrier frequency (20 KHz). Gain setting G3 . . . G0=0000; using 287 as the Gain value for calculation. This results in a 300 ohm Tare resistance (electrode impedance) in series with the electrode being measured.

Figure 28:
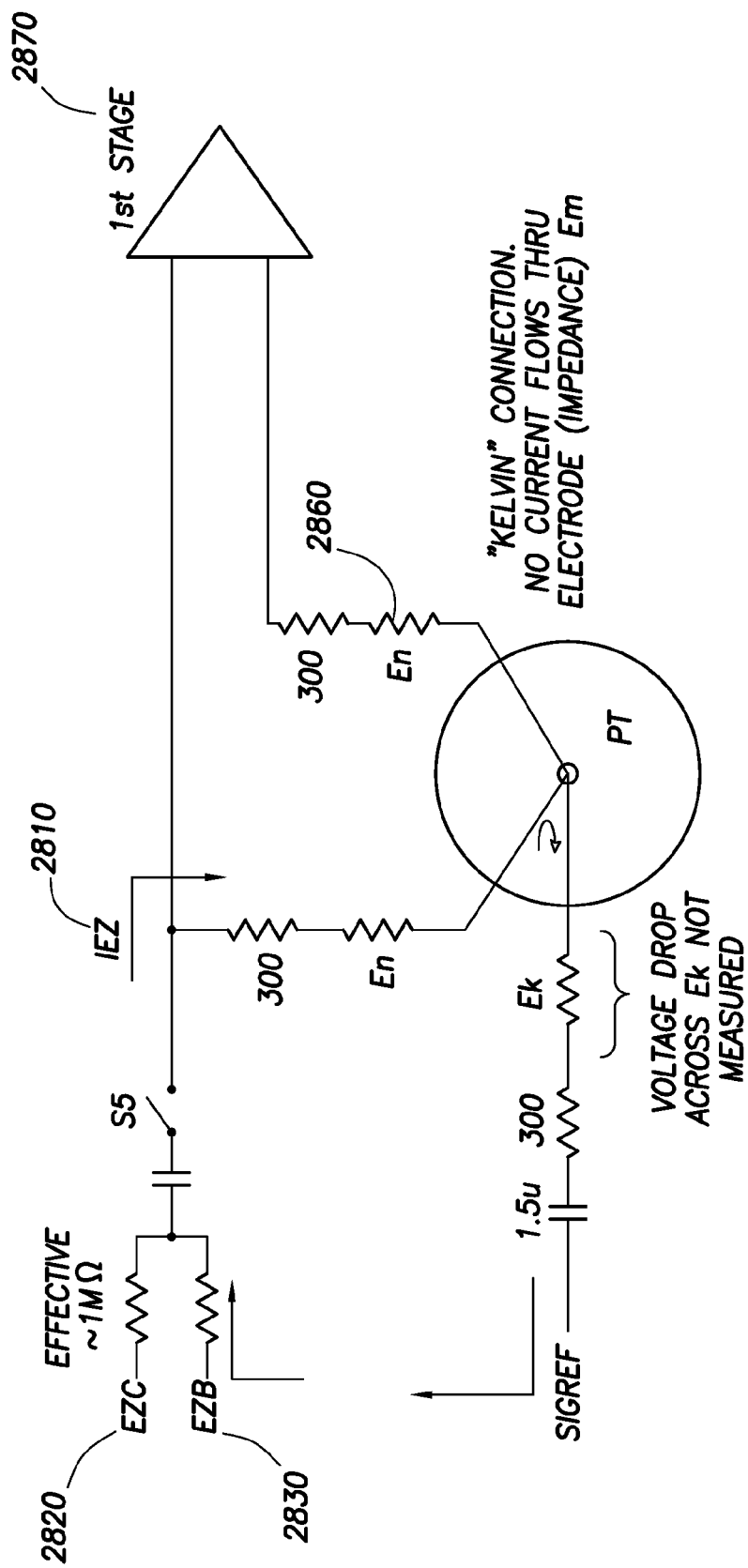
FIG. 28 provides a circuit diagram for an electrode impedance measurement module using a 3-wire ohmmeter, according to one aspect of the invention.

FIG. 28 provides for a circuit diagram for an electrode impedance measurement using a 3-wire ohmmeter, according to one aspect of the invention. Current source block generates EZ carrier line 2820 and EZ Balance line 2830 to provide electrode current (Iez) 2810 flowing through resistive load, electrode resistance En 2850. With a Kelvin connection, and no current flowing through electrode (impedance) Em 2860, the voltage observed by the first stage 2870 will be Iez*(300+En). Electrode current Iez 2810 may be, for example, 2 µApp=1 µARMS.

An impedance measurement module includes a control module, a processing module and electrodes. Impedance measurement is an example of a sensing capability that may be accomplished with any two electrodes of a receiver. In addition to determining functionality of the device and placement thereof, e.g., whether the electrodes are working and/or connected to the subject as desired, physiological data of interest may be derived from the measured impedance. For example, the measured impedance will have some component which is determined by the trans-thoracic impedance, which relates to respiration. In this manner, the impedance data can be employed to obtain the respiratory rate of the subject. The electrodes 2860 may also be employed as sensors of the fluid state of subject. Over time, particularly for a heart failure patient on diuretics, fluid status is a very important quantity. The obtained fluid state can be used to titrate medications and/or provide alerts. In addition to measuring fluid status, impedance measurements could also be used to measure body fat.

Module Implementation

In various aspects, the above described modules, e.g., high power-low power modules, intermediary modules, the transbody conductive communication module, the physiological sensing modules, power supply modules, storage modules, extra-corporeal communications modules, etc., and/or one or a combination of their components, may be implemented as software, e.g., digital signal processing software; hardware, e.g., a circuit; or combinations thereof. As such, additional elements that may be present in the signal receiver include, but are not limited to: a signal demodulator, e.g., for decoding the signal emitted from an IEM; a signal transmitter, e.g., for sending a signal from the signal receiver to an external location; a data storage element, e.g., for storing data regarding a received signal, physiological parameter data, medical record data, etc.; a clock element, e.g., for associating a specific time with an event, such as receipt of a signal; a pre-amplifier; a microprocessor, e.g., for coordinating one or more of the different functionalities of the signal receiver, band-pass filters, etc.

In certain aspects, the modules of the present receivers are present on integrated circuits, where the integrated circuits include a number of distinct functional blocks. Within a given receiver, at least some of, e.g., two or more, up to an including all of, the modules may be present in a single integrated circuit in the receiver (for example, in the form of a system on chip or SOC). By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain aspects of the present invention may be hybrid integrated circuits, which are miniaturized electronic circuits constructed of individual semiconductor devices, as well as passive components, bonded to a substrate or circuit board.

Figure 7:
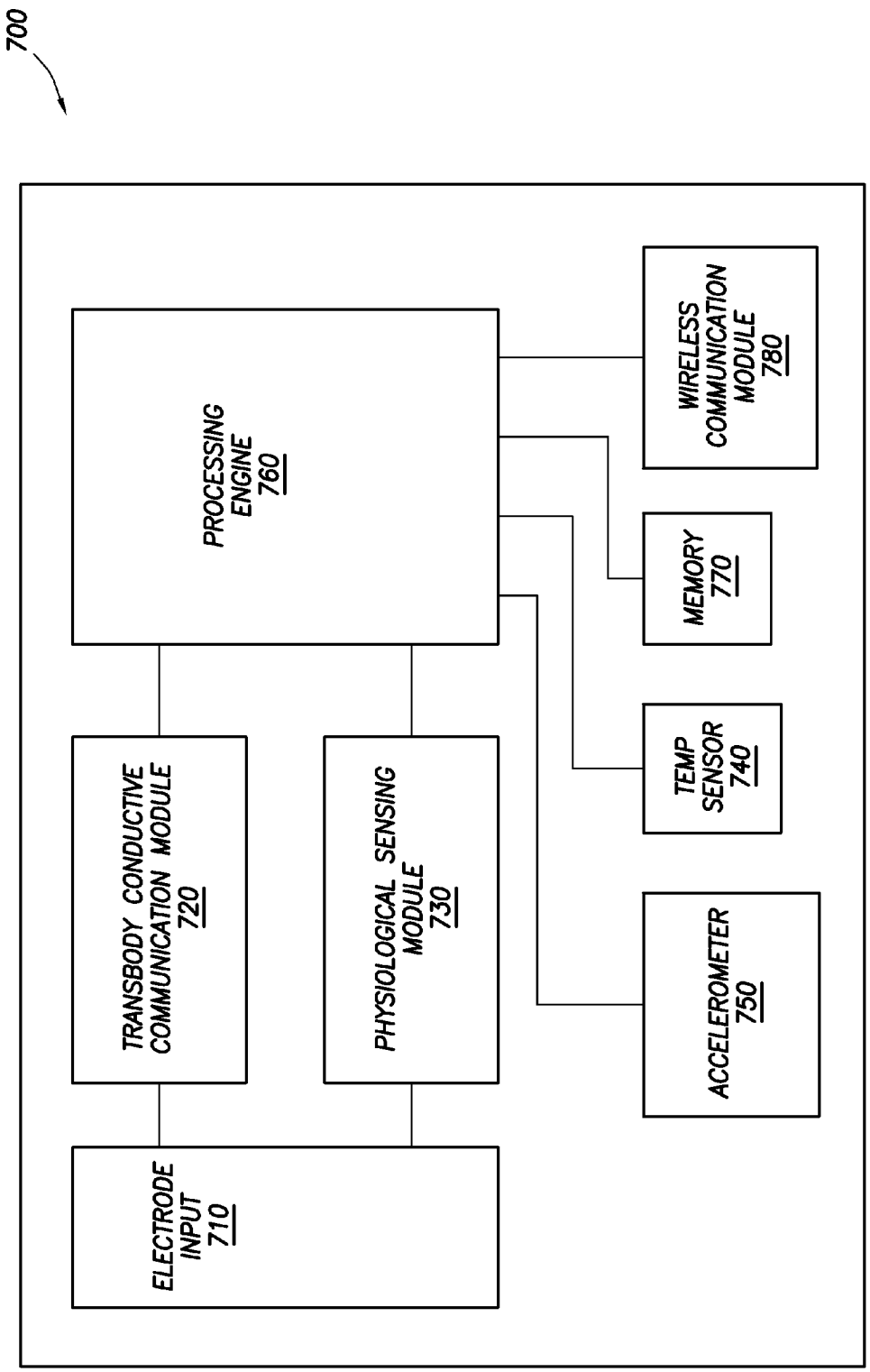
FIG. 7 is a block diagram of the different functional modules that may be present in a receiver, according to one aspect.

FIG. 7 provides a block functional diagram of an integrated circuit component of a signal receiver according to an aspect of the invention. In FIG. 7, receiver 700 includes electrode input 710. Electrically coupled to the electrode input 710 are transbody conductive communication module 720 and physiological sensing module 730. In one aspect, transbody conductive communication module 720 is implemented as a high frequency (HF) signal chain and physiological sensing module 730 is implemented as a low frequency (LF) signal chain. Also shown are CMOS temperature sensing module 740 (for detecting ambient temperature) and a 3-axis accelerometer 750. Receiver 700 also includes a processing engine 760 (for example, a microcontroller and digital signal processor), non-volatile memory 770 (for data storage) and wireless communication module 780 (for data transmission to another device, for example in a data upload action).

Figure 8:
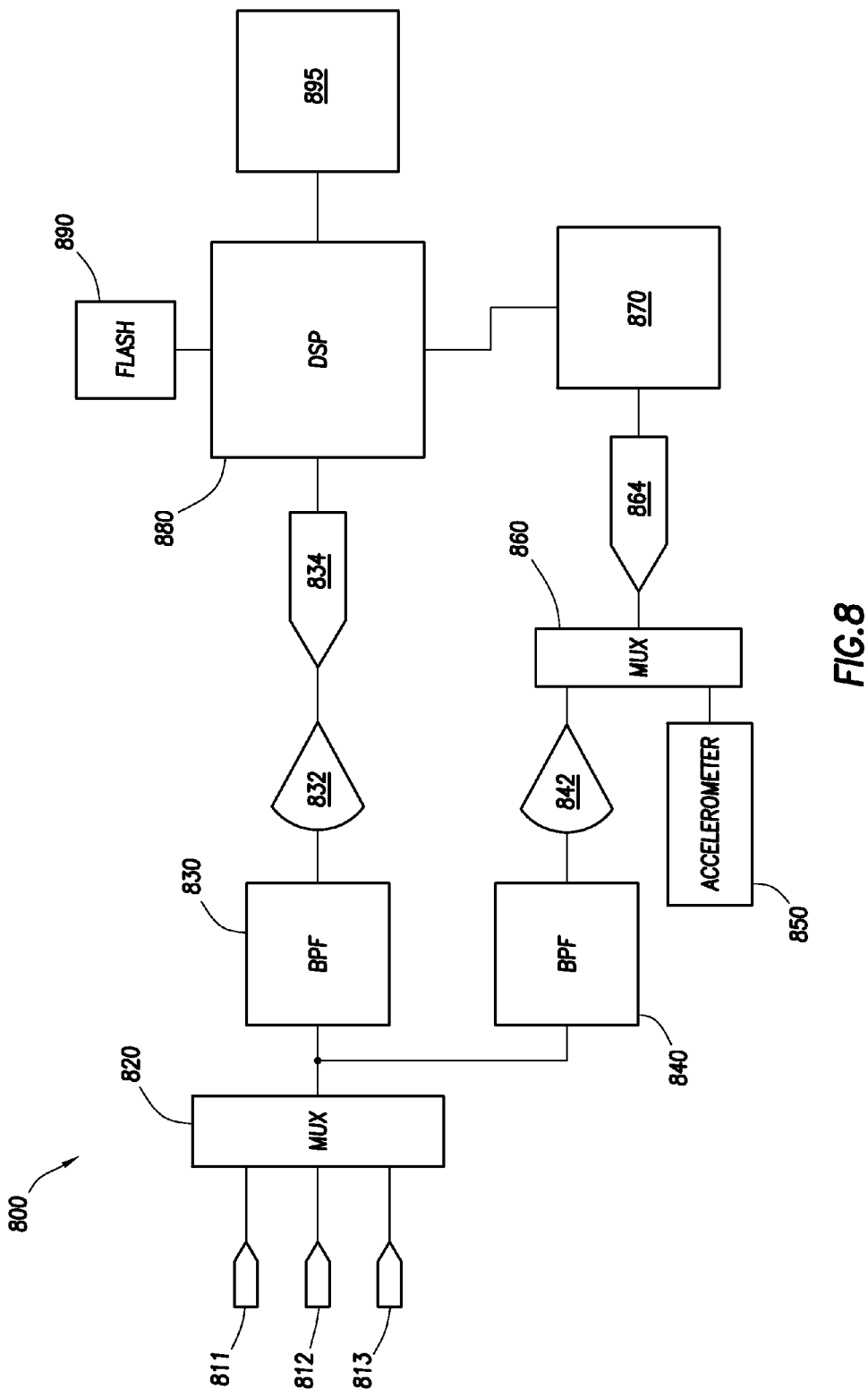
FIG. 8 is a block diagram of a receiver, according to one aspect.

FIG. 8 provides a more detailed block diagram of a circuit configured to implement the block functional diagram of the receiver depicted in FIG. 7, according to one aspect of the invention. In FIG. 8, receiver 800 includes electrodes e1, e2 and e3 (811, 812 and 813) which, for example, receive the conductively transmitted signals by an IEM and/or sense physiological parameters or biomarkers of interest. The signals received by the electrodes 811, 812, and 813 are multiplexed by multiplexer 820 which is electrically coupled to the electrodes.

Multiplexer 820 is electrically coupled to both high band pass filter 830 and low band pass filter 840. The high and low frequency signal chains provide for programmable gain to cover the desired level or range. In this specific aspect, high band pass filter 830 passes frequencies in the 10 KHz to 34 KHz band while filtering out noise from out-of-band frequencies. This high frequency band may vary, and may include, for example, a range of 3 KHz to 300 KHz. The passing frequencies are then amplified by amplifier 832 before being converted into a digital signal by converter 834 for input into high power processor 880 (shown as a DSP) which is electrically coupled to the high frequency signal chain.

Low band pass filter 840 is shown passing lower frequencies in the range of 0.5 Hz to 150 Hz while filtering out out-of-band frequencies. The frequency band may vary, and may include, for example, frequencies less than 300 Hz, such as less than 200 Hz, including less than 150 Hz. The passing frequency signals are amplified by amplifier 842. Also shown is accelerometer 850 electrically coupled to second multiplexer 860. Multiplexer 860 multiplexes the signals from the accelerometer with the amplified signals from amplifier 842. The multiplexed signals are then converted to digital signals by converter 864 which is also electrically coupled to low power processor 870.

In one aspect, a digital accelerometer (such as one manufactured by Analog Devices), may be implemented in place of accelerometer 850. Various advantages may be achieved by using a digital accelerometer. For example, because the signals the digital accelerometer would produce signals already in digital format, the digital accelerometer could bypass converter 864 and electrically couple to the low power microcontroller 870—in which case multiplexer 860 would no longer be required. Also, the digital signal may be configured to turn itself on when detecting motion, further conserving power. In addition, continuous step counting may be implemented. The digital accelerometer may include a FIFO buffer to help control the flow of data sent to the low power processor 870. For instance, data may be buffered in the FIFO until full, at which time the processor may be triggered to turn awaken from an idle state and receive the data.

Low power processor 870 may be, for example, an MSP430 microcontroller from Texas Instruments. Low power processor 870 of receiver 800 maintains the idle state, which as stated earlier, requires minimal current draw—e.g., 10 µA or less, or 1 µA or less.

High power processor 880 may be, for example, a VC5509 digital signal process from Texas Instruments. The high power processor 880 performs the signal processing actions during the active state. These actions, as stated earlier, require larger amounts of current than the idle state—e.g., currents of 30 µA or more, such as 50 µA or more—and may include, for example, actions such as scanning for conductively transmitted signals, processing conductively transmitted signals when received, obtaining and/or processing physiological data, etc.

The receiver may include a hardware accelerator module to process data signals. The hardware accelerator module may be implemented instead of, for example, a DSP. Being a more specialized computation unit, it performs aspects of the signal processing algorithm with fewer transistors (less cost and power) compared to the more general purpose DSP. The blocks of hardware may be used to "accelerate" the performance of important specific function(s). Some architectures for hardware accelerators may be "programmable" via microcode or VLIW assembly. In the course of use, their functions may be accessed by calls to function libraries.

The hardware accelerator (HWA) module comprises an HWA input block to receive an input signal that is to be processed and instructions for processing the input signal; and, an HWA processing block to process the input signal according to the received instructions and to generate a resulting output signal. The resulting output signal may be transmitted as needed by an HWA output block.

Figure 30:
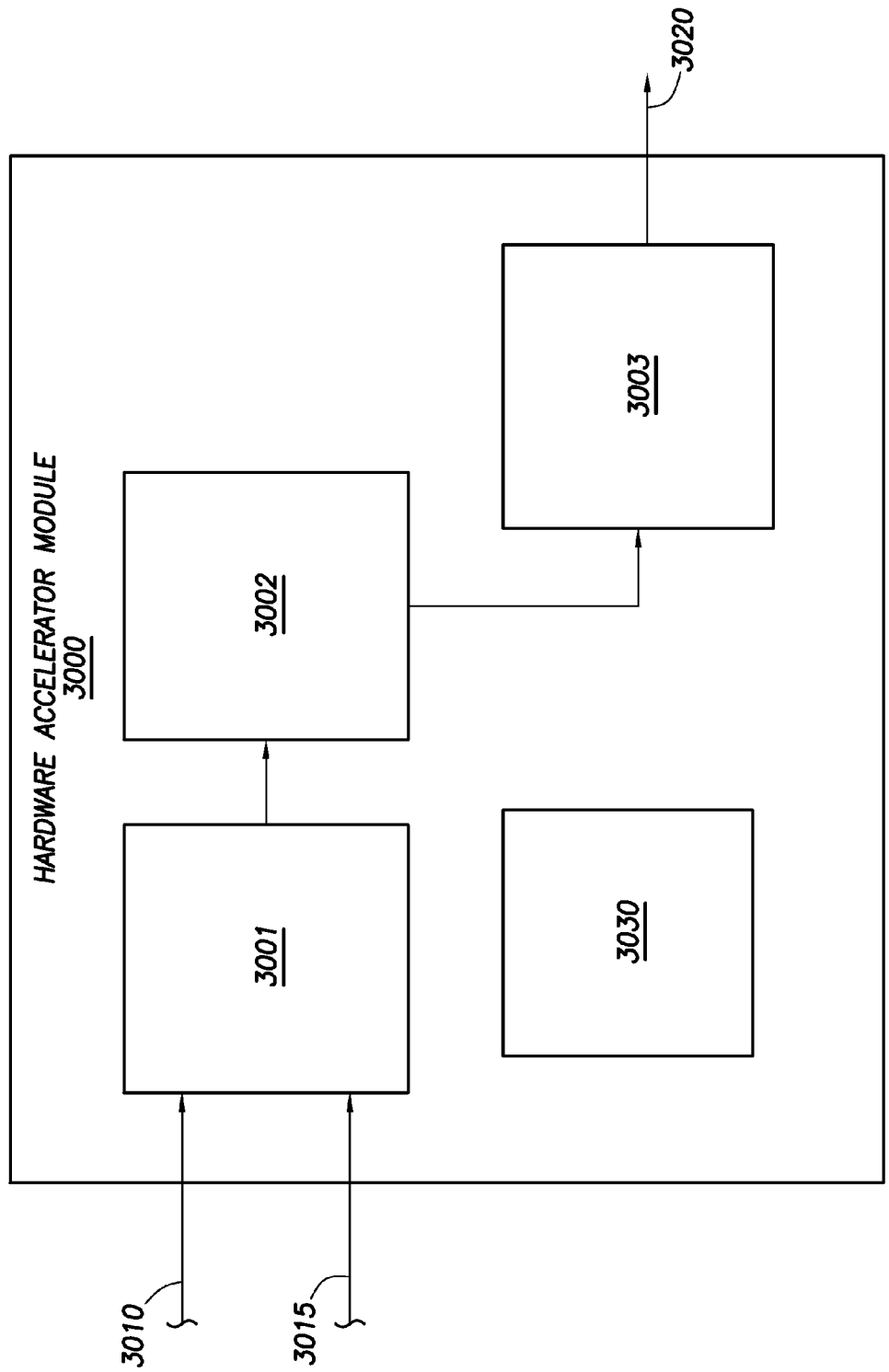
FIG. 30 provides a block diagram of a hardware accelerator module, according to one aspect.

FIG. 30 provides for a block diagram of a HWA module, according to one aspect of the invention. As shown, input block 3001 is coupled to processing block 3002 which is coupled to output block 3003. Input block 3001 receives input signal 3001 and/or instructions 3015. HWA module 300 may, for example, receive a transbody conductive communication signal from the transbody conductive communication module; and/or, receive physiological data signals from one or more physiological sensing modules.

The HWA module may receive an analog signal and include an A/D converter to convert the signal to a digital signal, or may receive a digital input signal (e.g., from an A/D converter or microprocessor). For example, the HWA module may be electrically coupled to an A/D converter and a microprocessor, having a state machine collecting data directly from the A/D converter. In another example, the hardware accelerator may be only connected to the microprocessor processing data as directed by the microprocessor.

Instructions 3015 may be, for example, received from an internal memory, external memory, or by a microprocessor. In one aspect, the HWA module shares memory with the microprocessor (e.g., via dual port memory or via a mux). In another aspect, the HWA module exchanges data via a DMA port.

The HWA processing block 3002 processes input signal 3010 according to received instructions 3015. Functions such as a DCO (digital controlled oscillator), DDC (digital down converter), FIR filter, CIC decimation may be implemented by such a hardware accelerator. These functions are optimal for IEM-related signal processing, and are also applicable to general purpose data acquisition, impedance measurement, ECG signal processing (Hamilton and Tomkins), accelerometer, etc. The resulting output signal 3020 that is generated by HWA processing block 3002 may be transmitted as needed by a HWA output block 3003.

The HWA module 3000 may further comprise an HWA power block 3030 to enable/disable power to HWA module 3000. For example, HWA module 3000 may be configured to be powered off and on, or configured to be disabled by gating the clock which drives it, etc. The transistor count required to implement it is relatively small (roughly in the 10k to 100k gate range) with most of the static power drawn by the associated memory/buffers. The hardware accelerator is thus capable of low power consumption.

Also shown in FIG. 8 is flash memory 890 electrically coupled to high power processor 880. In one aspect, flash memory 890 may be electrically coupled to low power processor 870, which may provide for better power efficiency.

Wireless communication element 895 is shown electrically coupled to high power processor 880 and may include, for example, a BLUETOOTH™ wireless communication transceiver. In one aspect, wireless communication element 895 is electrically coupled to high power processor 880. In another aspect, wireless communication element 895 is electrically coupled to high power processor 880 and low power processor 870. Furthermore, wireless communication element 895 may be implemented to have its own power supply so that it may be turned on and off independently from other components of the receiver—e.g., by a microprocessor.

Figure 9:
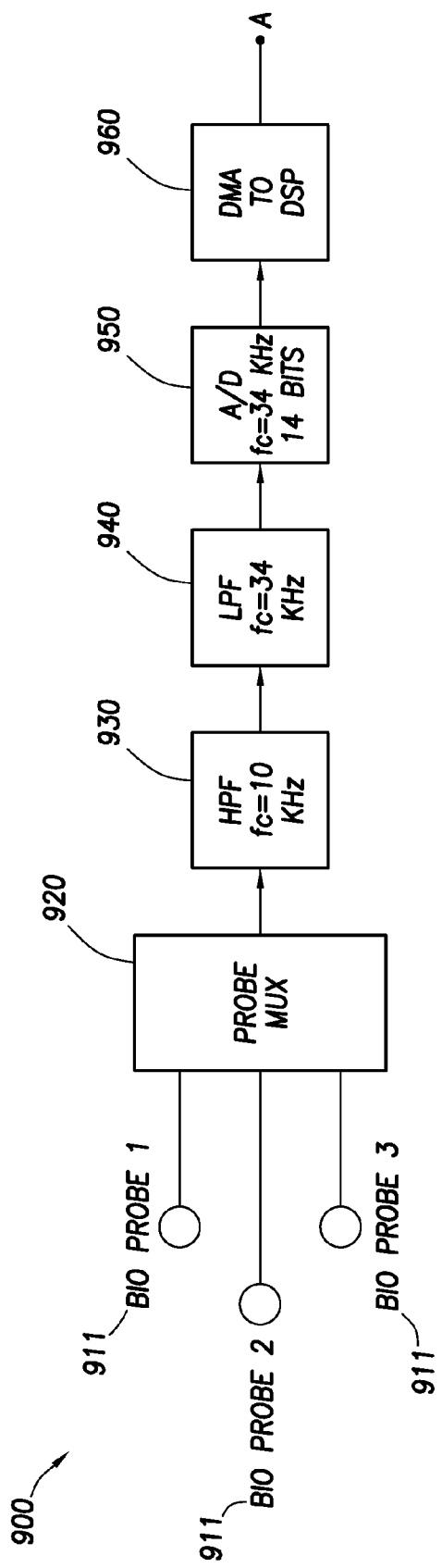
FIG. 9 provides a block diagram of a high frequency signal chain in a receiver, according to one aspect.

FIG. 9 provides a view of a block diagram of hardware in a receiver according to an aspect of the invention related to the high frequency signal chain. In FIG. 9, receiver 900 includes receiver probes (for example in the form of electrodes 911, 912 and 913) electrically coupled to multiplexer 920. Also shown are high pass filter 930 and low pass filter 940 to provide for a band pass filter which eliminates any out-of-band frequencies. In the aspect shown, a band pass of 10 KHz to 34 KHz is provided to pass carrier signals falling within the frequency band. Example carrier frequencies may include, but are not limited to, 12.5 KHz and 20 KHz. One or more carriers may be present. In addition, receiver 900 includes analog to digital converter 950—for example, sampling at 500 KHz. The digital signal can thereafter be processed by the DSP. Shown in this aspect is DMA to DSP unit 960 which sends the digital signal to dedicated memory for the DSP. The direct memory access provides the benefit of allowing the rest of the DSP to remain in a low power mode.

Example Configurations for Various States

Figure 29:
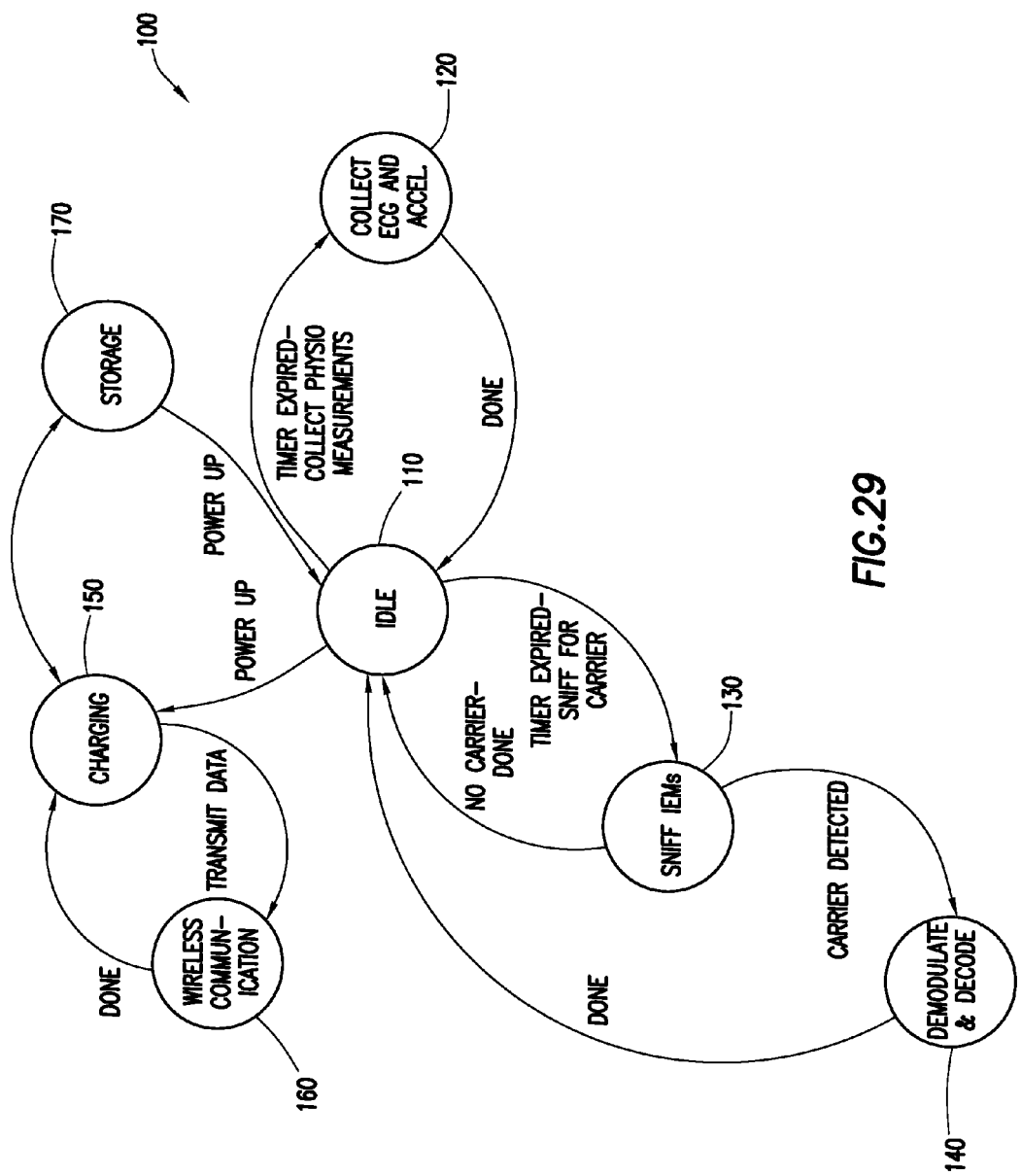
FIG. 29 shows state flow diagram for the power management module and operation of the receiver.

As stated earlier, for each receiver state, the high power functional block may be cycled between active and inactive states accordingly. Also, for each receiver state, various receiver elements (such as circuit blocks, power domains within processor, etc.) of a receiver may be configured to independently cycle from on and off by the power supply module. Therefore, the receiver may have different configurations for each state to achieve power efficiency. For instance, FIG. 29 shows the receiver to have idle and active states—e.g., idle state 110, sniff state 130, demodulate and decode state 140, collect ECG and accelerometer state 120, and transmission state 160). It should be noted that as stated earlier, the beacon signal module may implement various types of sniff signals to achieve low power efficiency, thus the sniff state has been grouped as an inactive state for the following example.

With the states shown in FIG. 29 in mind, the following paragraphs provide example configurations of receiver components shown in FIG. 8 during various states of the receiver, according to one aspect of the invention. It should be understood that alternative configurations may be implemented depending on the desired application.

In the state 110 the receiver draws minimal current. Receiver 800 is configured such that low power processor 870 is in an inactive state (such as idle state) and high power processor 880 is in an inactive state (such as idle state), and circuit blocks related to peripheral circuitry and their power supplies required during various active states remain off (for example, wireless communication module 895 and the analog front end). For example, the low power processor may have a 32 KHz oscillator active and may consume a few μA current or less, including 0.5 μA or less. In the idle state, the low power processor 870 may, for example, wait for a signal to transfer to an active state. The signal might be external such as an interrupt or internally generated by one of the device's peripherals, such as a timer. During the high power processor's idle state, the high power processor may, for example, be running off a 32 KHz watch crystal. The high power processor may, for example, wait for a signal to transfer to active state.

When the receiver is in the sniff state, low power processor 870 is in an idle state and high power processor 880 is in an idle state. In addition, the circuit blocks relating to the analog front end including A/D converter that is needed for the sniff function are on (in other words, the high frequency signal chain). As stated earlier, the beacon signal module may implement various types of sniff signals to achieve low power efficiency.

Upon detection of a transmitted signal, a higher power demodulate and decode state may be entered. When the receiver is in the demodulate and decode state, low power processor 870 is in an active state and high power processor 880 is in an active state. High power processor 880 may, for example, be running from a 12 MHz or near crystal oscillator with a PLL-based clock multiplier giving the device a 108 MHz clock speed. The low power processor 870 may, for example, run off an internal R-C oscillator in the range of 1 MHz to 20 MHz and consume power in the range of 250 to 300 uA per MHz clock speed during active states. The active state allows for processing and any transmissions that may follow. Required transmissions may trigger the wireless communication module to cycle from off to on.

When the receiver is in collect ECG and accelerometer state, the circuit blocks relating to the accelerometer and/or ECG signal conditioning chain are on. The high power processor 880 is in an in idle state during collection, and in an active state (for example, running from a 12 MHz or near crystal oscillator with a PLL-based clock multiplier giving the device a 108 MHz clock speed) during processing and transmission. The low power processor 870 is in an active state during this state and may run off an internal R-C oscillator in the range of 1 MHz to 20 MHz and consume power in the range of 250 to 300 uA per MHz clock speed.

Additional States for the Receiver

In addition to the states of operation where the receiver cycles between idle and active states, the receiver may include other states of operation. Receivers may include a storage state, for example, exhibiting a very low current draw of 10 μA or less, such as 1 μA or less and including 0.1 μA or less. In the storage state the receiver may be configured, for example, so that the low power processor is in an idle state, the high power processor is off, and other receiver elements such as circuit blocks relating to peripheral circuitry needed during active states is off. FIG. 29 illustrates a storage state 170 for a receiver. The receiver may be transitioned from a storage state to a non-storage state according to a variety of inputs, such as a predetermined schedule or an applied stimulus, e.g., in response to a manual manipulation of the receiver (for example by pressing an "on" button or removing a tab from the receiver) or in response to an "on" signal transmitted to the receiver. As shown in FIG. 1, the receiver may transition from storage state 170 into an idle state 110.

Receivers may also be configured to include a charging state, as shown in FIG. 29 as charging state 150. When the receiver is in the charging state, only the low power processor is on, for example in an idle state. The circuit blocks relating to the power supply of the high power processor and all peripherals are turned off.

Receivers may also be configured to include a transmission state 160, where data may be transmitted to and/or from the receiver and another extra-corporeal device, for example by using a wireless communication protocol. The high power processor is in an active state, the low power processor is in an active state, and other receiver elements such as circuit blocks related to the wireless communication module are on.

Receivers may also be configured to include a "diagnostics" state. In a diagnostics state, the receiver may test the operation of one or more functions of the receiver, e.g., signal receiving, physiological data obtainment and/or processing, etc., to determine whether the functions are being performed correctly. The receiver may further be configured to report to a user, e.g., via a signal (which may be audible, visual, relayed to a third device, etc.) the results of the test. For example, the receiver may be configured to report to a user that all functions are operating normally, or that there is a problem with one or more functions. In some aspects, the receiver transitions into and out of a diagnostics state according to different inputs, such as a predetermined schedule (for example as provided by receiver programming) or applied stimulus, such as described above.

Communication Via Serial Peripheral Interface Bus

The low power processor (e.g., MSP shown in FIG. 8) and high power processor (e.g., DSP shown in FIG. 8) may communicate with each other using any convenient communication protocol. In some instances, these two elements, when present, communicate with each via a serial peripheral interface bus (hereinafter "SPI bus"). The following description describes the signaling and messaging scheme implemented to allow the high power processor and low power processor to communicate and send messages back and forth along the SPI bus. For the following description of the communication between the processors, "LPP" and "HPP" are used in place of "low power processor" and "high power processor", respectively, to stay consistent with FIG. 8. The discussion, however, may apply to other processors than those shown in FIG. 8.

The interface is configured so the LPP is the master and the HPP is the slave, and the link is driven only by the LPP side. The HPP can only respond to the LPP via SPI. Furthermore, SPI requires that the HPP respond immediately to the LPP. If the LPP sends data and the HPP is not waiting for the data, then the data are lost. The signaling and messaging configuration for the interface is described below, according to one aspect of the invention, in order to overcome these limitations.

Signaling

To overcome the limits described above, three "out of band" signals are implemented in the signaling protocol. The LPP has an "Attention" signal that it can assert and de-assert, and the HPP has an "Attention" and a "Grant" signal.

For the LPP to send data (e.g., LPP-initiated messages) to the HPP, the LPP asserts its LPP Attention signal. It then waits until the HPP responds by asserting the HPP Grant signal. This ensures that both sides are ready for the SPI transaction and no data are lost. At this point, the HPP is able to receive messages from the LPP. If currently unable to receive LPP-initiated messages from the LPP, the HPP is then enabled to receive LPP-initiated messages. The HPP remains "on the line" until the LPP de-asserts its LPP Attention signal. The HPP responds to this de-assert by de-asserting its HPP Grant signal. At this point, the HPP is unable to receive messages from the LPP. Since able to receive LPP-initiated messages from the LPP, the HPP is then disabled from receiving LPP-initiated messages). In this case, the system responds to both the change in level of the signals and the levels themselves. In other words, the system sees the signal asserted as a request for action and the system looks at the level of that signal as an indicator of continuing action. Because the HPP does not need to do anything until the LPP asserts its LPP Attention signal, the HPP may enter into a low power idle state. In such case, the LPP Attention signal not only requests the SPI link but also wakes up the HPP.

For the HPP to send data (e.g., HPP-initiated messages) to the LPP, the HPP asserts its HPP Attention signal. The assert notifies the LPP that the HPP has data. The assert of the HPP Attention signal is what alerts the LPP, not the de-assert of the HPP Attention signal. The HPP need only de-assert this signal before it can assert it again. Once the LPP sees the HPP Attention signal asserted, it will eventually respond by following 1) above. There is no requirement that the LPP respond immediately. In this case, it is only the assertion of the signal that matters. The system never looks at the ongoing level of that signal.

Messaging:

Because of the master/slave designation of the SPI bus, the HPP can only respond to a LPP message. It cannot ask a question of the LPP.

In order to enable data flow in both directions, the above signaling is implemented in combination with two types of messaging, as described below.

For LPP-initiated messages to the HPP, case 1) above may be employed to send messages to the HPP. This class of messages never requires a response message from the HPP. One example message may be the command, "Process this ECG". A message tells the HPP to expect ECG data and then the LPP sends a series of messages containing the ECG data to the HPP. Another example may be when the LPP sends a command to the HPP telling it to go sniff for transmitted IEM signals.

For HPP-initiated messaging, the messages must still originate at the LPP. To accomplish this direction of communication, case 2) above is used to tell the LPP to query the HPP for a message. Before the HPP asserts the HPP attention signal, it prepares the query information (i.e., the HPP-initiated message) so that it can immediately respond to the LPP. The LPP sends a series of messages to get the query from the HPP. The LPP asks for the query length, and does so by sending a "query length" message to the HPP. The LPP then uses that length to request the HPP-initiated message. Because the LPP asks for the query length, the LPP knows exactly how much data to pull from the HPP. The LPP answers the HPP's "question" by sending a query response message to the HPP. With the HPP implemented to have only one outstanding query at a time, it knows to expect this response.

It should also be pointed out that for the above sequence, the LPP always knows exactly how much data to pull from the HPP because it "clocks" the SPI link. Furthermore, in this aspect, because the LPP always asks the questions and the HPP is always ready to respond to any question from the LPP, the HPP is not guaranteed to always get the "query length" message from the LPP when it wants to send a query.

In one aspect, error detection and correction may be implemented, e.g., by using a Fletcher checksum algorithm. Because a retry is executed upon error detection, for any messages that require an action to be taken (such as pill sniff, etc.), that action is not taken until the entire case 1) above is complete. This is important because the LPP may detect an error while the HPP saw correct data. It is the completion of case 1) above that is the final acknowledgement of complete and correct data transmission.

Global Positioning System (GPS) Module

Receivers of the invention may include a Global Positioning System (GPS) module. GPS modules as used herein are modules that receive signals from the Global Positioning System of satellites and determine geographical location. Any convenient GPS module may be employed.

Receiver Configurations

Body-associate medical devices of interest include both external and implantable devices. In external aspects, the receiver is ex vivo, by which is meant that the device is present outside of the body during use. Where the receivers are external, they may be configured in any convenient manner, where in certain aspects they are configured to be associated with a desirable skin location. As such, in certain aspects the external receivers are configured to be contacted with a topical skin location of a subject. Configurations of interest include, but are not limited to: patches, wrist bands, jewelry (such as watches, earrings and bracelets), clothing, accessories, e.g., belts and shoes, eyeglasses, etc. In some instances, the receivers are configured to adhere to a skin location, e.g., by use of suitable adhesive, such as described below. In some instances, the receivers are configured to touch a skin location but not adhere thereto, for example where the device is configured as a wrist band, an item of jewelry (such as a watch, an earring and a bracelet), an article of clothing, an accessory, such as a belt and a shoe, and a pair of eyeglasses. In yet other instances, the receivers may be configured to be maintained within some defined distance of a skin surface, such as within 1 cm, including within 0.5 cm.

In certain aspects, the receiver is an implantable component. By implantable is meant that the receiver is designed, i.e., configured, for implantation into a subject, e.g., on a semi-permanent or permanent basis. In these aspects, the receiver is in vivo during use. By implantable is meant that the receivers are configured to maintain functionality when present in a physiological environment, including a high salt, high humidity environment found inside of a body, for two or more days, such as about one week or longer, about four weeks or longer, about six months or longer, about one year or longer, e.g., about five years or longer. In certain aspects, the implantable receivers are configured to maintain functionality when implanted at a physiological site for a period ranging from about one to about eighty years or longer, such as from about five to about seventy years or longer, and including for a period ranging from about ten to about fifty years or longer. For implantable aspects, the receiver may have any convenient shape, including but not limited to: capsule-shaped, disc-shaped, etc. The receiver may be configured to be placed in a number of different locations, e.g., the abdomen, small of the back, shoulder (e.g., where implantable pulse generators are placed) etc. In certain implantable aspects, the receiver is a standalone device, in that it is not physically connected to any other type of implantable device. In yet other aspects, the receiver may be physically coupled to a second implantable device, e.g., a device which serves as a platform for one or more physiological sensors, where the device may be a lead, such as a cardiovascular lead, where in certain of these aspects the cardiovascular lead includes one or more distinct physiological sensors, e.g., where the lead is a multi-sensor lead (MSL). Implantable devices of interest further include, but are not limited to: implantable pulse generators (e.g., ICDs), neurostimulator devices, implantable loop recorders, etc.

Receivers may include a signal receiver element which serves to receive the conductively transmitted signal, such as a signal emitted by an identifier of an ingestible event marker. The signal receiver may include a variety of different types of signal receiver elements, where the nature of the receiver element necessarily varies depending on the nature of the signal produced by the signal generation element. In certain aspects, the signal receiver element may include one or more electrodes for detecting signal emitted by the signal generation element, such as two or more electrodes, three or more electrodes, etc. In certain aspects, the receiver device will be provided with two or three electrodes that are dispersed at some distance from each other. This distance allows the electrodes to detect a differential voltage. The distance may vary, and in certain aspects ranges from 0.1 cm to 1.0 m, such as 0.1 to 5 cm, such as 0.5 to 2.5 cm, where the distance 1 cm in some instances.

Figure 10:
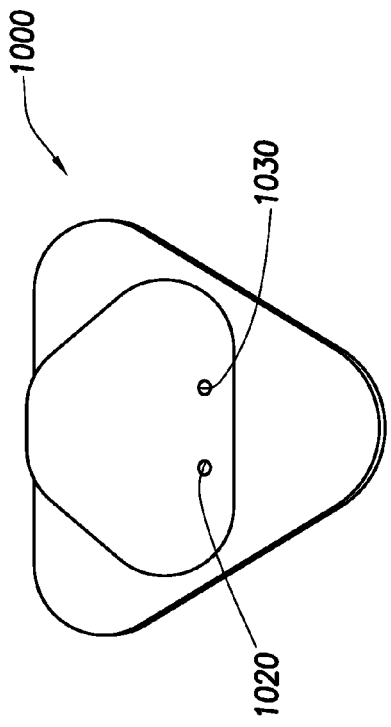
FIG. 10 is a three-dimensional view of an external signal receiver, according to one aspect.

An example of an external signal receiver aspect of a receiver of interest is shown in FIG. 10. FIG. 10 shows receiver 1000 that is configured to be placed on an external topical location of a subject, such as a chest area. The receiver includes an upper housing plate 1010 (such as may be fabricated from a suitable polymeric material), and includes a manually depressible operation button 1020 and a status identifier LED 1030, which may be used to relay to an observer that the receiver is operating. Manually depressible operation button 1020 can be manually manipulated to transition the receiver from a storage mode to a non-storage mode. When the receiver is in the storage mode, a micro-controller of the receiver may remain in a low duty cycle active state at all times to process input from the on/off button, and the digital signal processor (DSP) of the receiver powered off. When the on/off button is depressed to turn on the receiver, the micro-controller de-bounces the input and powers the DSP into its idle state. While in storage mode, the device may draw less than 10 µA, including 5 µA of current or less, such as 1 µA or less and including 0.1 µA or less. This configuration enables the device to remain at greater than 90% useful battery life if stored for one month (assuming the presence of a 250 mAH battery). Such a button may also be employed for other functions. For example, such a button may be employed to instruct the receiver to obtain certain types of data. In addition or alternatively, such a button may be employed to manually instruct the receiver to transfer data to another device.

Figure 11:
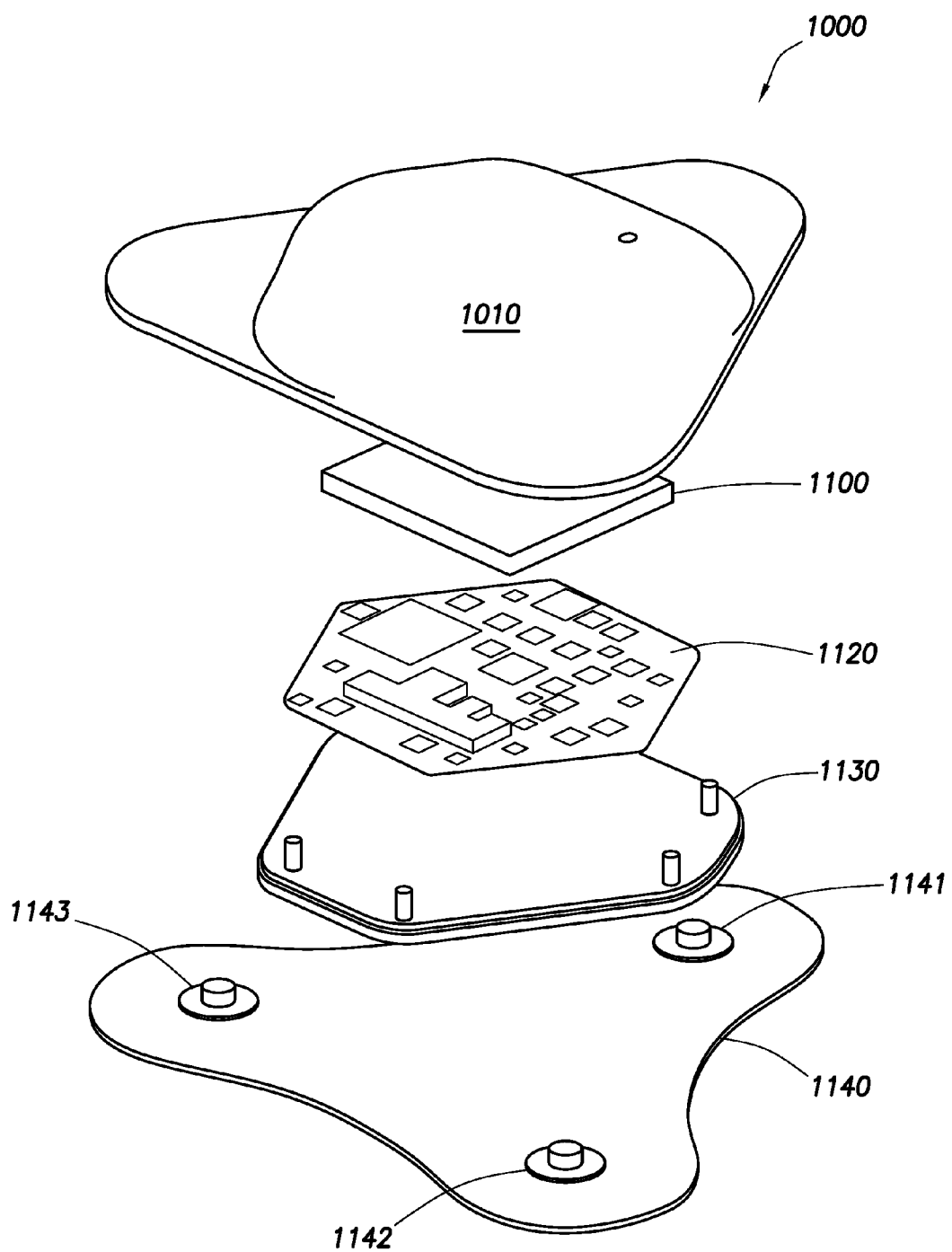
FIG. 11 provides an exploded view of the signal receiver shown in FIG. 10, according to one aspect.

FIG. 11 provides an exploded view of the receiver shown in FIG. 10. As shown in FIG. 11, receiver 1000 includes upper housing plate 1010, rechargeable battery 1100, integrated circuit component 1120, and bottom housing plate 1130. Bottom housing plate 1130 snap fits into top housing plate 1010 to seal the battery and integrated circuit components, 1100 and 1120, in a fluid tight housing. While a snap-fit interaction is illustrated, any convenient mating scheme may be employed, such that the top and bottom housing plates may interact via inter-locking grooves, may be held together via a suitable adhesive, may be welded together, etc. In some instances, the electrical components may be molded into the top and/or bottom housing plates. Also shown is adhesive patch 1140 which snaps into top housing plate 1010 and includes conductive studs 1141 to 1143, which studs serve as electrode contacts with the body during receiver use. In the receiver, studs 1141 to 1143 are in electrical contact with integrated circuit component 1120, e.g. via wires or other conductive members associated with the upper housing 1010. In one instance, upper housing plate 1010 includes conductive members configured to receive studs 1141 to 1143 coupled to wires (not shown) which in turn provide electrical connection to the integrated circuit component 1120.

Figure 12:
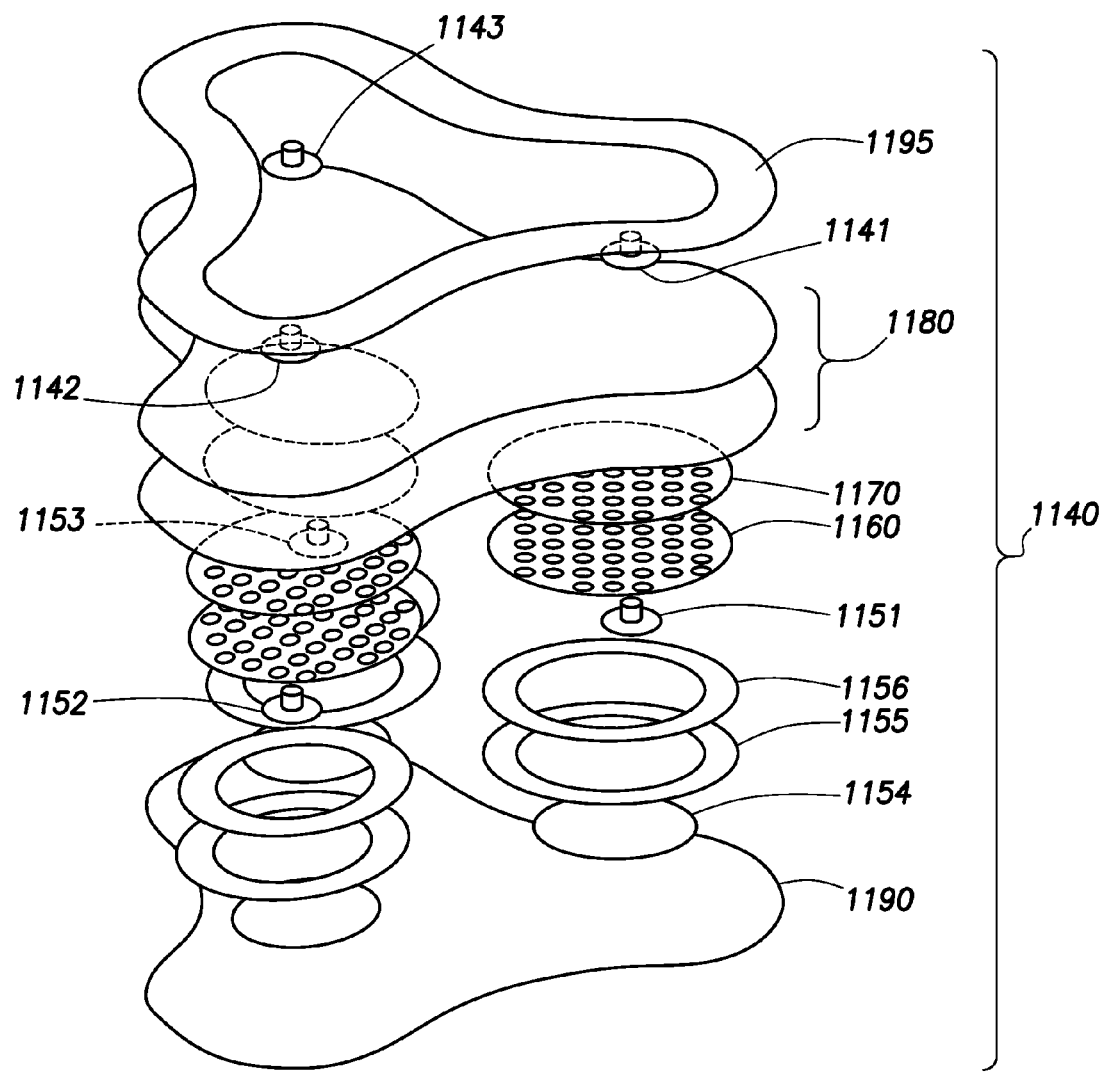
FIG. 12 provides an exploded view of the adhesive patch component of the signal receiver shown in FIGS. 10 and 11, according to one aspect.

FIG. 12 provides an exploded view of adhesive patch 1140. Adhesive patch 1140 includes upper studs 1141, 1142 and 1143, as described above. These studs are in electrical contact with skin contact studs 1151, 1152 and 1153. On the skin side surface of skin contact studs 1151, 1152 and 1153 is a conductive hydrogel layer 1154. Around each stud 1151, 1152 and 1153 are non-conductive hydrogel 1155 and pressure sensitive adhesive 1156 components. In this portion, any convenient physiologically acceptable adhesive may be employed. In some instances, adhesive that chance their adhesive properties in response to an applied stimulus are employed. For example, adhesives that become less adhesive upon application of light, e.g., UV light, or a chemical, may be employed, so that the adhesive remains strong while it is desired for the receiver to remain associated with the body but is readily weakened to facilitate removal of the receiver from the body when desired. On the non-skin side of each skin contact stud is a layer of dry electrode material, such as Ag/AgCl. On the upper surface of this layer of dry electrode material is a porous layer, such as a carbon vinyl layer. Also shown are upper backing layers 1180. Though not shown, upper studs 1141 to 1143 are in electrical contact through the backing layers 1180 (for example urethane and polyethylene) with the dry electrode and skin contact studs which are positioned beneath each upper stud. As illustrated, the studs are off center with respect to their dry electrode layer in the direction of the outer edge of the patch in a manner sufficient to increase dipole size between any two given studs. In addition, where desired a conductivity gradient may be associated with each stud, e.g., by altering the pattern of the porous layer 1170 and/or modifying the composition of the dry electrode layer. Of interest in such aspects is where a conductivity gradient increases in conductivity in the direction of the outer edge of the patch.

FIGS. 13A to 13E provide various views of an alternative external patch configuration 1300 which includes two electrodes 1310 and 1320 in a flexible structure having an adhesive bandage configuration. Patch 1300 includes upper flexible outer support 1330 and bottom flexible support 1350 which fit together as shown in FIG. 13E to enclose an integrated circuit/battery component 1360 and electrodes 1310 and 1320. As shown in FIG. 13D, the bottom surfaces of electrodes 1310 and 1320 are exposed. As shown in FIG. 13E, electrodes 1310 and 1320 include lead elements 1375 and 1370 which provide for electrical contact between the electrodes and the integrated circuit/battery component 1360. Any convenient adhesive component may be employed, such as those described above.

FIGS. 14A to 14B provide block diagrams of example hardware configurations that may be present in a receiver as shown in FIGS. 13A to 13E. However, it should be understood that the example hardware configurations are not limited to the aspects shown in FIGS. 13A to 13E.

FIG. 14A provides a block diagram of an example hardware configuration that may be included in a receiver such as receiver 1300, according to one aspect of the invention. As shown, hardware system 1400 includes first and second electrodes 1310 and 1320 electrically coupled to analog ASIC 1410. ASIC 1410 may include, for example, the analog front end of hardware system 1400 (e.g., the high frequency signal chain, low frequency signal chain, etc.). Just as the analog front end may be implemented in an ASIC, customized logic may replace the DSP. Digital ASIC 1420 is shown electrically coupled to analog ASIC 1410 and performs the digital signal conditioning and processing. Accelerometer 1430, such as a three-axis accelerometer, is shown electrically coupled to digital ASIC 1420. In one aspect, accelerometer 1430 is electrically coupled to analog ASIC 1410. It is also understood that a digital accelerometer may be implemented. Microprocessor 1440 is shown electrically coupled to digital ASIC 1410 and flash memory 1450. Furthermore, microprocessor 1440 is shown electrically coupled to radio 1460, such as a wireless transceiver.

FIG. 14B provides a block diagram of another example hardware configuration that may be included in a receiver such as receiver 1300, according to one aspect of the invention. Within hardware system 1490, electrodes 1310 and 1320 are shown electrically coupled to optional low noise amplifier (LNA) 1461. Analog ASIC 1462 is shown electrically coupled to LNA 1461 and may include, for example, the analog front end of hardware system 1490. Digital ASIC 1463 is shown electrically coupled to analog ASIC 1462 and performs the digital signal conditioning and processing. In this aspect, digital ASIC 1463 also includes microprocessing unit 1464, which may be any convenient microprocessing unit such as the CORTEX-M3™ microprocessing unit by ARM. Accelerometer 1430 is electrically coupled to analog ASIC 1462, but as noted earlier, may be implemented to be electrically coupled to the digital ASIC 1463 as well as a digital accelerometer. Electrically coupled to digital ASIC 1463 is radio 1460.

Figure 14C:
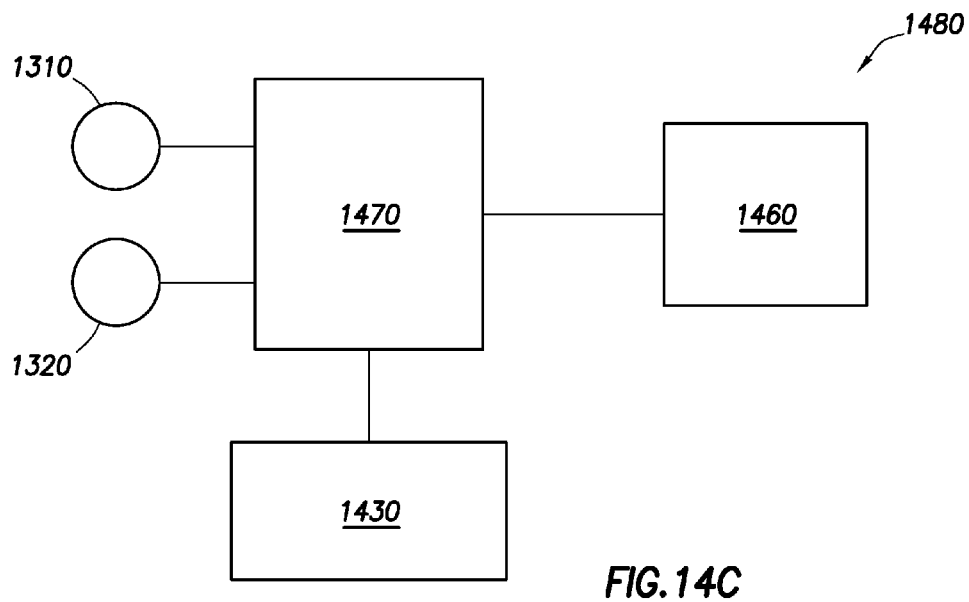

FIG. 14C provides a block diagram of yet another example hardware configuration that may be included in a receiver such as receiver 1300, according to one aspect of the invention. Within hardware system 1480, a single system on chip (SOC) 1470 replaces the two ASICs in FIGS. 14A and 14B. For instance, SOC 1470 would replace ASICs 1410 and 1420 shown in FIG. 14A, or ASICs 1462 and 1463 shown in FIG. 14B (in which case optional LNA 1460 is not shown). In this case, radio 1460 is electrically coupled to SOC 1470.

Figure 14D:
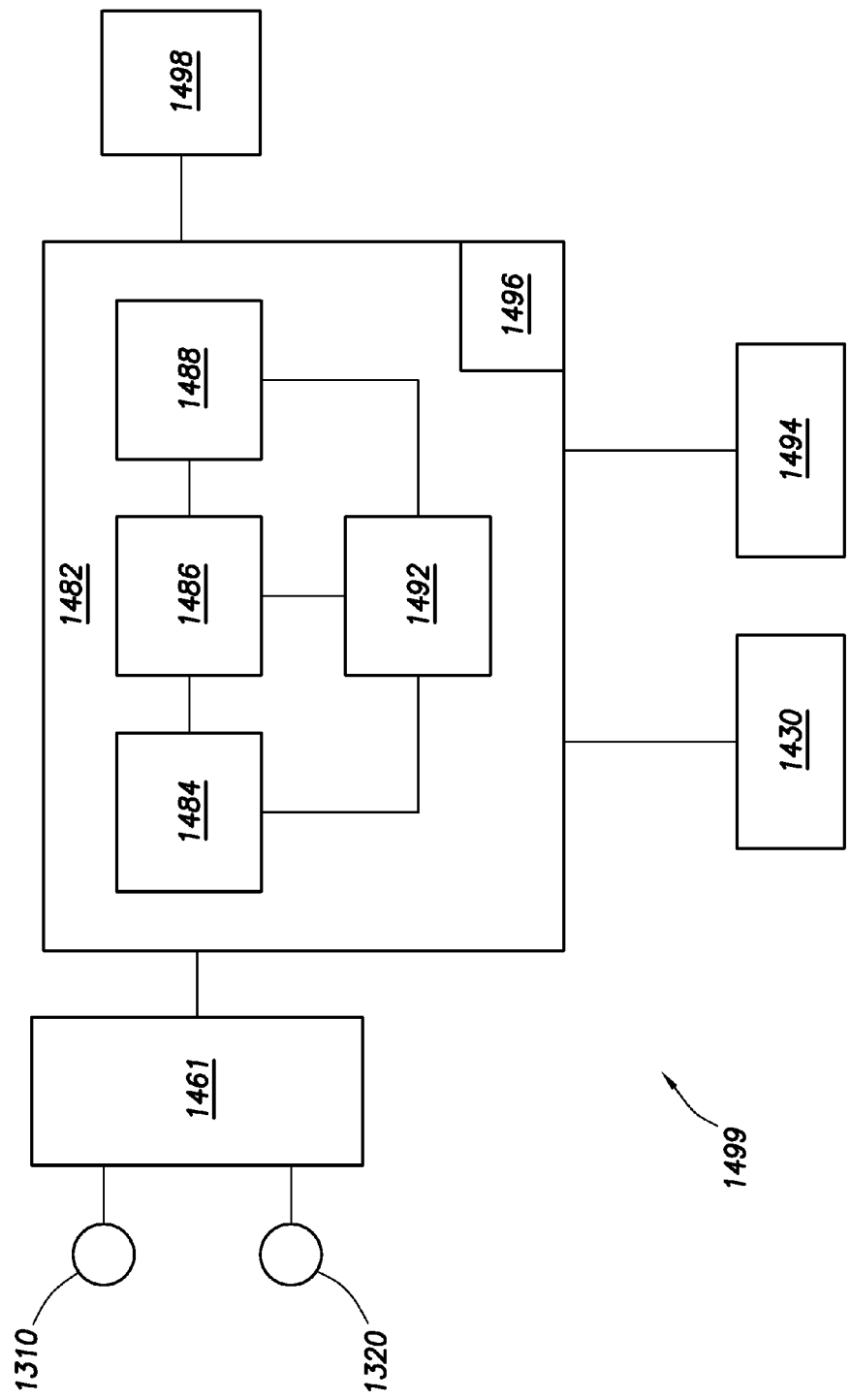

FIG. 14D provides a block diagram of yet another example hardware configuration that may be included in a receiver, such as receiver 1300, according to one aspect of the invention. Within hardware system 1499, optional LNA 1461 is electrically coupled to electrodes 1310 and 1320. SOC 1482 is shown electrically coupled to an optional LNA 1461, accelerometer 1430, temperature sensor 1494 and radio 1498 (e.g., a wireless communication module including a transceiver). SOC 1492 includes processor 1492, electrode input 1484, analog front end 1486 (e.g., transbody conductive communication module and physiological sensing modules), and software defined radio 1488. Furthermore, a temperature sensor 1496 may also be included in single ASIC 1470 and/or radio 1498 (sensor not shown).

Where desired, one or more components of the receiver may be covered with a conformal, void-free sealing layer, e.g., as described in U.S. application Ser. No. 12/296,654, the disclosure of which application is herein incorporated by reference. The conformal, void-free sealing layer may be characterized as a "thin-film" coating in that its thickness is such that it does not substantially increase the total volume of the structure with which it is associated, where any increase in volume of the device that can be attributed to the layer is about 10% or less, such as about 5% or less, including about 1% or less by volume. According to aspects of the invention, a conformal, void-free sealing layer has a thickness in a range from 0.1 to 10.0 µm, such as in a range from 0.3 to 3.0 µm, and including in a range from 1.0 to 2.0 µm thick. According to aspects of the present invention, a conformal, void-free sealing layer may be applied using a planar processing protocol, e.g., plasma-enhanced-chemical-vapor deposition, physical-vapor deposition, sputtering, evaporation, cathodic-arc deposition (see e.g., U.S. application Ser. No. 12/305,894, the disclosure of which application is herein incorporated by reference), low-pressure chemical-vapor deposition, and other such processes. When present, conformal, void-free sealing layers may comprise a variety of different materials. In one aspect, the layer comprises silicon carbide to create a highly corrosion resistant seal. Alternatively, the layer may include silicon dioxide, carbon oxides, carbon oxynitrides, metals, e.g., noble metals and alloys thereof, such as platinum, rhodium, iridium, and alloys thereof, metal silicides, nitrides, e.g., silicon nitrides, carbon nitrides, aluminum nitrides, titanium nitride, tungsten carbide or other carbides. The layer may be a single layer or made up of multiple layers of the same material or different materials. When multiple materials are employed, the coefficients of thermal expansion may also be calculated and designed so that they do not adversely affect the receiver component with which they are associated. In some instances, a conformal, void-free sealing layer covers at least a portion of the outer surface, if not the entire outer surface, of the receiver. In such instances, an electrical connection(s) may be present in the sealing layer to provide for electrical communication between components inside of the receiver and the external environment of the receiver.

Active Agent Delivery

Receivers of the invention may include an active agent delivery component. The active agent delivery component, when present, may vary. In some instances, the active agent delivery component may be a distinct component of the receiver, where the component may include a source of an active agent composition. The active agent composition may vary and include one or more active agents in combination with a carrier composition, where the carrier composition may be a liquid or solid composition and may be configured to provide for a controlled release delivery profile, as desired. Active agent delivery components of interest include, but are not limited to: solid delivery formats, such as patch and plaster delivery formats, and fluid introduction formats, such as iontophoretic formats and formats that employ a microneedle component, as described in greater detail below. For implantable receivers, any convenient active agent delivery format may be employed. Examples of active agent delivery formats of interest include, but are not limited to, those described in 11/897,931; the disclosure of which is herein incorporated by reference. Depending on the particular format, the delivery component may include a device component that provides for delivery of an amount of the active agent composition from the source to the patient. The device component may vary widely, where examples of device components include selective membranes, pumps, electric field sources, microneedles, etc. In certain instances, the active agent delivery component may be integrated with another component of the receiver. For example, where receivers include an adhesive component, the adhesive composition of the adhesive component may include one or more active agents, as desired, where the adhesive composition may be formulated to provide for any desired active agent delivery profile. Where active agent delivery is included, the receiver may be configured to deliver the active agent in accordance with a predetermined dosing schedule, in response a received dosing signal, in response to one or more detected physiological parameters (for example where the device is configured as a closed-loop active agent delivery device), etc.

Microneedle

Receivers of the invention may include a microneedle component, which microneedle component may be configured for analyte detection and/or active agent delivery, for example as described in greater detail below. Microneedle components of interest are configured for transfer of biological fluid from a physiological source to another location (for example external site) in a minimally-invasive, painless, and convenient manner. The microneedle components may be configured to permit in vivo sensing or withdrawal of biological fluids from the body, such as from or through the skin, with minimal or no damage, pain, or irritation to the tissue.

Microneedle components may include one or more microneedles (where multiple microneedles may be configured in any convenient format, such as in a three-dimensional array), a substrate to which the one or more microneedles are connected, a fluid chamber and/or a sensor in communication with the one or more microneedles.

The microneedles may be configured to function either as a conduit, a sensing element, or a combination thereof. Conduit microneedles can have a porous or hollow shaft. As used herein, the term "porous" means having pores or voids throughout at least a portion of the microneedle structure, sufficiently large and sufficiently interconnected to permit passage of fluid and/or solid materials through the microneedle. As used herein, the term "hollow" means having one or more substantially annular bores or channels through the interior of the microneedle structure, which have a diameter sufficiently large to permit passage of fluid and/or solid materials through the microneedle. The annular bores may extend throughout all or a portion of the needle in the direction of the tip to the base, extending parallel to the direction of the needle or branching or exiting at a side of the needle, as appropriate. A solid or porous microneedle can be hollow. Where desired, one or more of the microneedles may be coated (if solid, porous, or hollow) and/or at least partially filled (if porous or hollow) with a sensing or diffusion-modifying material.

The microneedles can be constructed from a variety of materials, including metals, ceramics, semiconductors, organics, polymers, and composites. Construction materials of interest include, but are not limited to: pharmaceutical grade stainless steel, gold, titanium, nickel, iron, tin, chromium, copper, palladium, platinum, alloys of these or other metals, silicon, silicon dioxide, and polymers. Biodegradable polymers of interest include, but are not limited to: polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Non-biodegradable polymers of interest include, but are not limited to: polycarbonate, polymethacrylic acid, ethylenevinyl acetate, polytetrafluoroethylene, and polyesters.

The microneedles can be configured with shafts that have a circular cross-section in the perpendicular, or the cross-section can be non-circular. For example, the cross-section of the microneedle can be polygonal (such as star-shaped, square, triangular), oblong, or another shape. The shaft can have one or more bores. The cross-sectional dimensions may vary, and in some instances range between 1 µm and 500 µm, such as between 10 µm and 100 µm. The outer and inner diameters may also vary, with the outer diameter ranging in some instances between 10 µm and 100 µm, and the inner diameter ranging in some instances between 3 µm and 80 µm. The length of the microneedles may also vary, ranging in some instances between 10 µm and 1 mm, such as between 100 µm and 500 µm, and including between 150 µm and 350 µm.

The substrate of the device can be constructed from a variety of materials, including metals, ceramics, semiconductors, organics, polymers, and composites. The substrate includes the base to which the microneedles are attached or integrally formed. Where desired, the substrate of the microneedle component can be integrated with another component of the receiver structure.

A fluid chamber (configured as a fluid collection chamber or an active agent depot) and/or sensor can be attached to the substrate or formed (for example, as part of the substrate) to communicate directly with the base of the microneedles.

The fluid chamber, when present, may be selectively in connection with the microneedle bores or pores, such that a biological fluid can flow from the tissue surrounding the microneedle, through the microneedle, and into the fluid chamber or an active agent composition can flow from the chamber through the microneedles and into the subject. Where desired, the fluid chamber is attached to, or integrated into, the substrate. The fluid chamber can be substantially rigid or readily deformable. The fluid chamber can be formed from one or more polymers, metals, ceramics, semiconductor, or combinations thereof. In one aspect, the fluid chamber contains a porous or absorbent material, such as a sponge, gel, or paper or polymeric strip. The fluid chamber may include a fluid active agent composition, which includes one or more active agents in combination with a carrier formulation. As such, the fluid chamber can initially be empty or can contain a gas or one or more reagents in any form (such as, liquid or solid particles) or active agent(s), etc., as desired.

Where desired, the microneedle component may include one or more sensors. The sensors can be located in the microneedle or body of the device (for example in the fluid chamber). The sensors can be in or attached to one or more microneedles, integrated into the substrate, or within or in communication with the fluid chamber. Sensors of interest include sensors of pressure, temperature, chemicals, pH, and/or electro-magnetic fields. Sensor of interest include those configured to detect the presence of a chemical analyte in a biological fluid sample, where analytes of interest include, but are not limited to: blood sugar (glucose), cholesterol, bilirubin, creatine, various metabolic enzymes, hemoglobin, heparin, hematocrit, vitamin K or other clotting factors, uric acid, carcinoembryonic antigen or other tumor antigens, various reproductive hormones such as those associated with ovulation or pregnancy, drugs of abuse and/or metabolites thereof; blood alcohol concentration, etc. In certain aspects, substances or properties for which the receiver is configured to detect include lactate (important for athletes), oxygen, pH, alcohol, tobacco metabolites, and illegal drugs (important for both medical diagnosis and law enforcement). Sensors, when present, may be in communication with a microneedle sensor function module, which may include software and/or hardware components and present solely in the microneedle component and/or integrated, at least to some extent, into other parts of the receiver.

Systems

In certain aspects, the receivers are part of a body-associated system or network of devices, such as sensors, signal receivers, and optionally other devices, which may be internal and/or external, which provide a variety of different types of information that is ultimately collected and processed by a processor, such as an external processor, which then can provide contextual data about a living subject, such as a patient, as output. For example, the receiver may be a member of an in-body network of devices which can provide an output that includes data about IEM ingestion, one or more physiological sensed parameters, implantable device operation, etc., to an external collector of the data. The external collector, e.g., in the form of a health care network server, etc., of the data then combines this receiver provided data with additional relevant data about the patient, e.g., weight, weather, medical record data, etc., and may process this disparate data to provide highly specific and contextual patient specific data.

Systems of the invention include, in certain aspects, a signal receiver aspect of a receiver and one or more IEMs. IEMs of interest include those described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753 published as WO 2009/042812; the disclosures of which applications are herein incorporated by reference.

In certain aspects the systems include an external device which is distinct from the receiver (which may be implanted or topically applied in certain aspects), where this external device provides a number of functionalities. Such an external device can include the capacity to provide feedback and appropriate clinical regulation to the patient. Such a device can take any of a number of forms. For example, the device can be configured to sit on the bed next to the patient, e.g., a bedside monitor. Other formats include, but are not limited to, PDAs, smart phones, home computers, etc.

Figure 15A:
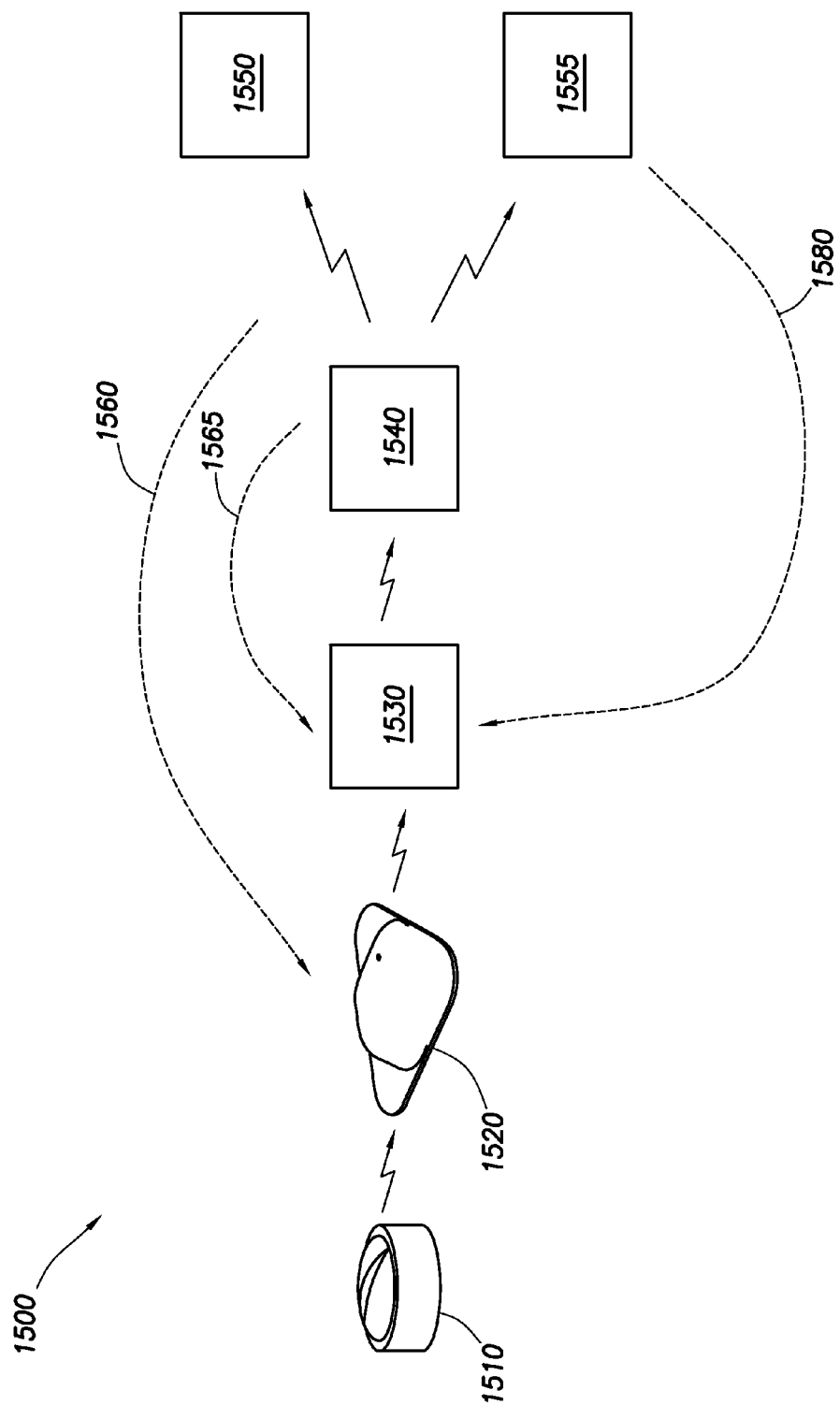
FIG. 15A provides a diagram of how a system that includes a signal receiver and an ingestible event marker may be employed, according to one aspect.

An example of a system of the invention is shown in FIG. 15A. In FIG. 15A, system 1500 includes a pharmaceutical composition 1510 that comprises an IEM. Also present in system 1500 is signal receiver 1520, such as the signal receiver illustrated in FIGS. 10 to 12. Signal receiver 1520 is configured to detect a signal emitted from the identifier of the IEM 1510. Signal receiver 1520 also includes physiologic sensing capability, such as ECG and movement sensing capability. Signal receiver 1520 is configured to transmit data to a patient's an external device or PDA 1530 (such as a smart phone or other wireless communication enabled device), which in turn transmits the data to a server 1540. Server 1540 may be configured as desired, e.g., to provide for patient directed permissions. For example, server 1540 may be configured to allow a family caregiver 1550 to participate in the patient's therapeutic regimen, e.g., via an interface (such as a web interface) that allows the family caregiver 1550 to monitor alerts and trends generated by the server 1540, and provide support back to the patient, as indicated by arrow 1560. The server 1540 may also be configured to provide responses directly to the patient, e.g., in the form of patient alerts, patient incentives, etc., as indicated by arrow 1565 which are relayed to the patient via PDA 1530. Server 1540 may also interact with a health care professional (e.g., RN, physician) 1555, which can use data processing algorithms to obtain measures of patient health and compliance, e.g., wellness index summaries, alerts, cross-patient benchmarks, etc., and provide informed clinical communication and support back to the patient, as indicated by arrow 1580.

Figure 15B:
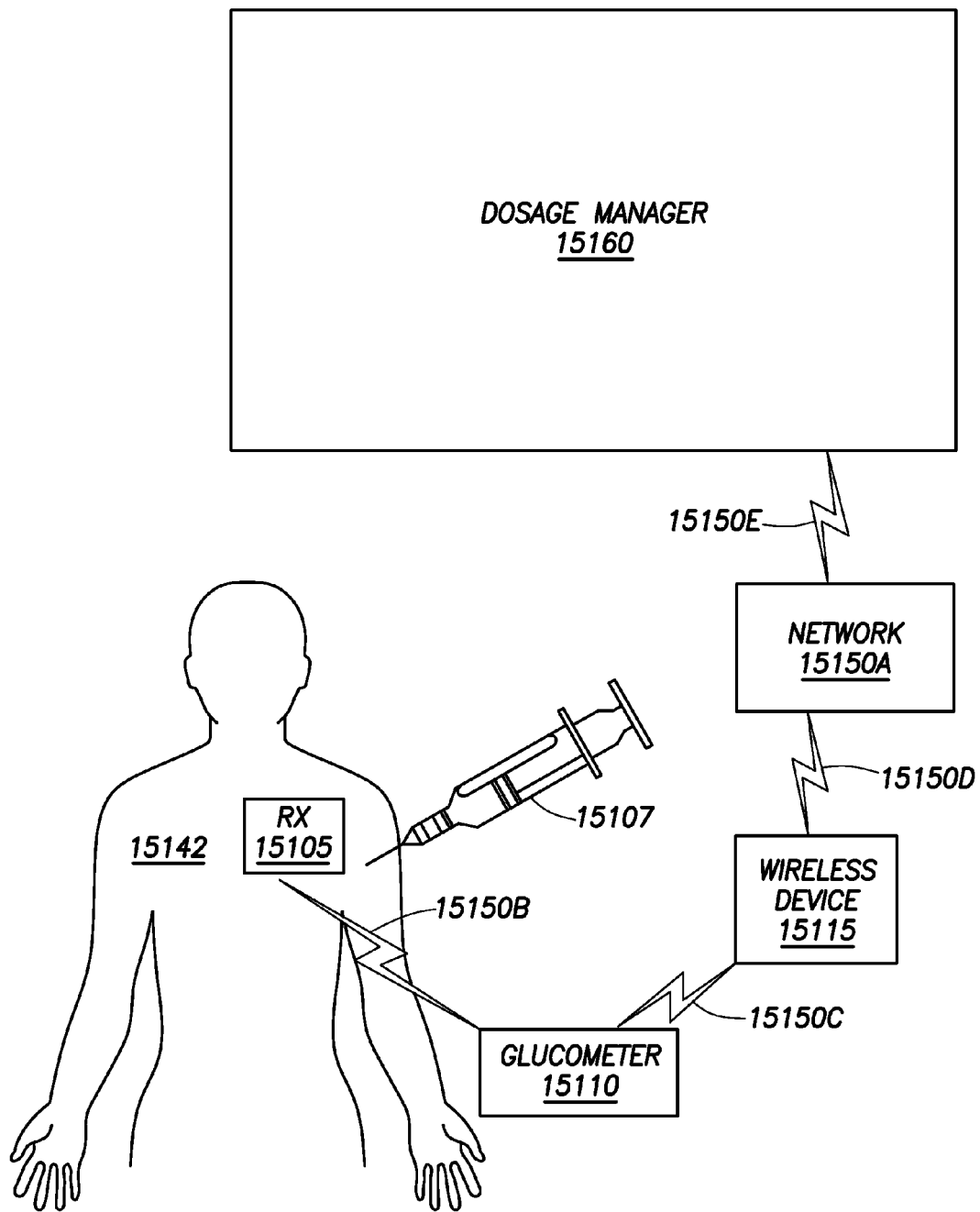
FIG. 15B provides a pharmaceutical delivery system that receives control information from a receiver and control the dosage delivery.

Another example of the system of the present invention is shown in FIG. 15B. FIG. 15B depicts a system that includes a syringe 15107, a receiver 15105, a glucometer 15110, a wireless communication unit 15115, communication links 15150B-E, and a dosage manager 15160. The system generally provides intelligent mechanisms for controlling the delivery of a dosage by the syringe 15107 (e.g., subcutaneous needle insertion or luer connection with an Intra Venous access device). This control may include, for example, detecting that the syringe 15107 is proximate to the patient, measuring the amount of the dose administered by the syringe 15107, communicating the measurement information to other devices, such as the receiver 15105, the glucometer 15110, the wireless devices 15115, and/or the dosage manager 15160, and providing feedback information to one or more of those devices. In some implementations, the feedback information may prevent the administration of the dosage to the patient using, for example, an interlock at the syringe 15107 to prevent giving the dosage. The syringe 15107 may, based on the feedback, output a visual indication (e.g., a light emitting diode (LED)) or an aural signal to indicate that the dosage is not to be administered to the patient. For example, the interlock mechanism, LED, and/or sound at the syringe 15107 may signal that the patient is receiving the wrong type of medication, receiving the dosage at the wrong time, and/or receiving the wrong amount of medication.

In some implementations, the syringe 15107 may be configured in an interlock mode as a default state to prevent the administration of a dosage until the dosage manager 15160 provides feedback information to unlock the syringe 15107 to allow the administration of the agent or medication.

Moreover, the syringe 15107 may, in some embodiments, include a measurement mechanism to provide measurement information representative of the amount of the dosage. When that is the case, the measurement information may be used by the dosage manager 160 along with other patient information, such as blood pressure, glucose level, heart rate, ingestible event marker (IEM) data, etc., to control when, and/or how much of, a dosage is provided to the patient. Furthermore, the syringe 15107 may activate the measurement mechanism (which provides the measured information) when the syringe 15107 is proximate to (e.g., enters or is close to) the patient's body, at which time the measurement information and other information, such as an identifier associated with the syringe 15107, a patient identifier, etc., are carried by a signal to other devices, such as the receiver 15105, the glucometer 15110, and/or the wireless device 15115, for communication to the dosage manager 15160. Moreover, these other devices may monitor the time when the dosage is administered by the syringe 15107. As such, the dosage manager 15160 may receive a precise time when the dosage is administered rather than rely on user-provided dosage administration times. As such, the system may be used to evaluate a specific fluid transfer event between a parenteral fluid delivery device, such as syringe 15107, and a patient In some aspects of systems of the invention, a receiver of the invention that includes a multi-purpose connector is operatively coupled to either a patient or another device via the multi-purpose connector. As reviewed above, other devices that the receiver may be operatively coupled to include, but are not limited to, an external charger device, an external programming device, an external data processing device, etc. In some instances, the system may include the receiver operatively coupled to a patient, either directly or to an external proximal end of a patient-associated device, such as an implanted medical device.

Where the receiver is operatively coupled to an external device, it may be directly connected to the external device or connected to the external device through one or more distinct connector devices, such as cables, cords or analogous structure. An example of an external device is an external programming device. The programming device may be configured to change the settings of the receiver. For example, the programming device may change the operating settings of the receiver, for example the parameters for signal measurement on the patient, frequency of measurement, duration of measurement, electrodes to use for measurement, etc. The programming device may also change the operating mode of the receiver. The programming device may also be able to send data to the receiver, such as medical records or other data about the patient. The programming device may be any device suitable for this purpose. Programming devices of interest include, but are not limited to, a computer with a built-in or peripheral monitor (such as may be found in a bedside monitor or a health information system), a personal digital assistant (PDA), a smart phone, a messaging device, or other handheld device, etc.

Systems of the invention may also include an external data processor configured to receive data from the receiver. The external data processor may receive the electrical signal data directly from the receiver, or via a data relay device (such as a device that receives data from the body-associated signal receiver and then forwards the received data to an extra-corporeal data processor). The external data processor may be configured to receive the data via any convenient wired or wireless protocol, as desired. Some external data processors of interest may receive data from the receiver by connecting to the multi-purpose connector. External data processors of interest are those that can receive the electrical signal data and process the data to produce useful information. The external data processor may also simply store the data for later processing or viewing. The processed data may be output to a user by any convenient medium, such as writing the data on paper, displaying the processed data to a user via a graphical user interface, and the like. The data may be arranged in any useful form, such as a graph, table, or signal. External data processors of the systems of the invention may take a variety of configurations, such as a computer with a built-in or peripheral monitor (for example as embodied in a bedside monitor or a health information system), a personal digital assistant (PDA), a smart phone, a messaging device, etc.

Systems of the invention enable a dynamic feedback and treatment loop of tracking medication timing and levels, measuring the response to therapy, and recommending altered dosing based on the physiology and molecular profiles of individual patients. For example, a symptomatic heart failure patient takes multiple drugs daily, primarily with the goal of reducing the heart's workload and improving patient quality of life. Mainstays of therapy include angiotensin converting enzyme (ACE) inhibitors, β-blockers and diuretics. For pharmaceutical therapy to be effective, it is vital that patients adhere to their prescribed regimen, taking the required dose at the appropriate time. Multiple studies in the clinical literature demonstrate that more than 50% of Class II and III heart failure patients are not receiving guideline-recommended therapy, and, of those who are titrated appropriately, only 40-60% adhere to the regimen. With the subject systems, heart failure patients can be monitored for patient adherence to therapy, and adherence performance can be linked to key physiologic measurements, to facilitate the optimization of therapy by physicians.

In certain aspects, the systems of the invention may be employed to obtain an aggregate of information that includes sensor data and administration data. For example, one can combine the heart rate, the respiration rate, multi-axis acceleration data, something about the fluid status, and something about temperature, and derive indices that will inform about the total activity of the subject, that can be used to generate a physiological index, such as an activity index. For instance, when there is a rise in temperature, heart rate goes up a bit, and respiration speeds up, which may be employed as an indication that the person is being active. By calibrating this, the amount of calories the person is burning at that instant could be determined. In another example, a particular rhythmic set of pulses or multi-axis acceleration data can indicate that a person is walking up a set of stairs, and from that one can infer how much energy they are using. In another aspect, body fat measurement (e.g. from impedance data) could be combined with an activity index generated from a combination of measured biomarkers to generate a physiological index useful for management of a weight loss or cardiovascular health program. This information can be combined with cardiac performance indicators to get a good picture of overall health, which can be combined with pharmaceutical therapy administration data. In another aspect, one might find for example that a particular pharmaceutical correlates with a small increase in body temperature, or a change in the electrocardiogram. One can develop a pharmacodynamic model for the metabolism of the drug, and use the information from the receiver to essentially fit the free parameters in that model to give much more accurate estimation of the levels actually present in the serum of the subject. This information could be fed back to dosing regimens. In another aspect, one can combine information from a sensor that measures uterine contractions (e.g. with a strain gauge) and that also monitors fetal heart rate, for use as a high-risk pregnancy monitor.

In certain aspects, the subject specific information that is collected using the systems of the invention may be transmitted to a location where it is combined with data from one or more additional individuals to provide a collection of data which is a composite of data collected from two or more, e.g., five or more, ten or more, twenty five or more, fifty or more, one hundred or more, one thousand or more, etc., individuals. The composite data can then be manipulated, e.g., categorized according to different criteria, and made available to one or more different types of groups, e.g., patient groups, health care practitioner groups, etc., where the manipulation of data may be such as to limit the access of any given group to the type of data that group can access. For example, data can be collected from a hundred different individuals that are suffering from the same condition and taking the same medication. The data can be processed and employed to develop easy to follow displays regarding patient compliance with a pharmaceutical dosage regimen and general health. Patient members of the group can access this information and see how their compliance matches with other patient members of the group, and whether they are enjoying the benefits that others are experiencing. In yet another aspect, doctors can also be granted access to a manipulation of the composite data to see how their patients are matching up with patients of other doctors, and obtain useful information on how real patients respond to a given therapeutic treatment regimen. Additional functionalities can be provided to the groups given access to the composite data, where such functionalities may include, but are not limited to: ability to annotate data, chat functionalities, security privileges, etc.

The receivers may be part of the systems described in PCT Application Serial No. PCT/US08/85048; PCT Application Serial No. PCT/US2007/024225 published as WO 2008/095183; PCT Application Serial No. PCT/US2007/024225 published as WO 2008/063626 and PCT Application Serial No. US2006/016370 published as WO 2006/116718; the disclosures of which are herein incorporated by reference.

In accordance with another aspect of the present invention, the receivers may be implemented in various ways, including an implantable device, a semi-implantable device, such as a subcutaneous device, and an externally applied or positioned device, such as a personal signal receiver and each may be used on conjunction with a dosage deliver system. Examples of receiver configurations of interest include, but are not limited to, those described in PCT Application Serial No. PCT/US08/85048 published as WO 2009/070773; PCT Application Serial No. PCT/US2007/052845 published as WO 2008/095183; PCT Application Serial No. PCT/US2007/024225 published as WO 2008/063626 and PCT Application Serial No. US2006/016370 published as WO 2006/116718; the disclosures of which are herein incorporated by reference. One example of a personal signal receiver for use with dosage delivery systems is a "patch" receiver removably affixed to the skin or apparel of a user. Other implementations include a wristband or an IV access device. In some implementations, the receivers may be implemented as a personal health signal receiver associated with the body, e.g., located inside, or within close proximity to a body, configured to receive and decode a signal from an in vivo transmitter located inside the body.

The receivers in accordance with the teaching of the present invention may also be configured to receive information from other sources as well, such as intelligent event marker (IEM) data. When that is the case, the receiver 105 may detect data associated with an IEM event, such as the administration of medication including a radio frequency identifier-like marker, process and forward the data to another device, such as glucometer 110 and/or wireless device 115, for further processing and forwarding to dosage manager 160.

In certain aspects, the system further includes an element for storing data, i.e., a data storage element. The data storage element may be a computer readable medium. The term "computer readable medium" as used herein refers to any physical storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

The invention also provides computer executable instructions (i.e., programming) for performing the above methods. The computer executable instructions are present on a physical computer readable medium. Accordingly, the invention provides a computer readable medium containing programming for use in detecting and processing a signal generated by a composition of the invention, e.g., as reviewed above.

As reviewed above, in certain aspects of interest, the receiver includes a semiconductor support component. Any of a variety of different protocols may be employed in manufacturing the receiver structures and components thereof. For example, molding, deposition and material removal, e.g., planar processing techniques, such as Micro-Electro-Mechanical Systems (MEMS) fabrication techniques, including surface micromachining and bulk micromachining techniques, may be employed. Deposition techniques that may be employed in certain aspects of fabricating the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain aspects is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in copending PCT application serial no. PCT/US2006/016370; the disclosure of which is herein incorporated by reference.

In certain aspects, off-the-shelf components may be employed to fabricate the receivers or components thereof. For example, an off-the-shelf instrumentation amplifier for the input amp may be employed, e.g., in bare die form. Custom logic, either in an FPGA or in an ASIC, that handles the demodulator, the memory, the microprocessor functions, and all the interface functions may be used. The transmitter may be an off-the-shelf chip, e.g., in the mixed communication band, which is approved for medical implants. The clock may be a stand-alone clock, or the device may have a microprocessor that has a clock built in.

Aspects of the invention further include methods of using receivers. In methods of receivers, a receiver receives an input signal in some manner, where the input signal may vary. Examples of input signals include, but are not limited to: transbody conductively received signals (such as may be received from an IEM or smart parenteral device), signals obtained by device sensors, such as physiological parameter and/or environmental signals, etc. Various aspects of the invention further include the device acting in some manner in response to receiving the input signal, e.g., relaying a signal to a second device, delivering an active agent to a subject with which the device is associated, etc.

In some methods of invention, as an optional step, a signal is first conductively transmitted from an in vivo transmitter, such as an IEM. The transmitted signal is then received by the receiver, where it may be stored to a memory, retransmitted to another receiver, output to a user, e.g., either directly or via a third device, e.g., an external PDA, etc. In the methods of the subject invention in which the in vivo transmitter is an IEM, the IEM is administered as desired, via ingestion.

The subject methods find use in the treatment of a variety of different conditions, including disease condition applications. The specific disease conditions treatable by with the subject compositions are as varied as the types of active agents that can be present in the subject compositions. Thus, disease conditions include, but are not limited to: cardiovascular diseases, cellular proliferative diseases, such as neoplastic diseases, autoimmune diseases, hormonal abnormality diseases, infectious diseases, pain management, neurological diseases, e.g., epilepsy, and the like.

By treatment is meant at least an amelioration of the symptoms associated with the disease condition afflicting the subject, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition. Accordingly, "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

A variety of subjects are treatable according to the present methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In representative aspects, the subjects will be humans.

In certain aspects, the subject methods, as described above, are methods of managing a disease condition, e.g., over an extended period of time, such as one week or longer, one month or longer, six months or longer, one year or longer, two years or longer, five years or longer, etc. The subject methods may be employed in conjunction with one or more additional disease management protocols, e.g., electrostimulation based protocols in cardiovascular disease management, such as pacing protocols, cardiac resynchronization protocols, etc; lifestyle, such a diet and/or exercise regimens for a variety of different disease conditions; etc.

In certain aspects, the methods include modulating a therapeutic regimen based data obtained from the compositions. For example, data may be obtained which includes information about patient compliance with a prescribed therapeutic regimen. This data, with or without additional physiological data, e.g., obtained using one or more sensors, such as the sensor devices described above, may be employed, e.g., with appropriate decision tools as desired, to make determinations of whether a given treatment regimen should be maintained or modified in some way, e.g., by modification of a medication regimen and/or implant activity regimen. As such, methods of invention include methods in which a therapeutic regimen is modified based on signals obtained from the composition(s).

In certain aspects, also provided are methods of determining the history of a composition of the invention, where the composition includes an active agent, an identifier element and a pharmaceutically acceptable carrier. In certain aspects where the identifier emits a signal in response to an interrogation, the identifier is interrogate, e.g., by a wand or other suitable interrogation device, to obtain a signal. The obtained signal is then employed to determine historical information about the composition, e.g., source, chain of custody, etc. In certain aspects, this determining step may include accessing a database or analogous compilation of stored history for the composition.

Receivers of the invention find use in a variety of different applications. Medical aspects of the present invention provide the clinician an important new tool in their therapeutic armamentarium: automatic detection and identification of pharmaceutical agents actually delivered into the body. The applications of this new information device and system are multifold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is reviewed in greater detail below in PCT Application Serial No. PCT/US08/85048; PCT Application Serial No. PCT/US2007/024225 published as WO 2008/095183; PCT Application Serial No. PCT/US2007/024225 published as WO 2008/063626 and PCT Application Serial No. US2006/016370 published as WO 2006/116718; the disclosures of which are herein incorporated by reference.

Receivers of interest also find use in conjunction with delivery of therapeutic fluids to a subject. Of interest is the use of the receivers in conjunction with smart parenteral delivery devices, such as described in PCT application serial no. PCT/US2007/015547 published as WO 2008/008281; the disclosure of which is herein incorporated by reference. When used in conjunction with such fluid delivery devices (such as a smart parenteral device), the receiver may be configured to receive data regarding the actual amounts of therapeutic fluid that has been administered. The receiver may be configured to combine this particular data with other relevant data, such as analyte testing data, physiological data, etc., where these additional types of data may be obtained with the receiver or another type of test, such as a dedicated home use analyte testing device, etc. Furthermore, the receiver may be configured to take one or more actions based on the received information, including but not limited to: relay data to a second device, modify a therapeutic regimen, etc.

Also of interest are applications in which the receivers are not used to receive a signal from an IEM or smart-parenteral delivery system. One such application of interest in which receivers of the invention find use is in epileptic seizure detection. Such devices include an epileptic seizure detection module, which module is configured to employ one or more types of received data to determine whether the subject is about to or is suffering from an epileptic seizure. Accordingly, in these applications, one or more types of physiological data are obtained with the receiver and processed to determine whether the subject is about to or is suffering from an epileptic seizure. In other words, the receiver employs obtained physiological data to make a seizure prediction or detect a seizure occurrence. Physiological data that may be obtained and used in these applications include electroencephalographic (EEG) data, accelerometer data, heart rate (ECG) data, etc. A single type of data may be obtained or two or more different types of data may be obtained and processed to make a determination as to whether a subject is about or is suffering from an epileptic seizure. In some instances, data obtained by the receiver may be combined with data from other sources and processed to make the determination. Data may include, for example, a distinctive signature on the accelerometer or heart rate variability. Sensor data may be integrated from the EEG, either as part of the system or as an ancillary input, as desired. With multiple data streams one can detect "kindling," the set of events that lead up to a seizure. In such instances, medical therapy may be adjusted based on seizure state, as desired. Neuromodulation devices may be adapted to these needs—measuring EEG or adjusting therapy.

The receiver may be configured to make the determination using any convenient protocol. One or more algorithms may be employed which use the obtained physiological data to make a determination as to whether a seizure is about to occur or is occurring. Examples of such algorithms include, but are not limited to: algorithms for automated seizure warning (ASWAs) (for example as described in published United States Patent No. 20070213786); algorithms for detecting chirp-like time-frequency variations in an EEG signal (for example as described in Sen et al., "Analysis of Seizure EEG in kindled epileptic rats," Computational and Mathematical Methods in Medicine, Volume 8, Issue 4 Dec. 2007, pages 225-234; etc.

In such applications, prediction or detection of an epileptic seizure may result in a number of additional actions. In some instances, the receiver may be configured to produce and emit an alert signal. The alert signal may or may not be detectable to the subject. For example, the alert signal may take the form of an audible or visual signal which can be detected by the subject. The alert signal may also be a signal that is sent to a health care professional or other person, e.g., via a wireless communication protocol. The alert signal may be employed in a number of different ways, e.g., to alert a health care profession to provide assistance to the subject, to instigate or modify a therapeutic regimen, etc.

In some instances, the receiver is configured as a "closed-loop" epileptic therapy device, where the receiver includes an epileptic therapeutic component, such as a pharmacological or electrical therapeutic component. In these instances, the prediction or detection of the epileptic seizure may be employed by the receiver to instigate epileptic therapy (for example by delivery of an active agent and/or electrical stimulation or by directing another device to take one or more of such actions). Alternatively, an existing epileptic therapy protocol may be modified based on the predicted or detected seizure, e.g., in terms of dosage, duration, etc.

Receivers of the invention also find use in tracking applications, in which one or more persons, e.g., patients, soldiers, etc., are monitored over a given period of time. Receivers employed in these aspects may include a number of a different physiological and/or environmental sensing modules, such as the accelerometer and ECG sensing modules described above, in order to monitor health status of a subject over time. This data may be combined with positional data, e.g., as provided by a GPS module, in order to track a subject with respect to location as a function of time.

One specific type of tracking application of interest is the tracking personnel, e.g., work personnel in an active employment setting, such as military personnel in a battlefield setting, fire and rescue personnel in a fire setting, health care personnel in a hospital, etc. In such applications, receivers of the invention may include functional modules for determining certain physiological states which are common in the setting of interest. For example, functional modules for determining certain physiological states which are common battlefield conditions may be present. Examples of such functional modules include the accelerometer and ECG functional modules described above, as these particular functional modules provide useful data regarding mobility and vital activity. When one or more of critical limits are reached in or more physiological states of interest (for example the soldier is no longer mobile and/or vital sign activity is no longer adequate), the receiver may be configured to send a warning signal to a leader/medic unit, thereby indicating that a soldier is in need of immediate care. For example, if temperature sensors of the receiver indicate cold weather and that the soldier's body temperature has begun to fall below a specified minimum, receiver may automatically signal the leader/medic unit and a command unit that the soldier is likely suffering from hypothermia. The leader or medic operating the leader/medic unit or a person operating the central control unit may then notify other soldiers or medical personnel in the area that the soldier should be treated for the condition as soon as possible. Similarly, a wounded soldier can be monitored for symptoms and severity of injury or shock ensuing from blood loss.

In these applications, each receiver may be customized to the particular wearer. Thus, a given receiver may contain information about the individual such as allergies to medications and other medical information which would be important to medical personnel treating the individual. Additionally, the receiver may keep a short physiological history, such as the body temperature, heart rate, body positions, blood pressure, oxygen saturation and movement for the last four hours or some other time period. The information can be forwarded to a field leader/medic unit or the command unit upon request. This can be accomplished either by the remote communications system of the receiver, or by a direct link-up between the receiver and the leader/medic unit when a medic having a leader/medic unit, arrives to treat the user.

In these applications, the receiver or leader/medic unit could include software/firmware for providing guidance and medical decision support. Additionally, a microprocessor disposed therein, or in the receiver, could be programmed to control fluid infusion, drug delivery, and ventilator support for the patient, thereby enabling efficacious treatment even under battlefield conditions. The receiver may communicate via a variety of predetermined schemes, e.g., with the leader/medic unit or command unit either continuously or in brief bursts so as to prevent enemy combat forces from tracking the communications to locate the soldier. The bursts may occur periodically on schedule, or as indicated by the leader/medic control unit or command unit.

In these applications, the leader/medic unit may be a portable device worn by medics and other leaders to allow each to monitor those for whom they are responsible. The leader/medic unit may contain a communications system for communicating with the receivers and the command units, and/or may contain a display which allows the user to graphically monitor the locations of personnel on the battlefield, and/or to view the physiological conditions of each soldier within the command structure for that leader. The leader/medic unit may receive information as to the location of the injured soldier, and may receive medical information while the medic is relocating to the site of the soldier. When used by a medic, this unit enables the medic to view vital signs and other information about the injured soldier prior to actually examining the soldier. Thus, the medic is able to conduct an initial evaluation of the injured soldier while in transit to the soldier's location. Additionally, because the receiver also communicates with the command unit, medical personnel at a central command post can instruct the medic on diagnosis and treatment options as the medic is en route to the casualty. By continually monitoring the location and status of the soldiers, significant decreases in casualty rates can be achieved. Additionally, the technology used in the present invention can be modified slightly to maintain high levels of care in civilian medical applications while significantly decreasing the costs.

While the above description has been provided in terms of tracking military personnel, the receivers may be employed in tracking any type of personnel, particular in an active work setting in which the personnel are located at a stationary position for extended periods of time.

Non-personnel tracking applications are also provided. Receivers may be employed in hospital settings for patient tracking and management. Rather than requiring nurses to track down patients to take their vital signs, the receivers may be employed by nurses or other health care practitioners to determine a patient's location, as well as their vital signs. If the information received indicated a problem, the location of the patient could be readily determined. Thus, a smaller number of nurses could be used while providing a higher level of care.

Also provided are kits for practicing the subject methods. Kits may include one or more receivers of the invention, as described above. In addition, the kits may include one or more dosage compositions, e.g., in the form of IEM compositions. The dosage amount of the one or more pharmacological agents provided in a kit may be sufficient for a single application or for multiple applications. Accordingly, in certain aspects of the subject kits a single dosage amount of a pharmacological agent is present and in certain other aspects multiple dosage amounts of a pharmacological agent may be present in a kit. In those aspects having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

In certain aspects, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other aspects, the instructions are present as an electronic storage data file present on a suitable computer readable storage medium, e.g. CD-ROM, diskette, etc. In yet other aspects, the actual instructions are not present in the kit, but means for obtaining the instructions from a remote source, e.g. via the internet, are provided. An example of this aspect is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many aspects of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described. All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention are embodied by the appended claims.

What is claimed is:

1. A physiological communication receiver that can be removably secured to a subject's skin, the receiver comprising:
   a housing;
   a power source secured within the housing;
   a processing unit electrically coupled to the power source and secured within the housing; and
   at least two electrodes electrically coupled to the processing unit and secured to the perimeter of the housing such that the electrodes will contact the subject's skin, wherein the processing unit is configured to receive data encoded in an electrical alternating current in a frequency range of 3 kHz to 300 kHz conducted through the body tissue of the subject, wherein the at least two electrodes are configured to detect a differential voltage therebetween corresponding to the electrical alternating current conducted through the body tissue of the subject intervening the at least two electrodes, and wherein the electrical alternating current is associated with a device associated with the subject.

2. The receiver of claim 1, wherein the processing unit is configured to receive encoded physiological information as a physiological signal at a frequency greater than 0 Hz and less than 5 kHz conducted through the body tissue of the subject, wherein the at least two electrodes are configured to detect a differential voltage therebetween corresponding to the physiological signal conducted through the body tissue of the subject intervening the at least two electrodes, and wherein the physiological signal is associated with the subject's physiology.

3. The receiver of claim 2, further comprising a communication module electrically coupled to the processing unit, wherein the communication module allows for wireless communication between the receiver and a device external to the subject such that the receiver can provide the physiological information to the device external to the subject.

4. The receiver of claim 3, wherein the communication module is configured to communicate using a frequency hopping spread spectrum communication protocol.

5. The receiver of claim 2, further comprising a communication module electrically coupled to the processing unit, wherein the communication module allows for wireless communication between the receiver and a device external to the subject such that the receiver can provide control information to the device external to the body and wherein the control information is derived from the data encoded in the electrical alternating current provided by the device associated with the subject.

6. The receiver of claim 5, wherein the device external to the subject is a control unit associated with a pharmaceutical delivery system that includes a pharmaceutical product and can alter the delivery dosage of a pharmaceutical product.

7. The receiver of claim 6, wherein the pharmaceutical delivery system comprises a fluid containment unit having a chamber configured to contain a fluid and a plunger secured to the fluid containment unit, wherein the plunger is controlled by the control unit based on the control information provided by the receiver.

8. The receiver of claim 7, wherein the fluid containment unit is an intravenous bag containing the fluid.

9. The receiver of claim 1, further comprising a power management module electrically coupled to the power source and the processing unit such that the power management module controls the power output from the power source to the processing unit and wherein the power management module is configured to monitor a signal generated by a beacon switching module, wherein the signal indicates a detection of the electrical alternating current, and wherein the power management module is configured to switch the processing unit from an inactive state to an active state when the power management module receives the signal from the beacon switching module.

10. The receiver of claim 9, wherein the power management module comprises:
    a high power operation module to control high power output from the power supply to the processing unit when the processing unit is in the active state;
    an intermediate power operation module to control intermediate power output from the power supply to the processing unit while the processing unit is in an active non-operation state; and
    a lower power operation module to control low power output from the power supply.

11. The receiver of claim 10, further comprising a beacon switching module configured to send a signal to the intermediate power operation module to allow the processing unit to switch to the active non-operation state.

12. The receiver of claim 1, wherein the receiver further comprises a beacon switching module, and wherein the beacon switching module comprises:
    a counter;
    a beacon signal generator coupled to the counter for generating a plurality of beacon signals; and
    a memory unit coupled to the beacon signal generator, wherein the memory unit is configured to store an algorithm that the beacon signal generator is configured to execute to determine a time lapse between each of the plurality of beacon signals.

13. The receiver of claim 1, further comprising:
    a router coupled to the power source; and
    a connector electrically coupled to the router, wherein the router is configured to control electrical connection paths between a device external to the subject and wherein the connector is physically connected to the receiver and the power source.

14. The receiver of claim 13, wherein an electrical signal from the device external to the subject comes from an external power source that charges the power source in the receiver.

* * * * *

UNITED STATES PATENT AND TRADEMARK OFFICE
CERTIFICATE OF CORRECTION

| | | |
|---|---|---|
| PATENT NO. | : 8,114,021 B2 | Page 1 of 1 |
| APPLICATION NO. | : 12/673326 | |
| DATED | : February 14, 2012 | |
| INVENTOR(S) | : Timothy Robertson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Twenty-seventh Day of November, 2012

David J. Kappos
*Director of the United States Patent and Trademark Office*